US012760025B2

(12) United States Patent
Zuercher et al.

(10) Patent No.: US 12,760,025 B2
(45) Date of Patent: Oct. 13, 2026

(54) SELECTIVE CYCLIN-DEPENDENT KINASE INHIBITORS AND METHODS OF THERAPEUTIC USE THEREOF

(71) Applicant: ViroKyne Therapeutics, LLC, Raleigh, NC (US)

(72) Inventors: William J. Zuercher, Mies (CH); Nathaniel J. Moorman, Chapel Hill, NC (US)

(73) Assignee: ViroKyne Therapeutics, LLC, Raleigh, NC (US)

( * ) Notice: Subject to any disclaimer, the term of this patent is extended or adjusted under 35 U.S.C. 154(b) by 487 days.

(21) Appl. No.: 18/263,206

(22) PCT Filed: Jan. 28, 2022

(86) PCT No.: PCT/US2022/014293
§ 371 (c)(1),
(2) Date: Jul. 27, 2023

(87) PCT Pub. No.: WO2022/165162
PCT Pub. Date: Aug. 4, 2022

(65) Prior Publication Data

US 2024/0309004 A1 Sep. 19, 2024

Related U.S. Application Data

(60) Provisional application No. 63/143,342, filed on Jan. 29, 2021.

(51) Int. Cl.

| | |
|---|---|
| ***C07D 487/04*** | (2006.01) |
| ***A61K 31/519*** | (2006.01) |
| ***A61K 45/06*** | (2006.01) |
| ***A61P 31/22*** | (2006.01) |

(52) U.S. Cl.
CPC .......... *C07D 487/04* (2013.01); *A61K 31/519* (2013.01); *A61K 45/06* (2013.01); *A61P 31/22* (2018.01)

(58) Field of Classification Search
CPC ..... C07D 487/04; A61P 31/22; A61K 31/519; A61K 45/06
See application file for complete search history.

(56) References Cited

U.S. PATENT DOCUMENTS 4,366,231 A 12/1982 Mayer et al.

FOREIGN PATENT DOCUMENTS

WO WO 2005/005438 A1 1/2005

OTHER PUBLICATIONS

Cingöz et al., Cyclin-dependent kinase activity is required for type I interferon production, Proceedings of the National Academy of Sciences, (2010), 115(13), E2950-E2959 (Year: 2010).*
Zoubir et al., An inhibitor of cyclin-dependent kinases suppresses TLR signaling and increases the susceptibility of cancer patients to herpes viridae. Cell Cycle, (2018), 10(1), 118-126 (Year: 2018).*
Zydek et al., Cyclin-Dependent Kinase Activity Controls the Onset of the HCMV Lytic Cycle. PLoS Pathogens, (2010), 6(9), e1001096 (Year: 2010).*
Extended EP Search Report for EP 22746683.6, mailed Nov. 18, 2024, 9 pages.
International Search Report and Written Opinion for PCT/US2022/014293. Mailed May 4, 2022. 10 pages.
Arend et al., Kinome Profiling Identifies Druggable Targets for Novel Human Cytomegalovirus (HCMV) Antivirals. Mol Cell Proteomics. Apr. 2017;16(4 suppl 1):S263-S276.
Azevedo et al., Cytomegalovirus infection in transplant recipients. Clinics (Sao Paulo). Jul. 2015;70(7):515-23.
Beadle et al., Synthesis and Antiviral Evaluation of Octadecyloxyethyl Benzyl 9-[(2-Phosphonomethoxy)ethyl]guanine (ODE-Bn-PMEG), a Potent Inhibitor of Transient HPV DNA Amplification. J Med Chem. Dec. 8, 2016;59(23):10470-10478.
Berge et al., Pharmaceutical salts. J Pharm Sci. Jan. 1977;66(1):1-19.
Gill et al., Conserved retinoblastoma protein-binding motif in human cytomegalovirus UL97 kinase minimally impacts viral replication but affects susceptibility to maribavir. Virol J. Jan. 21, 2009:6:9. 5 pages.
Gupta et al., HPV: Molecular pathways and targets. Curr Probl Cancer. Mar.-Apr. 2018;42(2):161-174.
Hartline et al., A standardized approach to the evaluation of antivirals against DNA viruses: Orthopox-, adeno-, and herpesviruses. Antiviral Res. Nov. 2018:159:104-112.
Kapasi et al., Inhibition of the cyclin-dependent kinases at the beginning of human cytomegalovirus infection specifically alters the levels and localization of the RNA polymerase II carboxyl-terminal domain kinases cdk9 and cdk7 at the viral transcriptosome. J Virol. Jan. 2008;82(1):394-407.
Keith et al., A standardized approach to the evaluation of antivirals against DNA viruses: Polyomaviruses and lymphotropic herpesviruses. Antiviral Res. Nov. 2018:159:122-129.
Lavoie et al., Src-family kinase signaling, actin-mediated membrane trafficking and organellar dynamics in the control of cell fate: lessons to be learned from the adenovirus E4orf4 death factor. Cell Signal. Nov. 2010;22(11):1604-14.
Leung et al., Quantification of polyoma BK viruria in hemorrhagic cystitis complicating bone marrow transplantation. Blood. Sep. 15, 2001;98(6):1971-8.
Li et al., Potential of protein kinase inhibitors for treating herpesvirus-associated disease. Trends Microbiol. Jun. 2013;21(6):286-95.
Prasad et al., Cell Cycle-Dependent Kinase Cdk9 Is a Postexposure Drug Target against Human Adenoviruses. ACS Infect Dis. Jun. 9, 2017;3(6):398-405.
Prichard et al., Activity and mechanism of action of N-methanocarbathymidine against herpesvirus and orthopoxvirus infections. Antimicrob Agents Chemother. Apr. 2006;50(4):1336-41.

(Continued)

*Primary Examiner* — Renee Claytor
*Assistant Examiner* — Christopher Lindsay Johnson
(74) *Attorney, Agent, or Firm* — Casimir Jones, SC; Jeffrey W. Childers

(57) ABSTRACT

Selective inhibitors of cyclin-dependent kinases (CDKs) and methods of their therapeutic use, including treatment of viral infections, are disclosed.

18 Claims, No Drawings

(56) References Cited

OTHER PUBLICATIONS

Prichard et al., Benzimidazole analogs inhibit human herpesvirus 6. Antimicrob Agents Chemother. May 2011;55(5):2442-5.
Pubchem, SID 369026317. Available May 25, 2018. 5 pages.
Remington: The Science and Practice of Pharmacy. Lippincott, Williams & Wilkins. 2000. TOC only. 28 pages.
Sanchez et al., Cyclin-dependent kinase activity is required at early times for accurate processing and accumulation of the human cytomegalovirus UL122-123 and UL37 immediate-early transcripts and at later times for virus production. J Virol. Oct. 2004;78(20):11219-32.
Sanchez et al., Cyclin-dependent kinase activity is required for efficient expression and posttranslational modification of human cytomegalovirus proteins and for production of extracellular particles. J Virol. Jun. 2006;80(12):5886-96.
Sanchez et al., Mechanisms governing maintenance of Cdk1/cyclin B1 kinase activity in cells infected with human cytomegalovirus. J Virol. Dec. 2003;77(24):13214-24.
Simon et al., Infectious complications of solid organ transplantations. Infect Dis Clin North Am. Jun. 2001;15(2):521-49.
Sinclair et al., Latency and reactivation of human cytomegalovirus. J Gen Virol. Jul. 2006;87(Pt 7):1763-1779.
Tamrakar et al., Human cytomegalovirus infection induces specific hyperphosphorylation of the carboxyl-terminal domain of the large subunit of RNA polymerase II that is associated with changes in the abundance, activity, and localization of cdk9 and cdk7. J Virol. Dec. 2005;79(24):15477-93.
Wang et al., Functionally active cyclin-dependent kinase 9 is essential for porcine reproductive and respiratory syndrome virus subgenomic RNA synthesis. Mol Immunol. Jul. 2021:135:351-364.
Wuts et al., Protective Groups in Organic Synthesis, John Wiley & Sons. 2007. TOC only. 6 pages.

* cited by examiner

SELECTIVE CYCLIN-DEPENDENT KINASE INHIBITORS AND METHODS OF THERAPEUTIC USE THEREOF

BACKGROUND

Protein kinases play a critical role in the regulation of multiple cellular signaling pathways. Aberrant activation of kinases is connected to a large number of diseases and pathologies including cancer, diabetes, inflammation, and viral infection. As such, the design and application of selective protein kinase inhibitors has become a major industry and kinases have been proven to be highly promising targets for small molecules.

The cyclin-dependent kinases (CDKs) are an important family of cell cycle regulatory kinases. While largely characterized by the CDKs that govern cell cycle progression (CDKs1-7), within this family there exist CDKs that are essential regulators of gene expression. An example is CDK9, which is part of the pTEFb transcriptional complex involved in regulating gene expression through phosphorylation of RNA polymerase. CDKs have been recognized as antiviral targets, including for human cytomegalovirus (HCMV). See, e.g., Sanchez et al., 2003; Arend et al., 2017. Recently, CDK9 selective inhibitors have been developed that avoid the cell cycle regulatory CDKs and effectively suppress gene transcription.

Human cytomegalovirus (HCMV) is a ubiquitous herpes virus that infects up to 60-100% of individuals in adulthood. HCMV is a significant source of morbidity and mortality in individuals with a compromised immune system, including, but not limited to, solid organ and tissue transplant recipients, individuals infected with HIV, and congenitally infected fetuses or neonates.

HCMV is one of the main infectious agents involved in complications after solid organ transplantation (SOT). See Azevedo et al., 2015. Post-transplant HCMV infection can arise due to transmission from an infected transplanted organ, reactivation of a latent infection in the transplant recipient, or after a primary infection in the transplant recipient.

Similar to other herpesviruses, HCMV establishes a latent infection after an initial infection. It can remain latent throughout the lifetime of the host with sporadic reactivation. The primary infection of hosts with a functional immune system is associated with mild symptoms, although it can progress with fever, hepatitis, splenomegaly and mononucleosis-like symptoms. In contrast, when primary infection or reactivation occurs in immunocompromised or immunodeficient hosts, they often experience life-threatening diseases, including pneumonia, hepatitis, retinitis and encephalitis. See Sinclair and Sissons, 2006.

The occurrence of disease caused by CMV in transplanted patients without prophylaxis varies according to the type of transplantation, the serological match between donor and recipient, the immunosuppressive drugs used, and additional illness risk factors. The incidence of CMV is between 9 and 23% after heart transplantation, between 22 and 29% after liver transplantation and between 8 and 32% after kidney transplantation. See Simon and Levin, 2001. The current standard of care for patients infected with HCMV is intravenous or oral ganciclovir; oral valganciclovir; or, less frequently, valacyclovir.

Human CMV replication is closely linked to regulation of the cell cycle and CDK activities. At least four CDKs have been implicated for efficient HCMV replication, namely CDK1, 2, 7 and 9. See, e.g., Kapasi and Spector, 2008; Sanchez and Spector, 2006; Tamrakar et al., 2005; Sanchez et al., 2004.

Additionally, cellular kinase activity is also critical for the efficient replication of multiple other viruses, including other herpesviruses, adenovirus, and human papillomavirus. See Li et al., 2013; Wang et al., 2021; Lavoie et al., 2010; Gupta et al., 2018; Prasad et al., 2017.

SUMMARY

In some aspects, the presently disclosed subject matter provides a compound of formula (I):

(I)

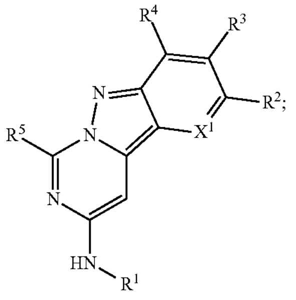

wherein:

$X^1$ is CH or N;

$R^1$ is selected from unsubstituted or substituted branched or straightchain $C_1$-$C_{12}$ alkyl, $C_3$-$C_{12}$ cycloalkyl, $C_3$-$C_{12}$ heterocycloalkyl, aryl, heteroaryl, and —C(O)—$R_6$, wherein $R_6$ is selected from unsubstituted or substituted $C_1$-$C_{12}$ alkyl, $C_3$-$C_{12}$ cycloalkyl, $C_3$-$C_{12}$ heterocycloalkyl, aryl, and heteroaryl;

$R^2$, $R^3$, $R^4$, and $R^5$ are each independently selected from hydrogen, halogen, amine, unsubstituted or substituted branched or straightchain $C_1$-$C_{12}$ alkyl, $C_3$-$C_{12}$ cycloalkyl, $C_3$-$C_{12}$ heterocycloalkyl, aryl, heteroaryl, and —C(O)—$R^6$, wherein $R_6$ is selected from unsubstituted or substituted $C_1$-$C_{12}$ alkyl, $C_3$-$C_{12}$ cycloalkyl, $C_3$-$C_{12}$ heterocycloalkyl, aryl, and heteroaryl;

or a pharmaceutically acceptable salt, hydrate, solvate, stereoisomer, ester, tautomer, or prodrug thereof.

In some aspects, the presently disclosed subject matter provides a pharmaceutical composition comprising a compound of formula (I) and a pharmaceutically acceptable excipient.

In some aspects, the presently disclosed subject matter provides the use of a compound of formula (I) in the manufacture of a medicament for use in a method of treatment of a viral disease, viral disorder, or viral condition associated with CDK function.

In some aspects, the presently disclosed subject matter provides a method for inhibiting CDK function in a cell, in vitro or in vivo, the method comprising contacting the cell with an effective amount of a compound of formula (I) or a composition thereof.

In other aspects, the presently disclosed subject matter provides a method for treating a viral disease, viral disorder, or viral condition associated with cyclin-dependent kinase (CDK) function, the method comprising administering to a subject in need of treatment thereof, a therapeutically effective amount of a compound of formula (I) or a composition thereof. In certain aspects, the viral disease, viral disorder, or viral condition is associated with one or more of an increase in activity of a CDK, a decrease in activity of a CDK, a CDK mutation, CDK overexpression, and an upstream pathway activation of CDK. In particular aspects, the method inhibits CDK. In more particular aspects, the viral disease, viral disorder, or viral condition associated with CDK function comprises a viral infection.

In yet more particular aspects, the viral disease, viral disorder, or viral condition associated with CDK function comprises a viral infection from a Herpesviridae family virus. In certain aspects, the Herpesviridae family virus is selected from Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), and combinations thereof.

In other aspects, the viral disease, viral disorder, or viral condition associated with CDK function comprises a viral infection from an Adenovirus family virus. In certain aspects, the Adenovirus family virus comprises Adenovirus-5.

In other aspects, the viral disease, viral disorder, or viral condition associated with CDK function comprises a viral infection from a Papovaviridae family virus. In certain aspects, the Papovaviridae family virus comprises papillomavirus (HPV).

In certain aspects, the viral infection comprises a drug-resistant variant of a Herpesviridae, Adenovirus, and/or Papovaviridae family of viruses.

In other aspects, the presently disclosed subject matter provides a method for treating or preventing a viral infection of a host, wherein the viral infection is from a virus selected from Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, Human papillomavirus (HPV), and combinations thereof, the method comprising administering to the host a therapeutically effective amount of a compound of formula (I) or a composition thereof.

In certain aspects, the host has, is suspected of having, or is at risk of contracting a Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, and/or Human papillomavirus (HPV) infection.

In certain aspects, the host is selected from one or more of a cell, a tissue, an organ, and an individual organism. In particular aspects, the individual organism is a mammal. In yet more particular aspects, the mammal is a human.

In certain aspects, the method further comprises administering to the host one or more additional anti-viral agents in combination with the compound of formula (I) or a composition thereof. In particular aspects, the one or more additional anti-viral agents is administered concurrently or sequentially with the compound of formula (I) or a composition thereof. In particular aspects, the one or more additional anti-viral agents is selected from ganciclovir, valganciclovir, valacyclovir, cidofovir, and/or other first-/second-/later-lines of anti-viral therapies and combinations thereof.

In certain aspects, the administering to the host a therapeutically effective amount of a compound of formula (I) or a composition thereof inhibits replication of Human cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, and/or Human papillomavirus (HPV) infection in the subject.

In certain aspects, the HCMV infection comprises a latent HCMV infection. In certain aspects, the Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, and/or Human papillomavirus (HPV) infection comprises an active infection. In other aspects, the HCMV infection comprises a reactivation of an HCMV infection after latency.

In certain aspects, the treating is a prophylactic treatment.

In certain aspects, the administering to the host a therapeutically effective amount of a compound of formula (I) or a composition thereof is oral, intravenous, or topical administration.

In certain aspects, the host is immunocompromised. In particular aspects, the host has undergone, is undergoing, or is expected to undergo a solid organ transplant or tissue transplant. In yet more particular aspects, the solid organ is selected from a heart, a kidney, a liver, a lung, a pancreas, an intestine, a thymus, and/or other organ/human tissues.

In certain aspects, the host is infected with HIV. In particular aspects, the host is a congenitally infected fetus or neonate.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

DETAILED DESCRIPTION

The presently disclosed subject matter now will be described more fully hereinafter with reference to the accompanying Examples, in which some, but not all embodiments of the inventions are described. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Examples. Therefore, it is to be understood that the presently disclosed subject matter is not to be limited to the specific embodiments disclosed and that modifications and other embodiments are intended to be included within the scope of the appended claims.

I. Selective Cyclin-Dependent Kinase Inhibitors

In some embodiments, the presently disclosed subject matter provides a compound of formula (I):

(I)

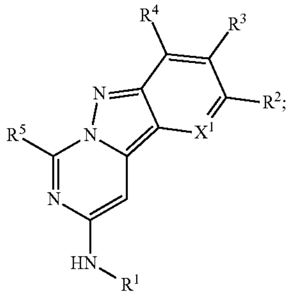

wherein:

$X^1$ is CH or N;

$R^1$ is selected from unsubstituted or substituted branched or straightchain $C_1$-$C_{12}$ alkyl, $C_3$-$C_{12}$ cycloalkyl, $C_3$-$C_{12}$ heterocycloalkyl, aryl, heteroaryl, and —C(O)—$R_6$, wherein $R_6$ is selected from unsubstituted or substituted $C_1$-$C_{12}$ alkyl, $C_3$-$C_{12}$ cycloalkyl, $C_3$-$C_{12}$ heterocycloalkyl, aryl, and heteroaryl;

$R^2$, $R^3$, $R^4$, and $R^5$ are each independently selected from hydrogen, halogen, amine, unsubstituted or substituted branched or straightchain $C_1$-$C_{12}$ alkyl, $C_3$-$C_{12}$ cycloalkyl, $C_3$-$C_{12}$ heterocycloalkyl, aryl, heteroaryl, and —C(O)—$R^6$, wherein $R_6$ is selected from unsubstituted or substituted $C_1$-$C_{12}$ alkyl, $C_3$-$C_{12}$ cycloalkyl, $C_3$-$C_{12}$ heterocycloalkyl, aryl, and heteroaryl;

or a pharmaceutically acceptable salt, hydrate, solvate, stereoisomer, ester, tautomer, or prodrug thereof.

In certain embodiments, the branched or straightchain $C_1$-$C_{12}$ alkyl, $C_3$-$C_{12}$ cycloalkyl, $C_3$-$C_{12}$ heterocycloalkyl, aryl, heteroaryl at each occurrence are optionally substituted with one or more substituent groups selected from halogen, hydroxyl, alkoxyl, cyano, nitro, oxo, —$NR^7R^8$, —$CONR^9R^{10}$, —$COOR^{11}$, —$OR^{12}$, —$OSO_3R^{13}$, —$SR^{14}$, $SO_2R^{15}$, and $SO_3R^{16}$; wherein $R^7$, $R^8$, $R^9$, $R^{10}$, R, $R^{12}$, $R^{13}$, $R^{14}$, $R^{15}$, and $R^{16}$ are each independently selected from hydrogen, unsubstituted or substituted $C_1$-$C_{12}$ alkyl, $C_3$-$C_{12}$ cycloalkyl, and aryl.

In particular embodiments, $X^1$ is N. In other embodiments, $X^1$ is CH.

In some embodiments, $R^1$ is an amino-substituted cyclohexyl or amino-substituted cyclopentyl. In some embodiments, $R^1$ is a $C_3$-$C_{12}$ heterocycloalkyl. In particular embodiments, the $C_3$-$C_{12}$ heterocycloalkyl is selected from a substituted or unsubstituted morpholine, tetrahydropyran, piperidine, and pyrrolidine.

In particular embodiments, $X^1$ is CH, $R^1$ is $C_3$-$C_{12}$ heterocycloalkyl; $R^2$, $R^4$, and $R^5$ are each H; and $R^3$ is halogen.

In certain embodiments, at least one of $R^2$, $R^3$, $R^4$, or $R^5$ is Cl or F. In certain embodiments, at least one of $R^2$, $R^3$, $R^4$, or $R^5$ is H. In certain embodiments, at least one of $R^2$, $R^3$, $R^4$, or $R^5$ is are independently substituted or unsubstituted $C_1$-$C_{12}$ alkyl. In particular embodiments, at least one of $R^2$, $R^3$, $R^4$, or $R^5$ is methyl. In particular embodiments, at least one of $R^2$, $R^3$, $R^4$, or $R^5$ is trifluoromethyl.

In certain embodiments, $R^2$, $R^3$, and $R^5$ are H, and $R^4$ is Cl. In other embodiments, $R^2$, $R^3$, and $R^5$ are H, and $R^4$ is F. In yet other embodiments, $R^2$, $R^3$, and $R^5$ are H, and $R^4$ is substituted or unsubstituted $C_1$-$C_{12}$ alkyl.

In particular embodiments, $R^4$ is methyl. In other embodiments, $R^4$ is trifluoromethyl.

In certain embodiments, $R^2$, $R^4$, and $R^5$ are H, and $R^3$ is Cl. In other embodiments, $R^2$, $R^4$, and $R^5$ are H, and $R^3$ is F. In yet other embodiments, $R^2$, $R^4$, and $R^5$ are H, and $R^3$ is substituted or unsubstituted $C_1$-$C_{12}$ alkyl.

In particular embodiments, $R^3$ is methyl. In other embodiments, $R^3$ is trifluoromethyl.

In yet more particular embodiments, the compound of formula (I) has a structure selected from:

VKT-001

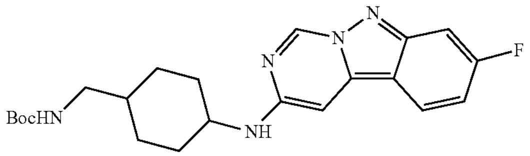

VKT-002

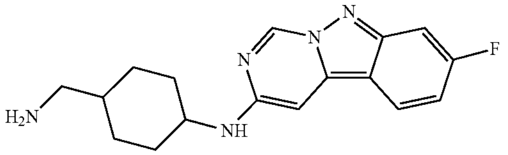

VKT-005

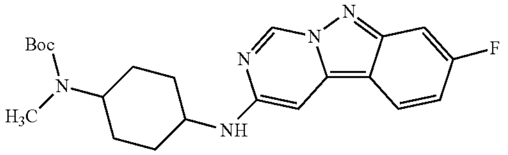

VKT-006

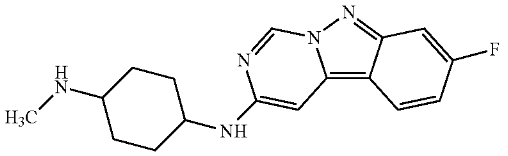

VKT-007

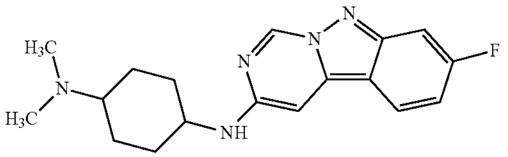

VKT-008

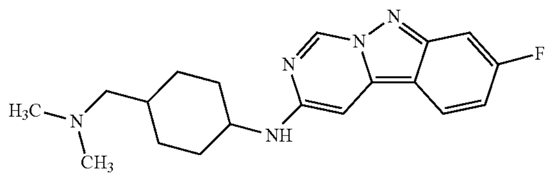

VKT-009-A

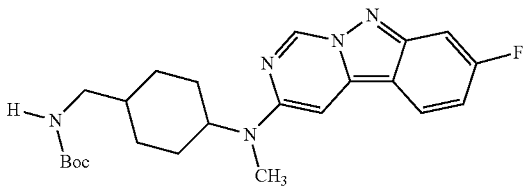

-continued
VKT-009-B
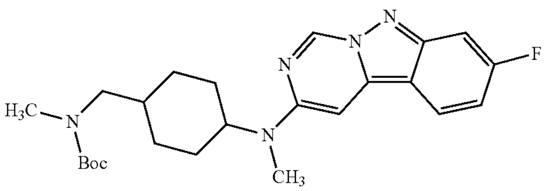
VKT-011
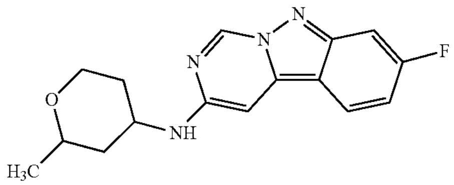
VKT-012
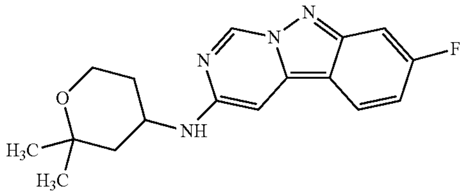
VKT-013
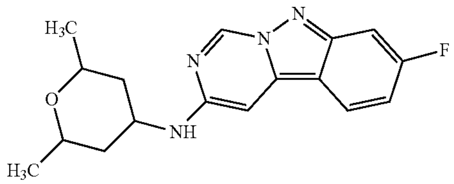
VKT-015
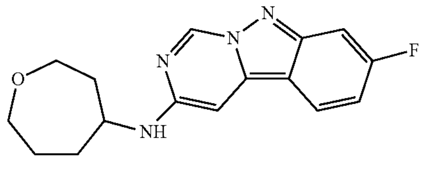
VKT-016
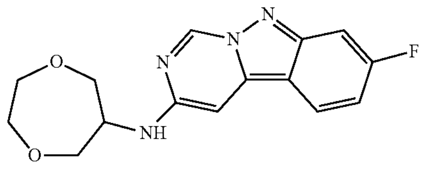
VKT-017
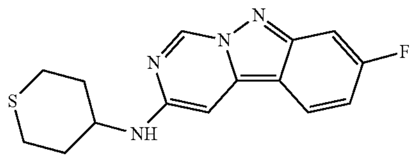
VKT-018
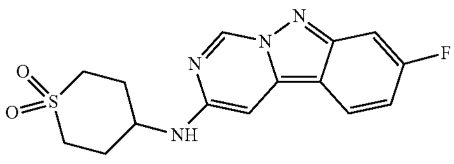
-continued
VKT-019
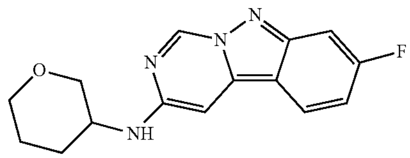
VKT-022-A
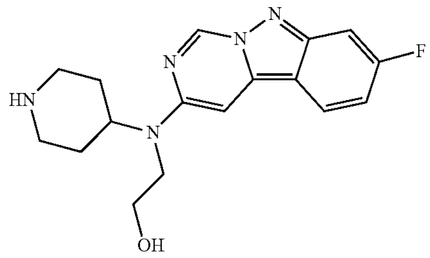
VKT-022-B
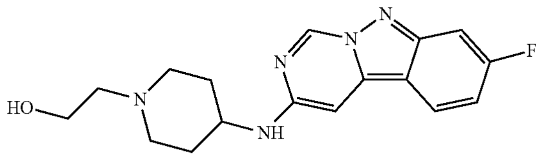
VKT-023
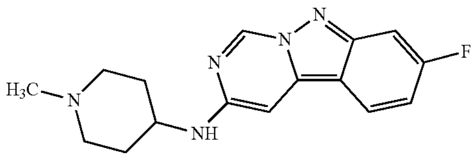
VKT-025
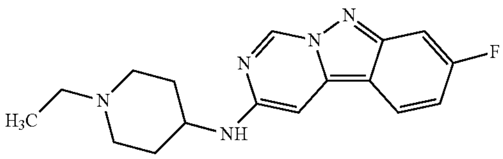
VKT-026
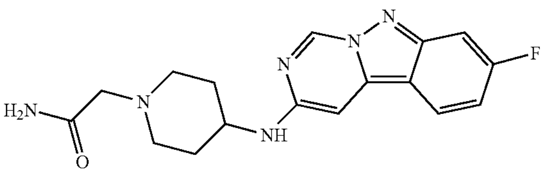
VKT-027
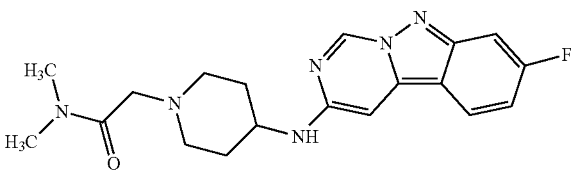
VKT-028
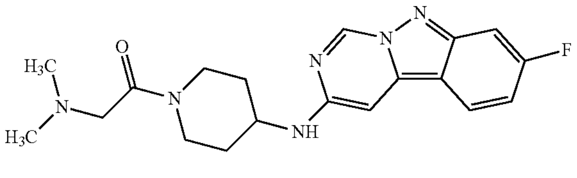

-continued
VKT-029
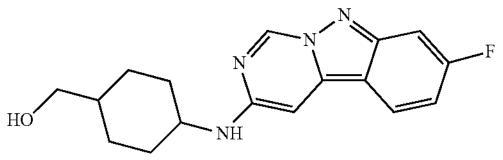
VKT-031
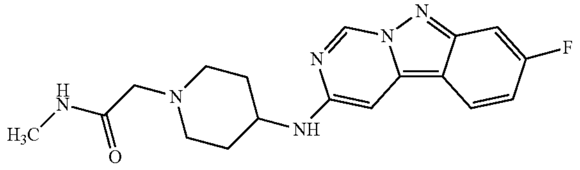
VKT-032
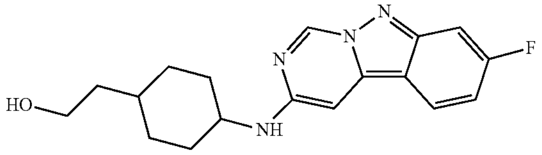
VKT-033
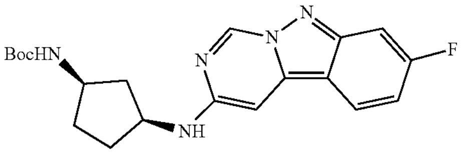
VKT-034
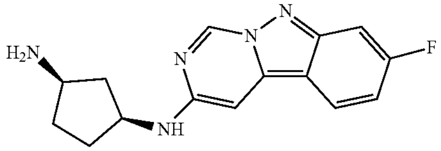
VKT-035
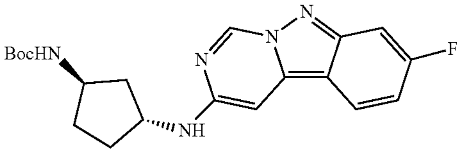
VKT-036
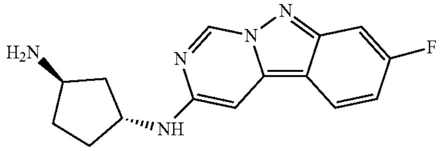
VKT-511
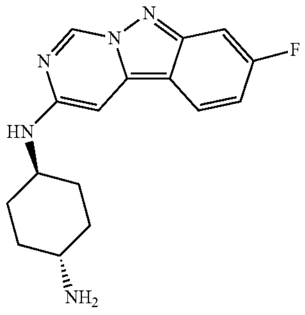
-continued
VKT-319
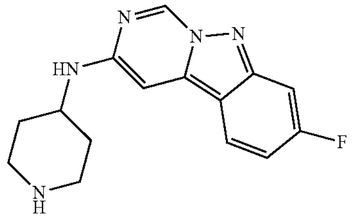
VKT-320
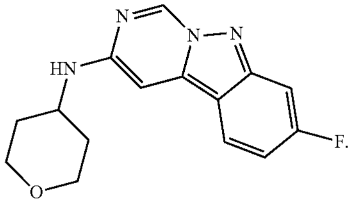
In even yet more particular embodiments, the compound of formula(I) has a structure selected from:
VKT-511
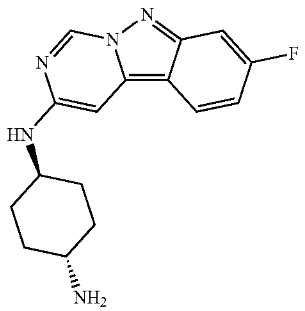
VKT-320
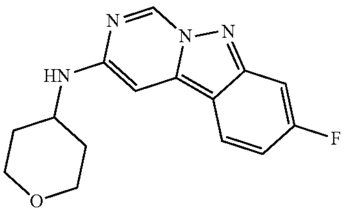
VKT-034
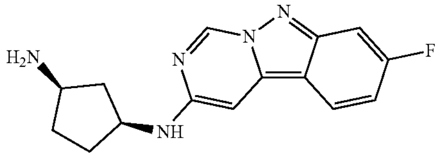
VKT-029
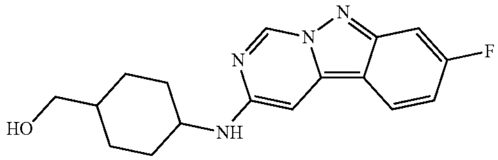

-continued

VKT-036

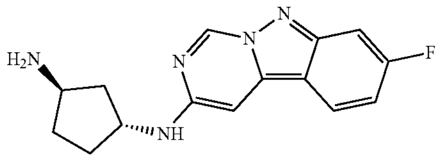

VKT-007

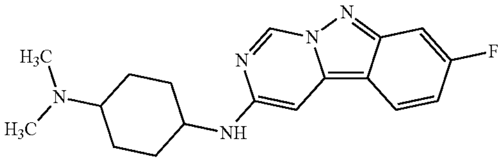

VKT-026

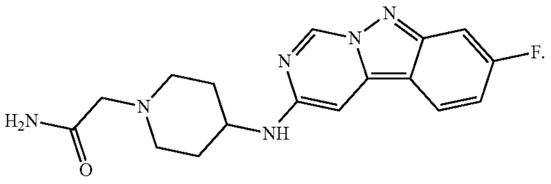

In some embodiments, the presently disclosed subject matter provides a pharmaceutical composition comprising a compound of formula (I) and a pharmaceutically acceptable excipient.

In some embodiments, the presently disclosed subject matter provides the use of a compound of formula (I) in the manufacture of a medicament for use in a method of treatment of a viral disease, viral disorder, or viral condition associated with CDK function.

II. Selective Cyclin-Dependent Kinase Inhibitors and Methods of Therapeutic Use Thereof In some embodiments, the presently disclosed subject matter provides a method for inhibiting CDK function in a cell, in vitro or in vivo, the method comprising contacting the cell with an effective amount of a compound of formula (I) or a composition thereof.

In other embodiments, the presently disclosed subject matter provides a method for treating a viral disease, viral disorder, or viral condition associated with cyclin-dependent kinase (CDK) function, the method comprising administering to a subject in need of treatment thereof, a therapeutically effective amount of a compound of formula (I) or a composition thereof.

In certain embodiments, the viral disease, viral disorder, or viral condition is associated with one or more of an increase in activity of a CDK, a decrease in activity of a CDK, a CDK mutation, CDK overexpression, and an upstream pathway activation of CDK.

In particular embodiments, the method inhibits CDK In more particular embodiments, the viral disease, viral disorder, or viral condition associated with CDK function comprises a viral infection.

In yet more particular embodiments, the viral disease, viral disorder, or viral condition associated with CDK function comprises a viral infection from a Herpesviridae family virus. In certain embodiments, the Herpesviridae family virus is selected from Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), and combinations thereof.

In other embodiments, the viral disease, viral disorder, or viral condition associated with CDK function comprises a viral infection from an Adenovirus family virus. In certain embodiments, the Adenovirus family virus comprises Adenovirus-5.

In other embodiments, the viral disease, viral disorder, or viral condition associated with CDK function comprises a viral infection from a Papovaviridae family virus. In certain embodiments, the Papovaviridae family virus comprises papillomavirus (HPV).

In certain embodiments, the viral infection comprises a drug-resistant variant of a Herpesviridae, Adenovirus, and/or Papovaviridae family of viruses.

In other embodiments, the presently disclosed subject matter provides a method for treating or preventing a viral infection of a host, wherein the viral infection is from a virus selected from Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, Human papillomavirus (HPV), and combinations thereof, the method comprising administering to the host a therapeutically effective amount of a compound of formula (I) or a composition thereof.

In certain embodiments, the host has, is suspected of having, or is at risk of contracting a Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, and/or Human papillomavirus (HPV) infection.

In certain embodiments, the host is selected from one or more of a cell, a tissue, an organ, and an individual organism. In particular embodiments, the individual organism is a mammal. In yet more particular embodiments, the mammal is a human.

In certain embodiments, the method further comprises administering to the host one or more additional anti-viral agents in combination with the compound of formula (I) or a composition thereof. In particular embodiments, the one or more additional anti-viral agents is administered concurrently or sequentially with the compound of formula (I) or a composition thereof. In particular embodiments, the one or more additional anti-viral agents is selected from ganciclovir, valganciclovir, valacyclovir, cidofovir, and/or other first-/second-/later-lines of anti-viral therapies and combinations thereof.

In certain embodiments, the administering to the host a therapeutically effective amount of a compound of formula (I) or a composition thereof inhibits replication of Human cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, and/or Human papillomavirus (HPV) infection in the subject.

In certain embodiments, the HCMV infection comprises a latent HCMV infection.

In certain embodiments, the Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, and/or Human papillomavirus (HPV) infection comprises an active infection.

In other embodiments, the HCMV infection comprises a reactivation of an HCMV infection after latency.

In certain embodiments, the treating is a prophylactic treatment.

In certain embodiments, the administering to the host a therapeutically effective amount of a compound of formula (I) or a composition thereof is oral, intravenous, or topical administration.

In certain embodiments, the host is immunocompromised. In particular embodiments, the host has undergone, is undergoing, or is expected to undergo a solid organ transplant or tissue transplant. In yet more particular embodiments, the solid organ is selected from a heart, a kidney, a liver, a lung, a pancreas, an intestine, a thymus, and/or other organ/human tissues.

In certain embodiments, the host is infected with HIV. In particular embodiments, the host is a congenitally infected fetus or neonate.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

As used herein, the term "inhibit," and grammatical derivations thereof, refers to the ability of a presently disclosed compound, e.g., a presently disclosed compound of Formula (T) to block, partially block, interfere, decrease, reduce or deactivate a CDK. Thus, one of ordinary skill in the art would appreciate that the term "inhibit" encompasses a complete and/or partial loss of activity of a CDK, e.g., a loss in activity by at least 10%, in some embodiments, a loss in activity by at least 20%, 30%, 50%, 75%, 95%, 98%, and up to and including 100%.

A "host" may be considered a single cell, a tissue, an organ, or an individual organism, such as a mammal. The mammal can be any suitable mammal, such as a mammal selected from the group consisting of a mouse, rat, guinea pig, hamster, cat, dog, pig, cow, horse, and primate. In one embodiment, the mammal is a human.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of formula (I) and at least one antiviral therapeutic, and optionally one or more antiviral agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more antibacterial agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index } (SI)$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

III. Pharmaceutical Compositions and Administration

In another embodiment, the present disclosure provides a pharmaceutical composition including one compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries that facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

IV. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., $—CH_2O—$ is equivalent to $—OCH_2—$; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-S(O)-CH_3$, $-CH_2-CH_2-S(O)_2-CH_3$, $-CH{=}CH-O-CH_3$, $-Si(CH_3)_3$, $-CH_2-CH{=}N-OCH_3$, $-CH{=}CH-N(CH_3)-CH_3$, $O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$.

As described above, heteroalkyl groups, as used herein, include those groups that are attached to the remainder of the molecule through a heteroatom, such as $-C(O)NR'$, $-NR'R''$, $-OR'$, $-SR$, $-S(O)R$, and/or $-S(O_2)R'$. Where "heteroalkyl" is recited, followed by recitations of specific heteroalkyl groups, such as $-NR'R$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($-CH_2-$); ethylene ($-CH_2-CH_2-$); propylene ($-(CH_2)_3-$); cyclohexylene ($-C_6H_{10}-$); $-CH=CH-CH=CH-$; $-CH=CH-CH_2-$; $-CH_2CH_2CH_2CH_2-$, $-CH_2CH=CHCH_2-$, $-CH_2CSCCH_2-$, $-CH_2CH_2CH(CH_2CH_2CH_3)CH_2-$, $-(CH_2)_q-N(R)-(CH_2)_r-$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

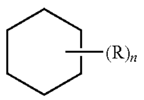

or

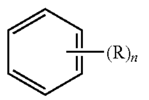

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

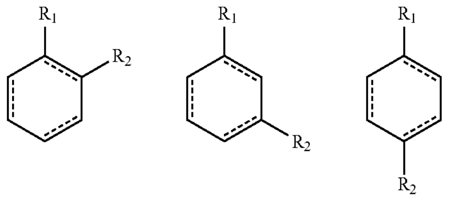

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R"', —OC(O)R', —C(O)R', —$CO_2$R', —C(O)NR'R", —OC(O)NR'R", —NR"C(O)R', —NR'—C(O)NR"R"', —NR"C(O)OR', —NR—C(NR'R")═NR"', —S(O)R', —$S(O)_2$R', —$S(O)_2$NR'R", —$NRSO_2$R', —CN, $CF_3$, fluorinated $C_{1-4}$ alkyl, and —$NO_2$ in a number ranging from zero to (2m'+1), where m' is the total number of carbon atoms in such groups. R', R", R' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —$CO_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"-S(O)R', —$S(O)_2$R', —$S(O)_2$NR'R", —$NRSO_2$R', —CN and —$NO_2$, —R', —$N_3$, —$CH(Ph)_2$, fluoro($C_{1-4}$)alkoxo, and fluoro($C_{1-4}$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R' and R"" groups when more than one of these groups is present.

Two of the substituents on adjacent atoms of aryl or heteroaryl ring may optionally form a ring of the formula -T-C(O)—$(CRR')_q$—U—, wherein T and U are independently —NR—, —O—, —CRR'— or a single bond, and q is an integer of from 0 to 3.

Alternatively, two of the substituents on adjacent atoms of aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —$(CRR')_s$—X'—$(C"R'")_d$—, where s and d are independently integers of from 0 to 3, and X' is —O—, —NR'—, —S—, —S(O)—, —$S(O)_2$—, or —$S(O)_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described and include substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)$NH_2$.

"Alkylcarbamoyl" refers to a R'RN—C(=O)— group wherein one of R and R' is hydrogen and the other of R and R' is alkyl and/or substituted alkyl as previously described.

"Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylammonium refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(═O)— group, and can include an aldehyde group represented by the general formula R—C(═O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

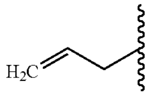
allyl

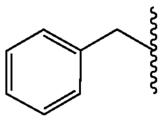
Bn

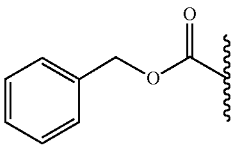
Cbz

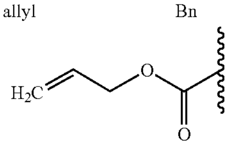
Alloc

Me

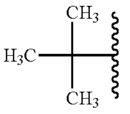
t-butyl

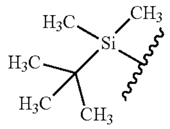
TBDMS

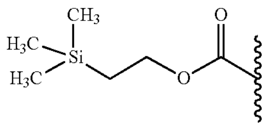
Teoc

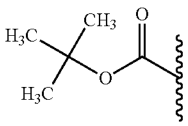
Boc

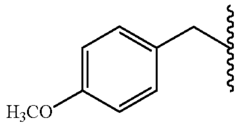
pMB

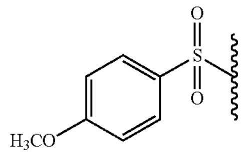
tosyl

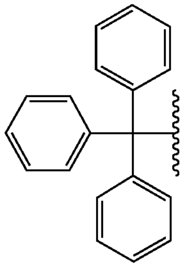
trityl

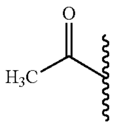
acetyl

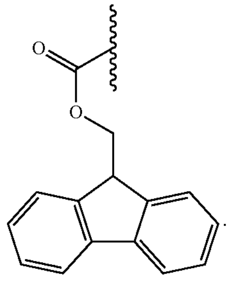
Fmoc

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

The synthetic descriptions and specific examples that follow are only intended for the purposes of illustration and are not to be construed as limiting in any manner to make compounds of the disclosure by other methods.

Example 1

General Methods 1.1: Chemical Synthesis General Methods:

$^1$H NMR spectra were recorded at 400 MHz or at 500 MHz. Chemical shifts are reported as δ-values in ppm relative to the $CDCl_3$ peak (δH 7.26), to the $CD_3OD$ peak (δH 3.31), and to the DMSO-$d_6$ peak (δH 2.54). Coupling constants (J) recorded in Hertz (Hz) and reported to the nearest 0.5 Hz.

All reactions were carried out with magnetic stirring and if air or moisture sensitive, in flame-dried or oven-dried glassware under nitrogen or argon. Syringes, used to transfer reagents and solvents, were purged with nitrogen or argon prior to use. Reaction temperatures other than room temperature were recorded as the bath temperature unless otherwise stated.

All solvents and reagents were used as commercially supplied, unless otherwise stated. $Et_2O$, THF, PhMe and $CH_2Cl_2$ were redistilled from Na-$Ph_2CO$, Na-$Ph_2CO$, Na and $CaH_2$ respectively.

Thin layer chromatography was performed on pre-coated aluminum backed silica gel F254 glass plates. The chromatogram was visualized under UV light and/or by staining using aqueous potassium permanganate or aqueous acidic vanillin followed by heating with a heat gun.

Flash column chromatography was performed using silica gel, particle size 40-63 1-1 m (eluents are given in parenthesis).

1.2: General Methods for Kinase Activity Assays

Compounds VKT-007, VKT-034, VKT-036, and VKT-511 were tested in 10-dose IC50 duplicate mode with a 3-fold serial dilution starting at 10 μM. Control compound, Staurosporine, was tested in 10-dose IC50 mode with 4-fold serial dilution starting at 20 μM. Reactions were carried out at 10 μM ATP.

Compound VKT-320 was tested in 10-dose IC50 triplicate mode with a 3-fold serial dilution starting at 9.827 μM. Control compound, Staurosporine, was tested in 10-dose IC50 mode with 4-fold serial dilution starting at 20 μM. Reactions were carried out at 10 μM ATP.

1.3: General Methods for Antiviral Activity Cell Culture Assays 1.3.1: Cell Culture and Virus Strains:

Human foreskin fibroblast (HFF) cells prepared from human foreskin tissue were obtained from the University of Alabama at Birmingham tissue procurement facility with approval from its IRB. The tissue was incubated at 4° C. for 4 h in Clinical Medium consisting of minimum essential media (MEM) with Earl's salts supplemented with 10% fetal bovine serum (FBS) (Hyclone, Inc. Logan UT), 1-glutamine, fungizone, and vancomycin. Tissue was then placed in phosphate buffered saline (PBS), minced, rinsed to remove the red blood cells, and resuspended in trypsin/EDTA solution. The tissue suspension was incubated at 37° C. and gently agitated to disperse the cells, which were collected by centrifugation. Cells were resuspended in 4 mL Clinical Medium and placed in a 25 $cm^2$ flask and incubated at 37° C. in a humidified $CO_2$ incubator for 24 h. The media was then replaced with fresh Clinical Medium and the cell growth was monitored daily until a confluent monolayer has formed. The HFF cells were then expanded through serial passages in standard growth medium of MEM with Earl's salts supplemented with 10% FBS, 1-glutamine, penicillin, and gentamycin. The cells were passaged routinely and used for assays at or below passage 10. Sanchez et al., 2003; Arend et al., 2017. COS7, C-33 A, Guinea Pig Lung, and Mouse embryo fibroblast cells were obtained from ATCC and maintained in standard growth medium of MEM with Earl's salts supplemented with 10% FBS, 1-glutamine, penicillin, and gentamycin.

Akata cells were kindly provided by John Sixbey (Louisiana State University, Baton Rouge, LA). BCBL-1 cells were obtained through the NIH AIDS Research and Reference Reagent Program, Division of AIDS, NIAID, NIH. Molt-3 cells were obtained from Scott Schmid at the Centers for Disease Control and Prevention, Atlanta, GA. Lymphocytes are maintained routinely in RPMI 1640 (Mediatech, Inc., Herndon, VA) with 10% FBS, 1-glutamine and antibiotics and passaged twice a week, as described previously. Keith et al., 2018; Prichard et al., 2011. The E-377 strain of Herpes Simplex Virus 1(HSV-1) was a gift of Jack Hill (Burroughs Wellcome). The Human Cytomegalovirus (HCMV) strain AD169, herpes simplex virus 2 (HSV-2) strain G, Adenovirus V5 strain (AdV5) strain Adenoid 75, guinea pig cytomegalovirus (GPCMV) strain 22122 and Mouse Cytomegalovirus (MCMV) strain Smith were obtained from the American Type Culture Collection (ATCC, Manassas, VA). The Copenhagen strain of vaccinia virus (VACV) was kindly provided by John W. Huggins (Department of Viral Therapeutics, Virology Division, United States Army Medical Research Institute of Infections Disease). The Varicella Zoster Virus (VZV) strain Ellen was obtained from the ATCC. Akata cells latently infected with Epstein Barr virus (EBV) were obtained from John Sixbey. The Z29 strain of Human Herpesvirus 6B (HHV-6B) was a gift of Scott Schmid at the Centers for Disease Control and Prevention, Atlanta GA. Human Herpesvirus 8 (HHV-8) was obtained as latently infected BCBL-1 cells through the NIH AIDS Research and Reference Reagent Program.

1.3.2: Antiviral Assays:

Each experiment that evaluated the antiviral activity of the compounds included both positive and negative control compounds to ensure the performance of each assay. Concurrent assessment of cytotoxicity was also performed for each study in the same cell line and with the same compound exposure. The antiviral assays were conducted using the below methodologies.

1.3.2.1: Primary Assay Format Consisting of Cytopathic Effect (CPE) Assays for HSV-1, HSV-2, VZV, HCMV, MCMV, GPCMV, and AdV:

Assays were performed in monolayers as described. Hartline et al., 2018. Briefly, cells were seeded in 384 well plates and incubated for 24 h to allow the formation of confluent monolayers. Dilutions of test drug were prepared directly in the plates and the monolayers infected at a predetermined multiplicity of infection (MOI) based on virus used. After incubation, cytopathology was determined by the addition of CellTiter-Glo (CTG) reagent. Concentrations of test compound sufficient to reduce CPE by 50% (EC50) or decrease cell viability by 50% (CC50) were interpolated using standard methods in Microsoft Excel. For MCMV, the assays were run in 96 well plates in mouse embryo fibroblast cells, with drug dilutions performed as above. After a 7 d incubation, DNA was extracted and a qPCR was run to calculate drug efficacy using primers 5'-TCA GCC ATC AAC TCT GCT ACC AAC-3', 5'-ATC TGA AAC AGC CGT ATA TCA TCT TG-3', and probe 5'-TTC TCT GTC AGC TAG CCA ATG ATA TCT TCG AGC-3'. Toxicity was measured using CTG as above. For GPCMV, the assays were run in 384 well plates in Guinea Pig Lung cells, with drug dilutions performed as above. After a 7 d incubation, DNA was extracted and a qPCR was run to calculate drug efficacy using primers 5'-GAGGTCGAGAAGCTGATATTGG-3', 5'-GTCTCTTCCTATGCGGGTTATC-3', and probe 5'-ACGTCACTTTGAGGGCCAACTGAT-3'. Toxicity was measured using CTG as above.

1.3.2.2: Primary Assay Format Consisting of Plaque Reduction Assays for HSV-1, HSV-2, and VZV:

Monolayers of HFF cells were prepared in six-well plates and incubated at 37° C. for 2 d to allow the cells to reach confluency. Media was then aspirated from the wells and 0.2 mL of virus-containing solution was added to each of three wells to yield 20-30 plaques in each well. The virus was allowed to adsorb to the cells for 1 h and the plates were agitated every 15 minutes. Compounds were diluted in assay media consisting of MEM with Earl's salts supplemented with 2% FBS, glutamine, penicillin, and gentamycin. Diluted drug was added to duplicate wells and the plates were incubated for various times, depending on the virus used. For HSV-1 and -2, the monolayers were then stained with 1% crystal violet in 20% methanol and the unbound dye removed by washing with dH20. For all other assays, the cell monolayer was stained with 1% Neutral Red solution for 4-6 h then the stain was aspirated and the cells were washed with PBS. For all assays, plaques were enumerated using a stereomicroscope and the concentration of compound that reduced plaque formation by 50% (EC50) was interpolated from the experimental data.

Secondary Assay Format Consisting of Yield Reduction Assays for HSV-1, HSV-2, HCMV, and AdV:

Monolayers of HFF cells were prepared in 96-well plates and incubated at 37° C. for 1 d to allow the cells to reach confluency. Media was then aspirated from the wells and cells infected at a high MOI. At 1 h following infection, the inocula were removed and the monolayers rinsed with fresh media. Compounds were then diluted in assay media consisting of MEM with Earl's salts supplemented with 2% FBS, 1-glutamine, penicillin, and gentamycin. Drug dilutions were added to the wells and the plates were incubated for various times, depending on the virus used and represents a single replication cycle for the virus. A duplicate set of dilutions were also performed but remained uninfected to serve as a cytotoxicity control and received equal compound exposure. Supernatants from each of the infected wells were subsequently titered using CTG in a TCID50 assay to quantify the progeny virus. For HCMV only, viral yield in the supernatants from the infected cells were titered using qPCR with HCMV primers 5'-AGG TCT TCA AGG AAC TCA GCA AGA-3', 5'-CGG CAA TCG GTT TGT AAA-3', and probe 5'-CCG TCA GCC ATT CTC TCG GC-3'. For cytotoxicity controls, cytotoxicity was assessed using CTG according to the manufacturer's suggested protocol. For all assays, the concentration of compound that reduced virus titer by 90% (EC90) was interpolated from the experimental data.

1.3.2.3: Secondary Assay for GPCMV:

Compounds that were positive in the CPE assay were confirmed in a similar assay in 96-well plates according to established laboratory protocols with the compounds added 1 h post infection to identify compounds that inhibit early stages of replication including adsorption and penetration. Genome copy number was determined by qPCR using primers 5'-GAG GTC GAG AAG CTG ATA TTG G-3', 5'-GTC TCT TCC TAT GCG GGT TAT C-3', and probe 5'-ACG TCA CTT TGA GGG CCA ACT GAT-3'.

1.3.2.4: Secondary Assay for MCMV:

Compounds that were positive in the CPE assay were confirmed in a similar assay in 96-well plates according to established laboratory protocols with the compounds added 1 h post infection to identify compounds that inhibit early stages of replication including adsorption and penetration. Additionally, 12 1:3 dilutions were done instead of 6 1:5 dilutions for added accuracy. Genome copy number was determined by qPCR using primers 5'-TCAGCCATCAACTCTGCTACCAAC-3', 5' ATCTGAAACAGCCGTATATCATCTTG-3', and probe 5'-TTCTCTGTCAGCTAGCCAATGATATCTTCGAGC-3'.

1.3.2.5: Primary Assay for EBV, HHV-6B, and HHV-8:

Assays for EBV, HHV-6B and HHV-8 were performed by methods we reported previously. Keith et al., 2018. For EBV assays, Akata cells were induced to undergo a lytic infection with 50 μg/mL of a goat anti-human IgG antibody. Experimental compounds were diluted within plates; the cells were added and incubated for 72 h. For HHV-6 assays, compounds were serially diluted in plates then uninfected Molt-3 cells were added to each well. Infection was initiated by adding HHV-6B infected Molt-3 cells, at a ratio of approximately 1 infected cell for every 10 uninfected cells. Assay plates were incubated for seven days at 37° C. Assays for HHV-8 were performed in BCBL-1 cells. Similar plates were initiated without virus induction/addition and used for measuring cytotoxicity by the addition of CTG. For all assays, the replication of the virus was assessed by the quantification of viral DNA. For EBV, primers 5'-CCC AGG AGT CCC AGT CA-3' and 5'-CAG TTC CTC GCCT-TAGGTTG-3 amplified a fragment corresponding to coordinates 96802-97234 in EBV genome (AJ507799). For HHV-8, 5'-TTC CCC AGA TAC ACG ACA GAA TC-3', reverse primer 5'-CGG AGC GCA GGC TAC CT-3', and probe 5'-(FAM) CCT ACG TGT TCG AC (TAMRA)-3'. Plasmid pMP218 containing a DNA sequences corresponding to nucleotides 14120-14182 (AF148805.2) was used to provide absolute quantification of viral DNA. For HHV-6B, 5'-GTT AGG GTA TAC CGA TGT GCG TGA T-3' 5'-TAC AGA TAC GGA GGC AAT AGA TTC G-3' and 5'-(FAM) TCC GAA ACA ACT GTC TGA CTG GCA AAA-3' were used to quantify virus DNA. Compound concentrations sufficient to reduce genome copy number by 50% were calculated from experimental data as well as compound cytotoxicity. Secondary assays are performed similarly, with the addition of 50 μg/ml of goat anti-human-IgG antibody to cells (EBV), initiation of infection by adding infected cells to uninfected cells (HHV-6B) or induction of HHV-8 in BCBL-1 cells—all performed and incubated for 1 h prior to adding the cells to plates containing compounds at 12 concentrations resulting from threefold dilution of the original stock.

1.3.2.6: Primary Assay for HPV:

An HPV11 replicon assay was developed and expresses the essential E1 and E2 proteins from the native promoter. The E2 origin binding protein interacts with the virus origin of replication and recruits the E1 replicative helicase which unwinds the DNA and helps to recruit the cellular DNA replication machinery (including DNA polymerases, type I and type II topoisomerases, DNA ligase, single-stranded DNA binding proteins, proliferating cell nuclear antigen). The replication complex then drives the amplification of the replicon which can be assessed by the expression of a destabilized NanoLuc reporter gene carried on the replicon. In this assay, the replicon (pMP619) is transfected into C-33 A cells grown as monolayers in 384-well plates. At 48 h post transfection, the enzymatic activity of the destabilized NanoLuc reporter is assessed with NanoGlo reagent. The reference compound for this assay is PMEG and its EC50 value is within the prescribed range of 2 μM-9.2 μM and is similar to a compound reported previously. Beadle et al., 2016.

1.4: General Methods for Metabolic Stability Assay:

1.4.1: Preparation of Reagents 1.4.1.1: Preparation of Potassium Phosphate Buffer, 50 mM (pH 7.4):

Potassium phosphate buffer (Kphos) was prepared by adding 0.647 g potassium phosphate monobasic ($KH_2PO_4$) and 3.527 g potassium phosphate dibasic ($K_2HPO_4$) to 400 mL of Milli-Q water. pH of the buffer was adjusted to 7.4 and volume was made up to 500 mL.

1.4.1.2: Preparation of Microsomes:

Microsomes (20 mg/mL) were diluted in Kphos buffer to prepare a concentration of 0.714 mg/mL.

1.4.1.3: Preparation of Test Compounds:

Stock solutions of the test compounds were prepared in DMSO at a concentration of 1 mM.

1.4.1.4: Preparation of NADPH Solution:

A stock solution of 3.33 mM NADPH (3.33X) was prepared by dissolving appropriate amount of NADPH in Kphos buffer.

1.4.2: Assay Conditions:

| | |
|---|---|
| Total Incubation volume | 100 μL |
| Compound concentration | 1 μM |
| Protein Concentration | 0.5 mg/mL (0.25 mg/mL for positive |
| NADPH | 1 mM |
| Final DMSO contain | 0.1% |
| Number of replicates | 2 |
| Time points | 0 min and 60 min |

1.4.3: Assay Format:

A microsomal mix (microsomes and Kphos buffer) was prepared at concentration of 0.714 mg/mL (for test compound) and 0.357 mg/mL (for positive control) in 2 mL tubes. To this microsomal mix 1.42 μL (1 mM) of test compound and positive control were spiked, from this mix 70 μL was transferred to 96 well plate and pre-incubated at 37° C. for 5 min. After pre-incubation zero min time point reaction was stopped using 100 μL of ice-cold acetonitrile containing internal standard, to this 30 μL of NADPH (3.33 mM in Kphos buffer) was added. For 60 min time point reaction was initiated by addition of 30 μL of NADPH (3.33 mM in Kphos buffer) and incubated at 37° C. for 60 min, incubation reaction was stopped with 100 μL of ice-cold acetonitrile containing internal standard (glipizide). The plates were centrifuged at 4000 RPM for 15 min and 100 μL aliquots were submitted for analysis by LC-MS/MS.

1.4.4: Bio-Analysis:

Samples were monitored for parent compound disappearance in MRM mode using LC-MS/MS. The LC-MS/MS conditions and MRM chromatogram will be provided as per client request.

1.4.5: Data Analysis:

The peak area ratios of analyte versus internal standard were used to calculate the % remaining at the end of 60 minutes in presence NADPH.

Example 2

Synthesis and Characterization of Representative Compounds 2.1 Experimental

Unless otherwise noted, reagents and solvents were used as received from commercial suppliers. Nuclear magnetic resonance spectra were obtained on a Bruker AC 300 a Bruker AV 300 spectrometer, or on a Bruker AV 400 spectrometer. Spectra are given in ppm (δ) and coupling constants, J, are reported in Hertz. Tetramethyl silane was used as an internal standard for proton spectra and the solvent peak was used as the reference peak for carbon spectra. Mass spectra and LCMS analyses were obtained on a Shimadzu LC-20AD, ESI and APCI, single quadrupole mass spectrometer. Flash chromatography often utilized the Isco Combiflash Companion MPLC system. The method used on HPLC's are described below.

2.1.1 HPLC Method

Column: Eclipse Plus C18, 100×4.6 mm, 3.5 μm

Mobile Phase A: 0.05% TFA in water

Mobile Phase B: 0.05% TFA in Acetonitrile

TABLE 1

| Method A Gradient | | | |
|---|---|---|---|
| Time (min) | Flow (mL/min) | % A | % B |
| 0 | 1.0 | 95.0 | 5.0 |
| 2 | 1.0 | 95.0 | 5.0 |
| 7 | 1.0 | 30.0 | 70.0 |
| 10 | 1.0 | 5.0 | 95.0 |
| 12 | 1.0 | 5.0 | 95.0 |
| 12.1 | 1.0 | 95.0 | 5.0 |
| 15 | 1.0 | 95.0 | 5.0 |

2.1.2 Experimental Procedures

The following compounds were synthesized and characterized:

Synthesis of VKT-001 and VKT-002:

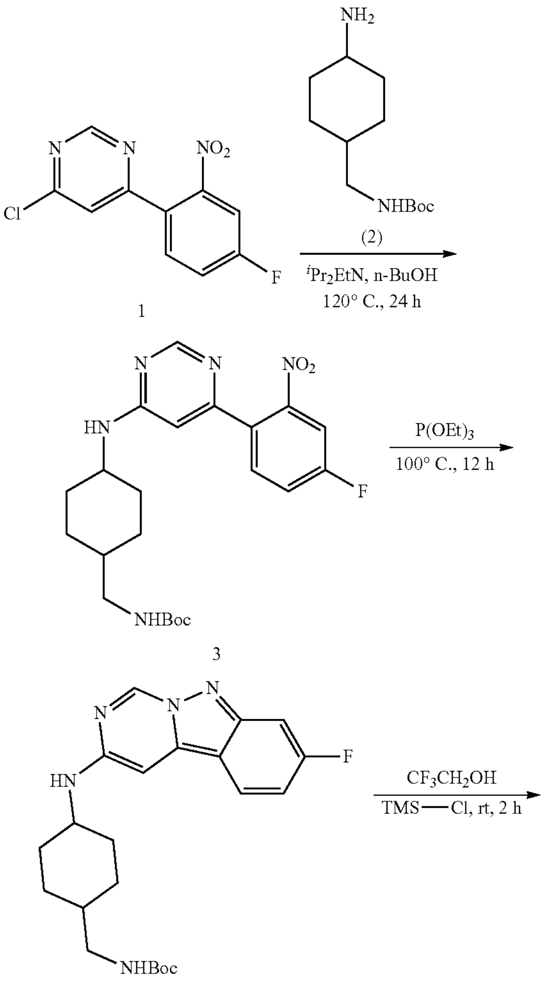

1

3

VKT-001

-continued

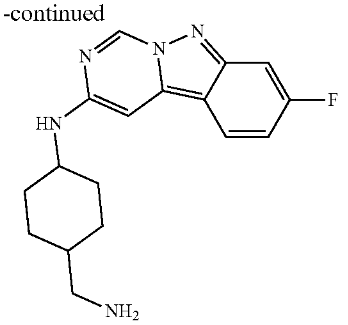

VKT-002

Synthesis of 1 (Intermediate 4):

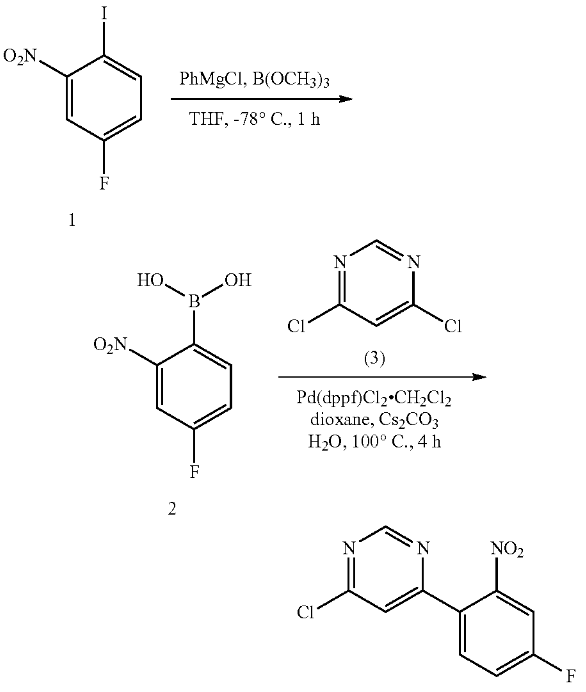

1

2

Intermediate 4

Preparation of 2:

To a stirred solution of 1 (100 g, 374 mmol) in dry THF (1000 mL), placed in a 3 neck round bottom flask, under $N_2$ atmosphere at −60° C., was added PhMgCl (2.0 M in THF, 374 mL, 749 mmol) dropwise over a period of 15 min. The I—Mg exchange was complete within 5 min (monitored by TLC of reaction aliquots). Trimethyl borate (115 g, 1123 mmol) was added dropwise over a period of 5 min. The reaction mixture was stirred at −60° C. for 30 min. The reaction mixture was gradually warmed to −20° C., and then quenched with 2 M aq. HCl (500 mL) at −20° C. The reaction mixture was gradually warmed to room temperature and extracted with ethyl acetate (3×500 mL). The combined organic extracts were washed with brine (100 mL), dried over anhydrous $Na_2SO_4$, filtered and concentrated under vacuum to obtain the crude product. The crude product was purified by silica-gel chromatography using 25-30% EtOAc: Hexanes. The fractions containing the product were combined and concentrated under vacuum to obtain 2 (36.0 g, 51% yield) as a brown liquid. $^1H$ NMR (400 MHz, MeOD): δ: 7.91-7.89 (m, 1H), 7.49-7.45 (m, 2H).

Preparation of Intermediate 4:

To a stirred solution of 2 (36.0 g, 195 mmol) in 1,4-dioxane (400 mL) at rt under $N_2$ atmosphere, was added 3 (28.0 g, 195 mmol), $Cs_2CO_3$ (36.0 g, 391 mmol), Pd(dppf) $Cl_2 \cdot CH_2Cl_2$ (7.98 g, 9.78 mmol) and $H_2O$ (100 mL). The reaction mixture was degassed with Ar(g) for 10 min, then gradually heated to 100° C. and stirred for 4 h. The reaction mixture was cooled to room temperature, filtered through a celite bed and washed with ethyl acetate (250 mL). The filtrate was concentrated, diluted with water (250 mL) and extracted with EtOAc (2×250 mL). The combined organic extracts were washed with brine solution (100 mL), dried over anhydrous $Na_2SO_4$ and concentrated under reduced pressure to obtain the crude product. The crude compound was purified by silica-gel column chromatography using 5-6% EtOAc:Hexanes. The fractions containing the product were combined for concentration to obtain Intermediate 4 (10.0 g, 20% yield) as an off-white solid. $^1H$ NMR (400 MHz, DMSO-$d_6$): δ: 9.07 (d, J=1.2 Hz, 1H), 8.22 (d, J=1.2 Hz, 1H), 8.12 (dd, J=8.4 and 2.4 Hz, 1H), 8.00 (dd, J=8.8 and 5.6 Hz, 1H), 7.81 (dt, J=8.4 and 2.8 Hz, 10.8 Hz, 1H).

Preparation of 3:

To a suspension of 1 (Intermediate 4) (750 mg, 2.96 mmol) in anhydrous n-butanol (30 mL), at room temperature under $N_2$ atmosphere, was added 2 (811 mg, 3.55 mmol) followed with N,N-diisopropylethylamine (1.14 g, 8.89 mmol), and the reaction mixture was stirred at 120° C. for 24 h. The reaction mixture was cooled to room temperature, and the solvent was removed under reduced pressure to obtain the crude product. The crude product was purified by silica-gel column chromatography using 15% $CH_3OH$ (0.5% $NH_3$):$CH_2Cl_2$. The fractions containing the product were combined for concentration to obtain 3 (535 mg, 40% yield) as a brown gummy solid. $^1H$ NMR (400 MHz, DMSO-$d_6$): δ: 8.34 (s, 1H), 7.96 (dd, J=8.4 Hz and J=2.4 Hz, 1H), 7.75-7.69 (m, 1H), 7.68-7.55 (m, 1H), 7.54-7.52 (m, 1H), 6.82-6.80 (m, 1H), 6.69-6.61 (m, 1H), 3.91-3.81 (m, 1H), 3.35-3.31 (m, 2H), 2.80-2.67 (m, 2H), 1.97-1.95 (m, 3H), 1.73-1.70 (m, 2H), 1.37-1.23 (m, 9H), 1.19-1.00 (m, 2H). MS (ESI+APCI; multimode): 446 $[M+H]^+$.

Preparation of VKT-001:

A solution of 3 (250 mg, 0.56 mmol) in $P(OEt)_3$ (20 mL) at room temperature under $N_2$ atmosphere, was sonicated for 10 min, and the mixture was gradually heated to 100° C. and stirred for 12 h. The reaction mixture was cooled to room temperature and the solvent was concentrated by vacuum distillation to obtain the crude product. The crude product was purified by silica-gel column chromatography using 20% $CH_3OH$ (0.5% $NH_3$):$CH_2Cl_2$. The fractions containing the product were combined for concentration to obtain the product, which was impure. The product was triturated with a mixture of $CH_3CN$ (20 mL), MTBE (20 mL), and sonicated for 15 min, whereupon the product precipitated. The precipitated product was collected by filtration under vacuum, and washed with pentane (20 mL). The product was further dried by lyophilization for 12 h to afford VKT-001 (80.0 mg, 34% yield) as a yellow solid. $^1H$ NMR (400 MHz, DMSO-$d_6$): δ: 9.36 (s, 1H), 8.14 (t, J=6.0 Hz, 1H), 7.15-7.13 (m, 1H), 7.08-7.01 (m, 2H), 6.84-6.79 (m, 1H), 6.77-6.75 (m, 1H), 4.06-3.98 (m, 1H), 3.52-3.49 (m, 1H), 2.84-2.80 (m, 2H), 2.03-2.00 (m, 2H), 1.76-1.74 (m, 2H), 1.38 (s, 9H), 1.25-1.23 (m, 2H), 1.05-1.02 (m, 2H). MS (ESI+APCI; multimode): 414 $[M+H]^+$. HPLC: 97.8 (% of AUC).

Preparation of VKT-002:

To a suspension of VKT-001 (250 mg, 0.60 mmol) in anhydrous $CF_3CH_2OH$ (30 mL), at room temperature under $N_2$ atmosphere, was added TMSCl (131 mg, 1.21 mmol), and the mixture was stirred at room temperature for 12 h. After completion of reaction, the solvent was concentrated under vacuum to obtain the crude product. The crude product was purified by silica-gel column chromatography using 20% $CH_3OH$ (0.5% $NH_3$):$CH_2Cl_2$. The fractions containing the product were combined for concentration to obtain to obtain the crude product. The crude product was triturated with $CH_3CN$ (20 mL) and MTBE (20 mL), and sonicated for 15 min, whereupon the product precipitated. The precipitated product was collected by filtration under vacuum, washed with pentane (20 mL) and dried under vacuum. The product was further dried by lyophilization for 12 h to afford VKT-002 (70.0 mg, 36% yield) as a yellow solid. $^1H$ NMR (400 MHz, DMSO-$d_6$): δ: 9.37 (s, 1H), 8.15-8.12 (m, 1H), 7.15-7.07 (m, 3H), 6.76 (t, J=8.4 Hz, 1H), 3.50-3.31 (m, 2H), 2.42-2.41 (m, 2H), 2.04-2.01 (m, 2H), 1.85-1.77 (m, 2H), 1.30-1.22 (m, 4H), 1.06-1.00 (m, 2H). MS (ESI+APCI; multimode): 314 $[M+H]^+$. HPLC: 97.4 (% of AUC).

Synthesis of VKT-005:

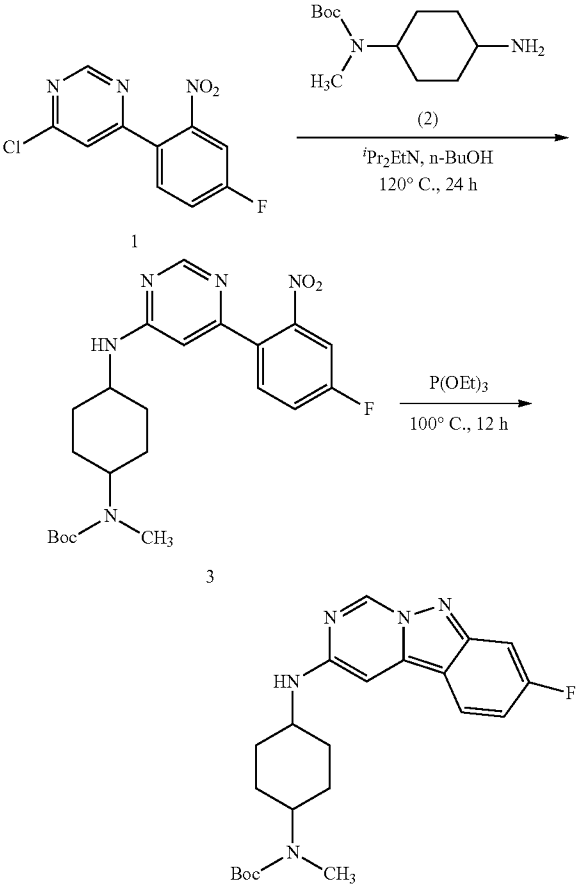

1

3

VKT-005

Preparation of 3:

To a suspension of 1 (250 mg, 0.98 mmol) in anhydrous n-butanol (10 mL), at room temperature, under $N_2$ atmosphere, was added 2 (270 mg, 1.18 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 5% $CH_3OH$ (0.5% $NH_3$): $CH_2Cl_2$ to afford 3 (110 mg, 25% yield) as a brown gummy solid. MS (ESI+APCI; multimode): 446 $[M+H]^+$.

Preparation of VKT-005:

A solution of 3 (110 mg, 0.24 mmol) in $P(OEt)_3$ (10 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 10% $CH_3OH$ (0.5% $NH_3$):$CH_2Cl_2$ to obtain the crude product. The crude product was triturated with $CH_3CN$ (10 mL) and $H_2O$ (10 mL), the mixture was sonicated for 15 min, whereupon the product precipitated. The precipitated product was collected by filtration under vacuum, washed with MTBE (20 mL) and pentane (20 mL) and dried under vacuum. The product was further dried by lyophilization for 12 h to afford VKT-005 (62.0 mg, 58% yield) as a yellow solid. $^1H$ NMR (400 MHz, DMSO-$d_6$): δ: 9.42 (d, J=1.2 Hz, 1H), 8.12 (dd, J=8.8 Hz and J=6.0 Hz, 1H), 7.27 (d, J=7.6 Hz, 1H), 7.18-7.15 (m, 2H), 6.85-6.80 (m, 1H), 4.09-3.98 (m, 1H), 2.73 (s, 3H), 1.96-1.90 (m, 2H), 1.89-1.82 (m, 2H), 1.68-1.61 (m, 2H), 1.40 (s, 9H), 1.39-1.38 (m, 2H), 1.25-1.20 (m, 1H). MS (ESI+APCI; multimode): 414 $[M+H]^+$. HPLC: 93.5 (% of AUC).

Synthesis of VKT-006:

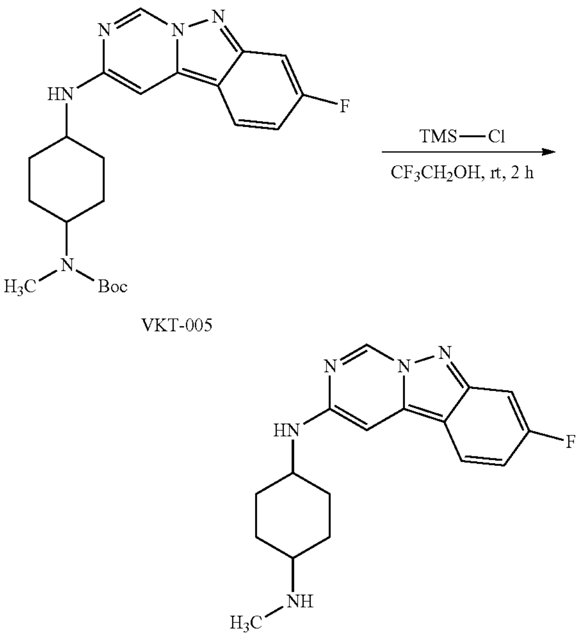

VKT-005

VKT-006

Preparation of VKT-006:

To a suspension of VKT-005 (200 mg, 0.48 mmol) in anhydrous $CF_3CH_2OH$ (10 mL), at room temperature, under $N_2$ atmosphere, was added TMS-Cl (105 mg, 0.96 mmol). The reaction mixture was stirred at room temperature for 2 h. After completion of reaction, basic resin was added (pH=8), filtered, and the filtrate was concentrated under vacuum to obtain the crude product. The crude product was purified by silica-gel column chromatography using 25% $CH_3OH$ (0.5% $NH_3$):$CH_2Cl_2$ to obtain the crude product.

The crude product was triturated with $CH_3CN$ (20 mL), and sonicated for 15 min, whereupon the product precipitated. The precipitated product was collected by filtration under vacuum, washed with MTBE (25 mL) and pentane (20 mL) and dried under vacuum. The product was further dried by lyophilization for 12 h to afford VKT-006 (80.0 mg, 52% yield) as a yellow solid. $^1H$ NMR (400 MHz, DMSO-$d_6$): δ: 9.37 (d, J=1.2 Hz, 1H), 8.12 (dd, J=8.8 Hz and J=5.6 Hz, 1H), 7.14 (dd, J=11.2 Hz and J=2.0 Hz, 1H), 7.08 (d, J=1.2 Hz, 1H), 7.07 (s, 1H), 6.79-6.73 (m, 1H), 3.75-3.70 (m, 1H), 2.26 (s, 3H), 1.74-1.55 (m, 10H). MS (ESI+APCI; multimode): 314 $[M+H]^+$. HPLC: 97.4 (% of AUC).

Synthesis of VKT-007:

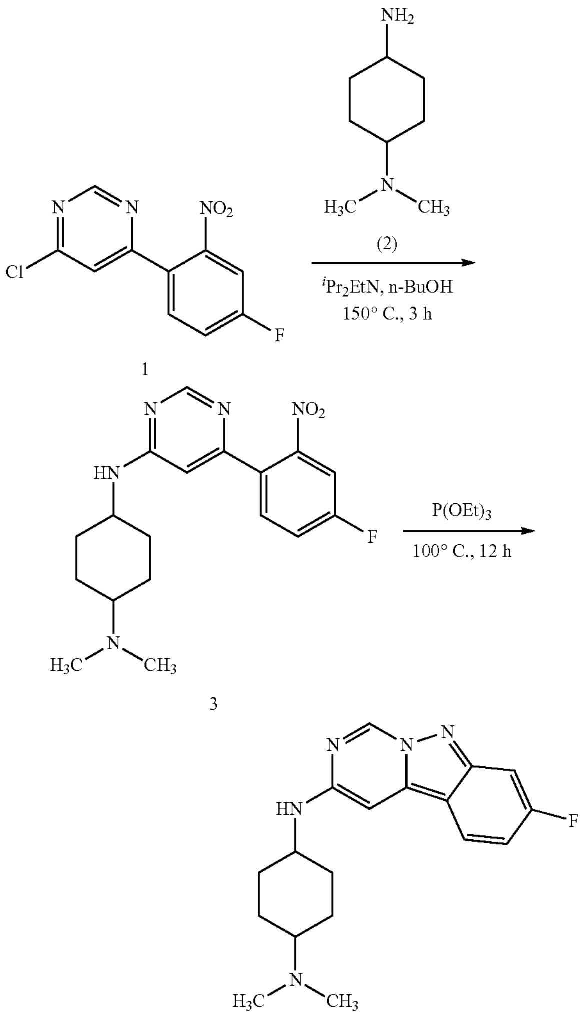

1

3

VKT-007

Preparation of 3:

To a suspension of 1 (250 mg, 0.98 mmol) in anhydrous n-butanol (10 mL), at room temperature, under $N_2$ atmosphere, was added 2 (281 mg, 1.97 mmol) followed with N,N-diisopropylethylamine (382 mg, 2.96 mmol). The reaction mixture was gradually heated to 150° C. and stirred for 3 h. The reaction mixture was cooled to room temperature, and solvent was concentrated under vacuum to obtain the crude product. The crude product was purified by silica-gel column chromatography using 10% $CH_3OH$ (0.5% $NH_3$): $CH_2Cl_2$ to afford 3 (250 mg, 84% yield) as a brown gummy solid. $^1$H NMR (400 MHz, DMSO-$d_6$): δ: 8.36 (s, 1H), 7.98 (dd, J=8.4 Hz and J=2.4 Hz, 1H), 7.71-7.70 (m, 1H), 7.69-7.68 (m, 1H), 7.61-7.59 (m, 1H), 6.76-6.66 (m, 1H), 3.88-3.81 (m, 1H), 2.49-2.38 (m, 1H), 2.33 (s, 3H), 2.32 (s, 3H), 2.10-2.02 (m, 1H), 1.91-1.85 (m, 1H), 1.80-1.65 (m, 2H), 1.64-1.55 (m, 2H), 1.44-1.22 (m, 2H). MS (ESI+APCI; multimode): 360 $[M+H]^+$.

Preparation of VKT-007:

A solution of 3 (200 mg, 0.55 mmol) in $P(OEt)_3$ (10 mL), at room temperature, under $N_2$ atmosphere was sonicated for 10 min. The reaction mixture was gradually heated to 100° C. and stirred for 12 h. The reaction mixture was cooled to room temperature, and solvent was concentrated under vacuum to obtain the crude product. The crude product was purified by C-18 column chromatography using 5% $CH_3CN$:$H_2O$ followed by silica-gel column chromatography using 30% $CH_3OH$ (0.5% $NH_3$):$CH_2Cl_2$ to obtain the crude product. The crude product was triturated with $CH_3CN$ (20 mL), MTBE (20 mL), and sonicated for 10 min, whereupon the product precipitated. The precipitated product was collected by filtration under vacuum, washed with pentane (30 mL) and dried under vacuum. The product was further dried by lyophilization for 12 h to afford racemic VKT-007 (100 mg, 55% yield) as yellow solid. $^1$H NMR (400 MHz, DMSO-$d_6$): δ: 9.39 (dd, J=6.4 Hz and J=1.2 Hz, 1H, 1H), 8.15-8.10 (m, 1H), 7.20-7.09 (m, 3H), 6.80-6.75 (m, 1H), 4.10-3.84 (m, 1H), 3.60-3.54 (m, 1H), 2.34 (s, 3H), 2.33 (s, 3H), 2.09-2.07 (m, 1H), 1.90-1.85 (m, 1H), 1.82-1.70 (m, 1H), 1.66-1.61 (m, 1H), 1.60-1.51 (m, 2H), 1.40-1.29 (m, 2H). MS (ESI+APCI; multimode): 328 $[M+H]^+$. HPLC: 97.2% [(% of AUC, RT-6.19 min (42.94%) & 6.31 min (54.34%)].

Synthesis of VKT-008:

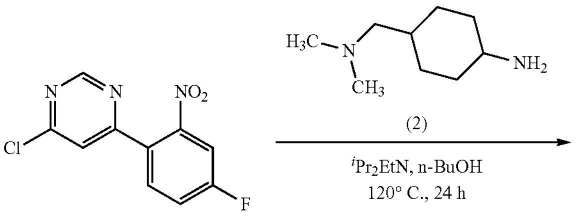

1

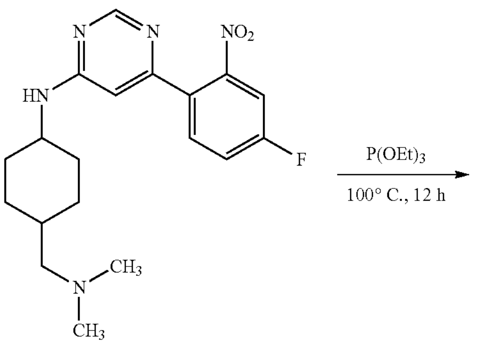

3

-continued

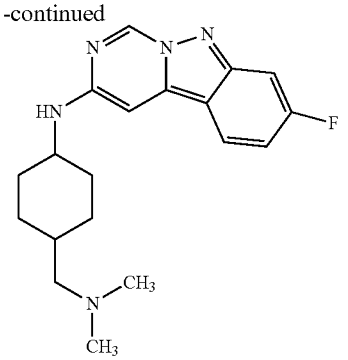

VKT-008

Preparation of 3:

To a suspension of 1 (500 mg, 1.97 mmol) in anhydrous n-butanol (20 mL), at room temperature, under $N_2$ atmosphere, was added 2 (617 mg, 3.95 mmol) followed with N,N-diisopropylethylamine (765 mg, 5.92 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 25% $CH_3OH$ (0.5% $NH_3$): $CH_2Cl_2$ to afford 3 (125 mg, 16% yield) as a brown gummy solid. $^1$H NMR (400 MHz, DMSO-$d_6$): δ: 9.75-9.60 (m, 1H), 8.91-8.81 (m, 1H), 8.41-8.36 (m, 1H), 7.97 (dd, J=7.2 Hz and J=2.4 Hz, 1H), 7.89-7.75 (m, 2H), 7.74-7.70 (m, 2H), 7.68-7.04 (m, 2H), 6.89-6.80 (m, 1H), 6.67-6.64 (m, 1H), 4.12-4.10 (m, 1H), 3.91-3.81 (m, 1H), 3.62-3.58 (m, 2H), 3.21-3.10 (m, 2H), 2.99-2.90 (m, 2H), 2.75-2.70 (m, 8H), 2.00-1.84 (m, 2H), 1.75-1.68 (m, 2H), 1.64-1.61 (m, 2H), 1.47-1.30 (m, 2H), 1.34-1.25 (m, 2H), 1.20-1.10 (m, 2H). MS (ESI+APCI; multimode): 374 $[M+H]^+$.

Preparation of VKT-008:

A solution of 3 (125 mg, 0.33 mmol) in $P(OEt)_3$ (10 mL), at room temperature, under $N_2$ atmosphere, was sonicated for 15 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 30% $CH_3OH$ (0.5% $NH_3$):$CH_2Cl_2$ to obtain the crude product. The crude product was triturated with $CH_3CN$ (10 mL) and $H_2O$ (10 mL), sonicated for 15 min, whereupon the product precipitated. The precipitated product was collected by filtration under vacuum, washed with MTBE (20 mL) and pentane (20 mL) and dried under vacuum. The product was further dried by lyophilization for 12 h to afford racemic VKT-008 (70.0 mg, 54% yield) as a yellow solid. $^1$H NMR (400 MHz, DMSO-$d_6$): δ: 9.98 (brs, 1H), 9.41-9.38 (m, 1H), 8.15-8.11 (m, 1H), 7.34-7.09 (m, 8H), 6.80-6.77 (m, 1H), 4.03-3.90 (m, 2H), 2.95-2.85 (m, 2H), 2.80-2.70 (m, 10H), 2.05-2.03 (m, 1H), 1.92-1.89 (m, 3H), 1.74-1.72 (m, 5H), 1.69-1.63 (m, 1H), 1.53-1.41 (m, 2H), 1.34-1.21 (m, 2H), 1.19-1.10 (m, 2H). $^1$H NMR (400 MHz, MeOD): δ: 9.04 (dd, J=8.8 Hz and J=1.2 Hz, 2H), 7.94-7.91 (m, 2H), 6.97-6.90 (m, 4H), 6.68-6.66 (m, 2H), 3.92-3.82 (m, 2H), 3.67-3.60 (m, 1H), 3.03-2.96 (m, 4H), 2.84-2.81 (m, 13H), 2.09-1.86 (m, 8H), 1.82-1.76 (m, 2H), 1.73-1.63 (m, 2H), 1.47-1.30 (m, 2H), 1.21-1.14 (m, 4H). MS (ESI+APCI; multimode): 342 $[M+H]^+$. HPLC: 90.5 (51.28:39.31) (% of AUC, RT: 6.53 min & 6.63 min).

Synthesis of VKT-009-a:

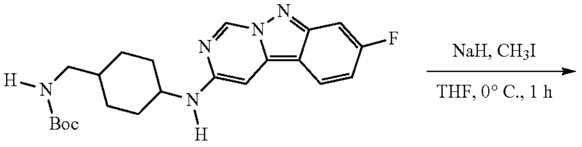

VKT-001

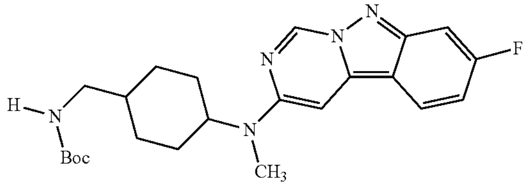

VKT-009-a

Preparation of VKT-009-a:

To a suspension of VKT-001 (250 mg, 0.60 mmol) in anhydrous THF (10 ml), at 0° C. under $N_2$ atmosphere, was added NaH (50%, 33.0 mg, 1.45 mmol) and stirred at 0° C. for 10 min. Methyl iodide (85.0 mg, 0.60 mmol) was added at same temperature. The reaction mixture was stirred at 0° C. for 1 h. The reaction mixture was cooled to 0° C., quenched with ice cold water (5 mL), diluted with water (20 mL), and extracted with EtOAc (2×50 mL). The combined organic extracts were washed with brine (20 mL), dried over anhydrous $Na_2SO_4$, filtered and concentrated under vacuum to obtain the crude product. The crude product was purified by silica-gel column chromatography using 40% EtOAc: Hexanes to obtain the crude product. The crude product was triturated with $CH_3CN$ (10 mL) and $H_2O$ (10 mL), sonicated for 15 min, whereupon the product precipitated. The precipitated product was collected by filtration under vacuum, washed with pentane (20 mL) and dried under vacuum (lyophilization) to afford VKT-009-a (70.0 mg, 27% yield) as a yellow solid. $^1H$ NMR (400 MHz, DMSO-$d_6$): δ: 9.46 (d, J=0.8 Hz, 1H), 8.20 (dd, J=8.8 Hz and J=5.6 Hz, 1H), 7.30 (s, 1H), 7.18 (dd, J=7.2 Hz and J=2.4 Hz, 1H), 6.91 (t, J=5.6 Hz, 1H), 6.83-6.78 (m, 1H), 4.46-4.40 (m, 1H), 2.95 (s, 3H), 2.84-2.80 (m, 2H), 1.81-1.78 (m, 2H), 1.68-1.60 (m, 4H), 1.57-1.54 (m, 10H), 1.40-1.12 (m, 2H). MS (ESI+APCI; multimode): 428 $[M+H]^+$. HPLC: 95.0 (% of AUC).

Synthesis of VKT-009-b:

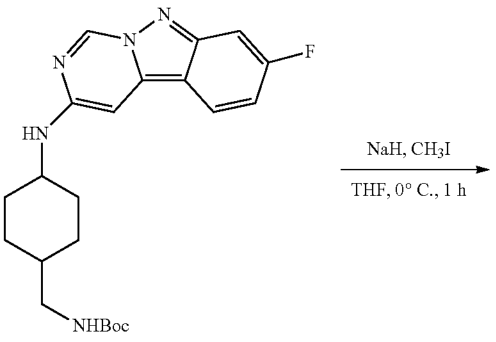

VKT-001

-continued

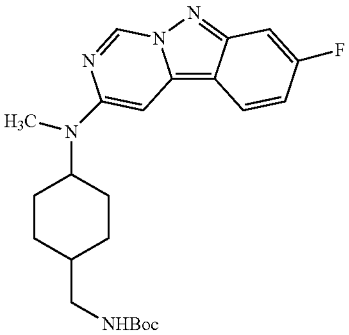

VKT-009-a

+

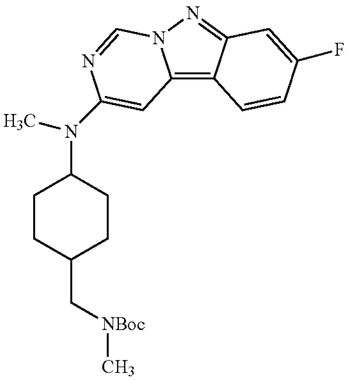

VKT-009-b

Preparation of VKT-009-b:

To a suspension of VKT-001 (250 mg, 0.60 mmol) in anhydrous THF (10 ml), at 0° C. under $N_2$ atmosphere, was added NaH (50%, 33.0 mg, 1.45 mmol) and stirred at 0° C. for 10 min. Methyl iodide (85.0 mg, 0.60 mmol) was added at same temperature. The reaction mixture was stirred at 0° C. for 1 h. The reaction mixture was cooled to 0° C., quenched with ice cold water (5 mL), diluted with water (20 mL), and extracted with EtOAc (2×50 mL). The combined organic extracts were washed with brine (20 mL), dried over anhydrous $Na_2SO_4$, filtered and concentrated under vacuum to obtain the crude product. The crude product was purified by silica-gel column chromatography using 40% EtOAc: Hexanes to obtain the crude products VKT-009a and VKT-009-b. The crude product was triturated with $CH_3CN$ (10 mL) and $H_2O$ (10 mL), sonicated for 15 min to afford VKT-009-a. The filtrate was concentrated, and the crude product was triturated with $CH_3CN$ (20 mL) and $H_2O$ (10 mL), sonicated for 25 min, and heated at 50° C. for 30 min, gradually warmed to room temperature for 2 h, whereupon the product precipitated. The precipitated product was collected by filtration under vacuum, washed with MTBE (30 mL), pentane (20 mL) and dried under vacuum (lyophilization) to afford VKT-009-b (65.0 mg, 24% yield) as a yellow solid. IN-AAR-AA-83-10: $^1H$ NMR (400 MHz, DMSO-$d_6$): δ: 9.45 (d, J=1.2 Hz, 1H), 8.20 (dd, J=8.8 Hz and J=6.0 Hz, 1H), 7.30 (s, 1H), 7.17 (dd, J=11.2 Hz and J=2.0 Hz, 1H), 6.83-6.78 (m, 1H), 4.51-4.45 (m, 1H), 3.06 (d, J=7.2 Hz, 2H), 2.96 (s, 3H), 2.79 (s, 3H), 1.74-1.71 (m, 2H), 1.68-1.63 (m, 2H), 1.60-1.57 (m, 2H), 1.48-1.40 (m, TOH), 1.24-1.22 (m, 1H), 1.17-1.12 (m, 1H). MS (ESI+APCI; multimode): 442 $[M+H]^+$. HPLC: 90.1 (% of AUC).

Synthesis of VKT-011:

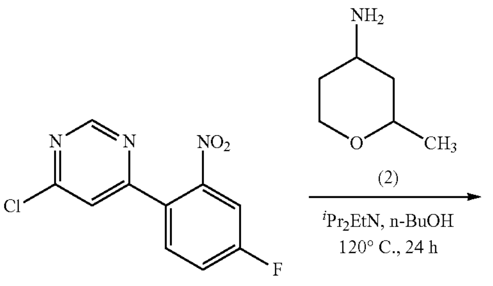

1

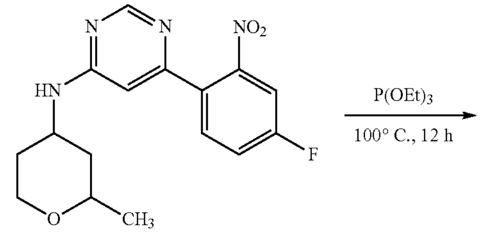

3

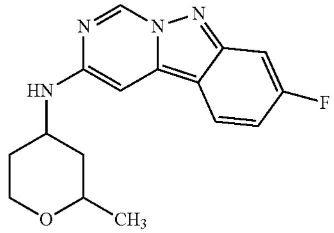

VKT-011

Preparation of 3:

To a suspension of 1 (500 mg, 1.97 mmol) in anhydrous n-butanol (20 mL), at room temperature, under $N_2$ atmosphere, was added 2 (455 mg, 3.95 mmol) followed with N,N-diisopropylethylamine (765 mg, 5.92 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 10% $CH_3OH$ (0.5% $NH_3$): $CH_2Cl_2$ to afford 3 (260 mg, 39% yield) as a brown gummy solid. $^1H$ NMR (400 MHz, DMSO-$d_6$): δ: 8.39 (s, 1H), 7.99-7.96 (m, 1H), 7.77 (d, J=6.8 Hz, 2H), 7.71-7.66 (m, 1H), 6.79 (brs, 1H), 3.76-3.70 (m, 2H), 3.40-3.35 (m, 1H), 1.82-1.72 (m, 2H), 1.63-1.59 (m, 2H), 1.52-1.51 (m, 1H), 1.50-1.48 (m, 3H). MS (ESI+APCI; multimode): 333 $[M+H]^+$.

Preparation of VKT-011:

A solution of 3 (260 mg, 0.78 mmol) in $P(OEt)_3$ (20 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography (twice) using 25% $CH_3OH$ (0.5% $NH_3$):$CH_2Cl_2$ to obtain the crude product. The crude product was triturated with $CH_3CN$ (20 mL), and sonicated for 15 min, whereupon the product precipitated. The precipitated product was collected by filtration under vacuum, washed with pentane (20 mL) and dried under vacuum. The product was further dried by lyophilization for 12 h to afford VKT-011 (85.0 mg, 36% yield) as a yellow solid. $^1H$ NMR (400 MHz, DMSO-$d_6$): δ: 9.43-9.41 (m, 1H), 8.14 (dd, J=8.8 Hz and J=5.6 Hz, 1H), 7.40 (d, J=6.8 Hz, 1H), 7.19-7.13 (m, 2H), 6.81-6.76 (m, 1H), 4.09-4.07 (m, 1H), 3.89-3.81 (m, 1H), 3.78-3.72 (m, 1H), 3.56-3.45 (m, 1H), 1.89-1.79 (m, 1H), 1.69-1.61 (m, 1H), 1.56-1.50 (m, 1H), 1.27-1.20 (m, 1H), 1.15-1.09 (m, 3H). MS (ESI+APCI; multimode): 301 $[M+H]^+$. HPLC: 97.0 (% of AUC).

Synthesis of VKT-012:

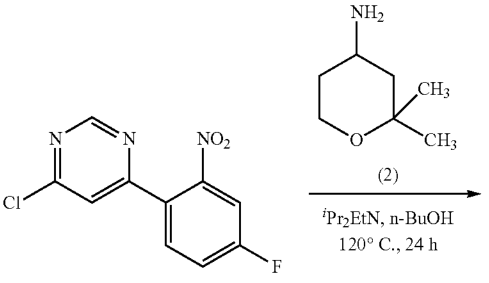

1

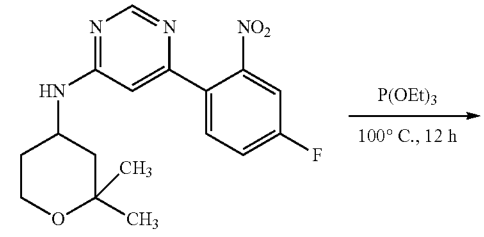

3

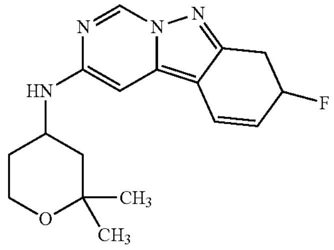

VKT-012

Preparation of 3:

To a suspension of 1 (250 mg, 0.98 mmol) in anhydrous n-butanol (10 mL), at room temperature, under $N_2$ atmosphere, was added 2 (255 mg, 1.97 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 15% $CH_3OH$ (0.5% $NH_3$): $CH_2Cl_2$ to afford 3 (130 mg, 38% yield) as a brown solid. $^1H$ NMR (400 MHz, DMSO-$d_6$): δ: 8.37 (s, 1H), 7.97 (dd, J=8.4 Hz and J=2.8 Hz, 1H), 7.78-7.75 (m, 1H), 7.70-7.66 (m, 1H), 7.55-7.53 (m, 1H), 6.63 (brs, 1H), 4.26-4.25 (m, 1H), 3.67-3.64 (m, 2H), 1.88-1.85 (m, 2H), 1.40-1.25 (m, 2H), 1.22 (s, 3H), 1.16 (s, 3H). MS (ESI+APCI; multimode): 347 $[M+H]^+$.

Preparation of VKT-012:

A solution of 3 (130 mg, 0.37 mmol) in $P(OEt)_3$ (10 mL), at room temperature, under $N_2$ atmosphere was sonicated for 15 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 20% $CH_3OH$ (0.5% $NH_3$):$CH_2Cl_2$ to obtain the crude product. The crude product was triturated with $CH_3CN$ (20 mL) and $H_2O$ (10 mL), sonicated for 15 min, whereupon the product precipitated. The precipitated product was collected by filtration under vacuum, washed with pentane (20 mL) and dried under vacuum. The product was further dried by lyophilization for 12 h to afford VKT-012 (81.0 mg, 68% yield) as a yellow solid. $^1H$ NMR (400 MHz, DMSO-$d_6$): δ: 9.40 (d, J=1.2 Hz, 1H), 8.14 (dd, J=8.8 Hz J=5.6 Hz, 1H), 7.17-7.09 (m, 3H), 6.81-6.76 (m, 1H), 3.97-3.95 (m, 1H), 3.70-3.68 (m, 2H), 1.95-1.92 (m, 1H), 1.87-1.83 (m, 1H), 1.38-1.32 (m, 2H), 1.27 (s, 3H), 1.17 (s, 3H). MS (ESI+APCI; multimode): 315 $[M+H]^+$. HPLC: 99.0 (% of AUC).

Synthesis of VKT-013:

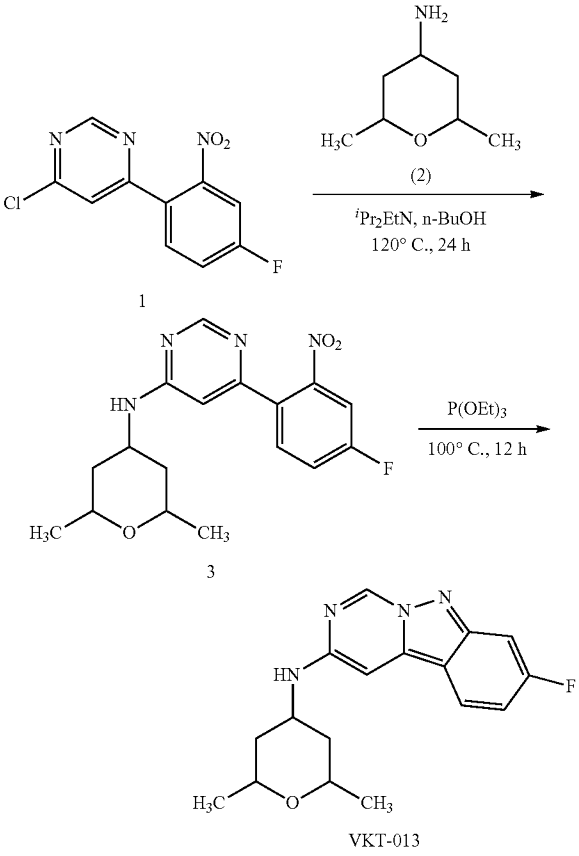

1

3

VKT-013

Preparation of 3:

To a suspension of 1 (250 mg, 0.98 mmol) in anhydrous n-butanol (10 mL), at room temperature, under $N_2$ atmosphere, was added 2 (255 mg, 1.97 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 10% $CH_3OH$ (0.5% $NH_3$):$CH_2Cl_2$ to afford 3 (140 mg, 41% yield) as a brown solid. MS (ESI+APCI; multimode): 347 $[M+H]^+$.

Preparation of VKT-013:

A solution of 3 (140 mg, 0.40 mmol) in $P(OEt)_3$ (10 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 20% $CH_3OH$ (0.5% $NH_3$):$CH_2Cl_2$ to obtain the crude product. The crude product was triturated with $CH_3CN$ (10 mL) and $H_2O$ (10 mL), sonicated for 15 min, whereupon the product precipitated. The precipitated product was collected by filtration under vacuum, washed with MTBE (20 mL) and pentane (20 mL) and dried under vacuum. The product was further dried by lyophilization for 12 h to afford VKT-013 (75.0 mg, 59% yield) as a yellow solid. $^1H$ NMR (400 MHz, DMSO-$d_6$): δ: 9.41 (dd, J=11.2 Hz and J=1.2 Hz, 1H), 8.14 (dd, J=8.8 Hz and J=5.6 Hz, 1H), 7.40 (d, J=6.8 Hz, 1H), 7.18-7.11 (m, 2H), 6.81-6.76 (m, 1H), 4.18-4.10 (m, 1H), 3.86-3.82 (m, 2H), 3.56-3.55 (m, 1H), 2.00-1.96 (m, 1H), 1.79-1.76 (m, 1H), 1.42-1.40 (m, 1H), 1.14 (d, J=6.0 Hz, 3H), 1.07 (d, J=6.0 Hz, 3H). MS (ESI+APCI; multimode): 315 $[M+H]^+$. HPLC: 99.4 (% of AUC).

Synthesis of VKT-015:

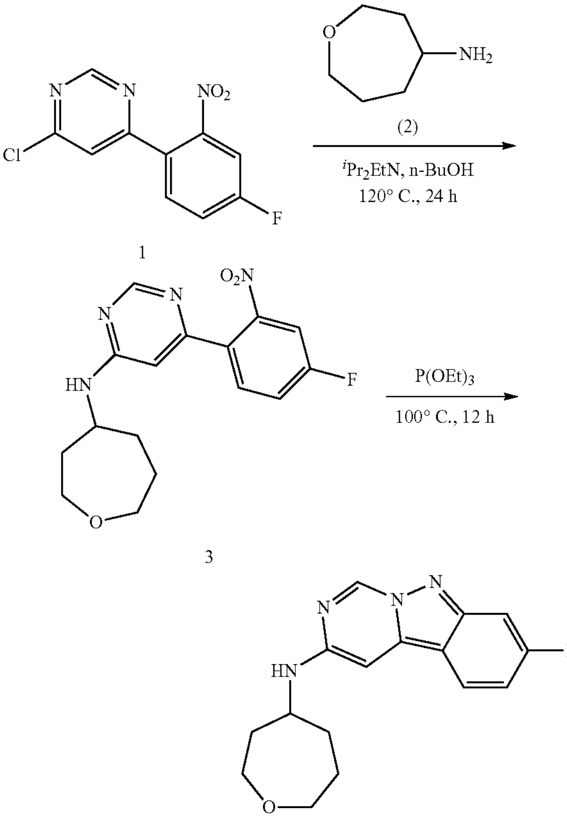

1

3

VKT-015

Preparation of 3:

To a suspension of 1 (250 mg, 0.98 mmol) in anhydrous n-butanol (10 mL), at room temperature, under $N_2$ atmosphere, was added 2 (227 mg, 1.97 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 15% $CH_3OH$ (0.5% $NH_3$):$CH_2Cl_2$ to afford 3 (165 mg, 50% yield) as a white gummy solid. $^1H$ NMR (400 MHz, DMSO-$d_6$): δ: 8.37 (s, 1H), 7.97 (dd, J=8.4 Hz and J=2.4 Hz, 1H), 7.82-7.81 (m, 1H), 7.68-7.67 (m, 1H), 7.63-7.61 (m, 1H), 6.78-6.71 (m, 1H), 4.30-4.17 (m, 1H), 3.69-3.65 (m, 1H), 3.59-3.56 (m, 1H), 3.38-3.31 (m, 1H), 2.09-1.99 (m, 1H), 1.98-1.88 (m, 1H), 1.81-1.61 (m, 4H), 1.40-1.20 (m, 1H). MS (ESI+APCI; multimode): 333 $[M+H]^+$.

Preparation of VKT-015:

A solution of 3 (165 mg, 0.49 mmol) in $P(OEt)_3$ (10 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 25% $CH_3OH$ (0.5% $NH_3$):$CH_2Cl_2$ to obtain the crude product. The crude product was triturated with $CH_3CN$ (10 mL) and $H_2O$ (10 mL), and sonicated for 15 min, whereupon the product precipitated. The precipitated product was collected by filtration under vacuum, washed with MTBE (20 mL) and pentane (20 mL) and dried under vacuum. The product was further dried by lyophilization for 12 h to afford VKT-015 (75.0 mg, 51% yield) as a yellow solid. $^1H$ NMR (400 MHz, DMSO-$d_6$): δ: 9.40 (d, J=0.8 Hz, 1H), 8.15 (dd, J=8.8 Hz and J=5.6 Hz, 1H), 7.21-7.14 (m, 2H), 7.07 (d, J=1.2 Hz, 1H), 6.80-6.75 (m, 1H), 3.74-3.70 (m, 1H), 3.69-3.64 (m, 2H), 3.63-3.60 (m, 2H), 2.04-1.98 (m, 2H), 1.80-1.76 (m, 2H), 1.75-1.71 (m, 2H). MS (ESI+APCI; multimode): 301 $[M+H]^+$. HPLC: 98.2 (% of AUC).

Synthesis of VKT-016:

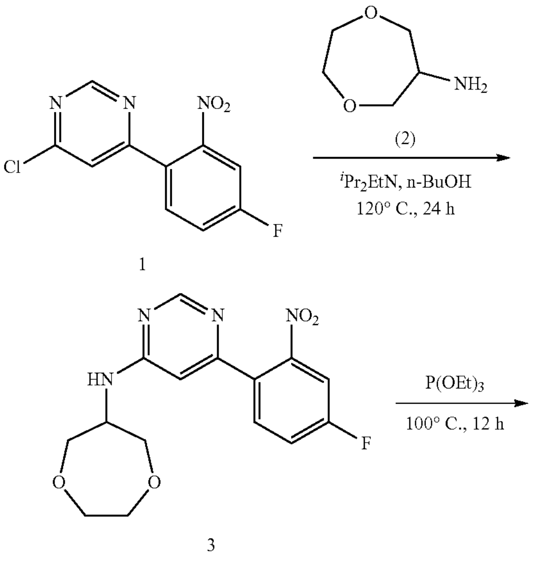

1
3

-continued

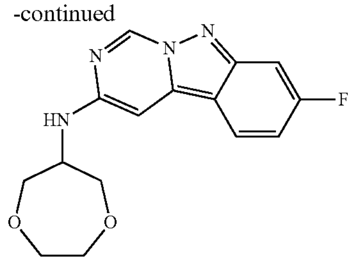

VKT-016

Preparation of 3:

To a suspension of 1 (250 mg, 0.98 mmol) in anhydrous n-butanol (10 mL), at room temperature, under $N_2$ atmosphere, was added 2 (231 mg, 1.97 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 15% $CH_3OH$ (0.5% $NH_3$):$CH_2Cl_2$ to afford 3 (280 mg, 84% yield) as a brown gummy solid. $^1H$ NMR (400 MHz, DMSO-$d_6$): δ: 8.38 (s, 1H), 7.98 (dd, J=8.8 Hz and J=2.8 Hz, 1H), 7.77-7.76 (m, 2H), 7.71-7.66 (m, 1H), 6.81 (brs, 1H), 4.47-4.41 (m, 1H), 4.31-4.28 (m, 1H), 3.97-3.93 (m, 2H), 3.81-3.71 (m, 1H), 3.40-3.35 (m, 2H), 1.41-1.21 (m, 2H). MS (ESI+APCI; multimode): 335 $[M+H]^+$.

Preparation of VKT-016:

A solution of 3 (280 mg, 0.83 mmol) in $P(OEt)_3$ (20 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 20% $CH_3OH$ (0.5% $NH_3$):$CH_2Cl_2$ to obtain the crude product. The crude product was triturated with $CH_3CN$ (10 mL) and $H_2O$ (10 mL) and sonicated for 15 min, whereupon the product precipitated. The precipitated product was collected by filtration under vacuum, washed with MTBE (20 mL) and pentane (20 mL) and dried under vacuum. The product was further dried by lyophilization for 12 h to afford VKT-016 (70.0 mg, 27% yield) as a yellow solid. $^1H$ NMR (400 MHz, DMSO-$d_6$): δ: 9.43 (d, J=1.2 Hz, 1H), 8.12 (dd, J=8.8 Hz and J=5.6 Hz, 1H), 7.22-7.16 (m, 3H), 6.82-6.77 (m, 1H), 4.31-4.28 (m, 1H), 4.00-3.96 (m, 2H), 3.75-3.70 (m, 6H). MS (ESI+APCI; multimode): 303 $[M+H]^+$. HPLC: 97.3 (% of AUC).

Synthesis of VKT-017:

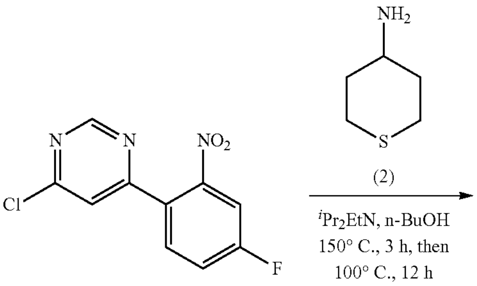

1

-continued

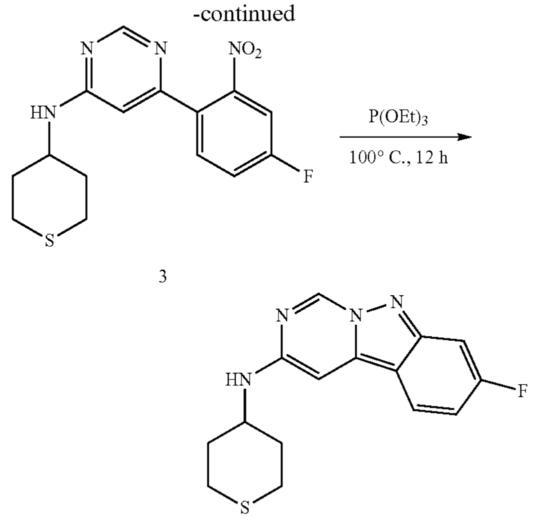

3

VKT-017

Preparation of 3:

To a suspension of 1 (250 mg, 0.98 mmol) in anhydrous n-butanol (10 mL), at room temperature, under $N_2$ atmosphere, was added 2 (231 mg, 1.97 mmol) followed with N,N-diisopropylethylamine (382 mg, 2.96 mmol). The reaction mixture was gradually heated, and stirred at 150° C. for 3 h, and then at 100° C. for 12 h. The reaction mixture was cooled to room temperature, and solvent was concentrated under vacuum to obtain the crude product. The crude product was purified by silica-gel column chromatography using 15% $CH_3OH$ (0.5% $NH_3$):$CH_2Cl_2$ to afford 3 (150 mg, 45% yield) as a brown solid. $^1H$ NMR (400 MHz, DMSO-$d_6$): δ: 8.36 (s, 1H), 7.97 (dd, J=8.4 Hz and J=2.4 Hz, 1H), 7.78-7.76 (m, 1H), 7.71-7.64 (m, 2H), 6.75-6.70 (m, 1H), 4.01-3.98 (m, 1H), 2.72-2.66 (m, 2H), 2.18-2.16 (m, 2H), 1.63-1.62 (m, 2H), 1.59-1.26 (m, 2H). MS (ESI+APCI; multimode): 335 $[M+H]^+$.

Preparation of VKT-017:

A solution of 3 (150 mg, 0.44 mmol) in $P(OEt)_3$ (10 mL), at room temperature, under $N_2$ atmosphere was sonicated for 15 min. The reaction mixture was gradually heated to 100° C. and stirred for 12 h. The reaction mixture was cooled to room temperature, and solvent was concentrated under vacuum to obtain the crude product. The crude product was purified by C-18 column chromatography using 5% $CH_3CN$:$H_2O$ followed by silica-gel column chromatography using 30% $CH_3OH$ (0.5% $NH_3$):$CH_2Cl_2$ to obtain the crude product. The crude product was triturated with $CH_3CN$ (20 mL) and sonicated for 15 min, whereupon the product precipitated. The precipitated product was collected by filtration under vacuum, washed with pentane (30 mL) and dried under vacuum. The product was further dried by lyophilization for 12 h to afford VKT-017 (105 mg, 77% yield) as yellow solid. $^1H$ NMR (400 MHz, DMSO-$d_6$): δ: 9.40 (d, J=1.2 Hz, 1H), 8.12 (dd, J=8.8 Hz and J=5.6 Hz, 1H), 7.25-7.23 (m, 1H), 7.17-7.14 (m, 1H), 7.10 (d, J=0.8 Hz, 1H), 6.81-6.76 (m, 1H), 3.68-3.63 (m, 1H), 2.79-2.67 (m, 4H), 2.24-2.20 (m, 2H), 1.67-1.64 (m, 2H). MS (ESI+APCI; multimode): 303 $[M+H]^+$. HPLC: 98.1 (% of AUC).

Synthesis of VKT-018:

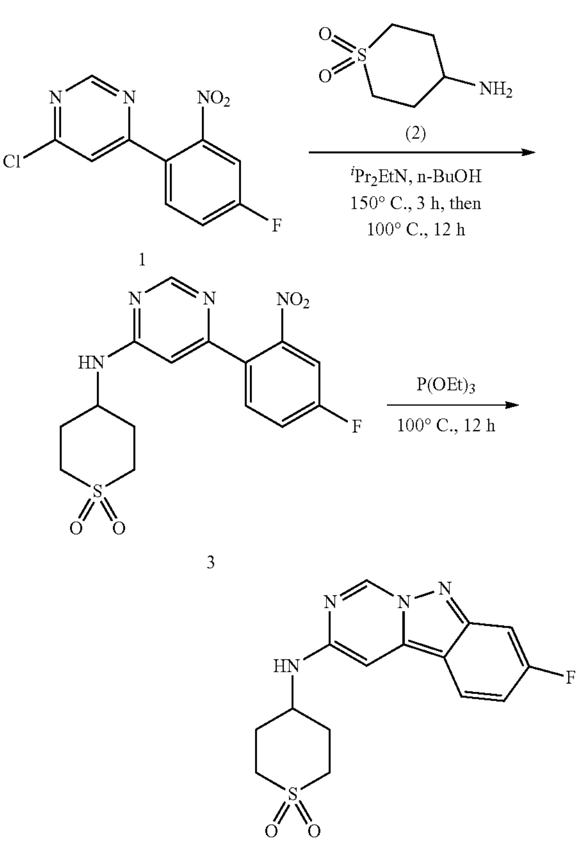

1

3

VKT-018

Preparation of 3:

To a suspension of 1 (250 mg, 0.98 mmol) in anhydrous n-butanol (10 mL), at room temperature, under $N_2$ atmosphere, was added 2 (294 mg, 1.97 mmol) followed with N,N-diisopropylethylamine (382 mg, 2.96 mmol). The reaction mixture was gradually heated, and stirred at 150° C. for 3 h, and then at 100° C. for 12 h. The reaction mixture was cooled to room temperature, and solvent was concentrated under vacuum to obtain the crude product. The crude product was purified by silica-gel column chromatography using 10% $CH_3OH$ (0.5% $NH_3$):$CH_2Cl_2$ to afford 3 (180 mg, 50% yield) as a white gummy solid. $^1H$ NMR (400 MHz, DMSO-$d_6$): δ: 8.41 (s, 1H), 7.99 (dd, J=8.4 Hz and J=2.4 Hz, 1H), 7.79-7.76 (m, 2H), 7.72-7.69 (m, 1H), 6.69 (brs, 1H), 4.32-4.28 (m, 1H), 3.39-3.20 (m, 2H), 3.17-3.11 (m, 2H), 2.24-2.21 (m, 2H), 2.01-1.98 (m, 2H). MS (ESI+APCI; multimode): 367 $[M+H]^+$.

Preparation of VKT-018:

A solution of 3 (180 mg, 0.49 mmol) in $P(OEt)_3$ (10 mL), at room temperature, under $N_2$ atmosphere, was sonicated for 10 min. The reaction mixture was gradually heated to 100° C. and stirred for 12 h. The reaction mixture was cooled to room temperature, whereupon the product precipitated. The precipitated product was collected by filtration under vacuum, washed with pentane (30 mL) and dried under vacuum. The product was further dried by lyophilization for 12 h to afford VKT-018 (115 mg, 70% yield) as a yellow solid. $^1H$ NMR (400 MHz, DMSO-$d_6$): δ: 9.45 (d, J=1.2 Hz, 1H), 8.12 (dd, J=8.8 Hz and J=5.6 Hz, 1H), 7.37 (d, J=8.4 Hz, 1H), 7.19 (dd, J=10.8 Hz and J=2.0 Hz, 1H), 7.14 (d, J=1.2 Hz, 1H), 6.84-6.79 (m, 1H), 4.05-4.03 (m, 1H), 3.31-3.17 (m, 4H), 2.32-2.23 (m, 2H), 2.10-2.01 (m, 2H). MS (ESI+APCI; multimode): 335 $[M+H]^+$. HPLC: 98.6 (% of AUC).

Synthesis of VKT-019:

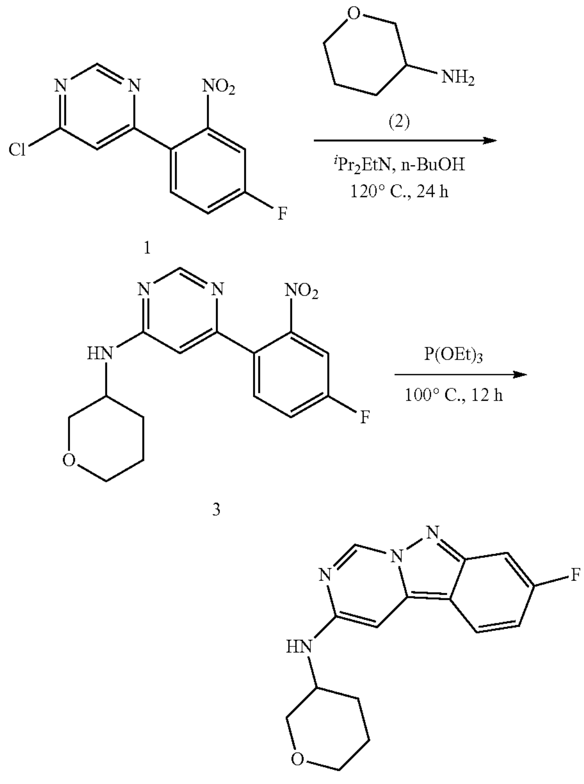

1

3

VKT-019

Preparation of 3:

To a suspension of 1 (250 mg, 0.98 mmol) in anhydrous n-butanol (10 mL), at room temperature, under $N_2$ atmosphere, was added 2 (200 mg, 1.97 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 10% $CH_3OH$ (0.5% $NH_3$): $CH_2Cl_2$ to afford 3 (150 mg, 47% yield) as a brown solid. MS (ESI+APCI; multimode): 319 $[M+H]^+$.

Preparation of VKT-019:

A solution of 3 (150 mg, 0.47 mmol) in $P(OEt)_3$ (10 mL), at room temperature, under $N_2$ atmosphere, was sonicated for 10 min. The reaction mixture was gradually heated to 100° C. and stirred for 12 h. The reaction mixture was cooled to room temperature, and solvent was concentrated under vacuum through vacuum distillation to obtain the crude product. The crude product was purified by silica-gel column chromatography using 20% $CH_3OH$ (0.5% $NH_3$): $CH_2Cl_2$ to obtain the crude product. The crude product was triturated with $CH_3CN$ (10 mL) and $H_2O$ (10 mL), sonicated for 20 min, whereupon the product precipitated. The precipitated product was collected by filtration under vacuum, washed with pentane (20 mL) and dried under vacuum. The product was further dried by lyophilization for 12 h to afford VKT-019 (75.0 mg, 55% yield) as a yellow solid. $^1H$ NMR (400 MHz, DMSO-$d_6$): δ: 9.41 (d, J=1.2 Hz, 1H), 8.15 (dd, J=8.8 Hz and J 6.0 Hz, 1H), 7.19-7.13 (m, 3H), 6.78-6.76 (m, 1H), 3.95-3.90 (m, 1H), 3.78-3.76 (m, 2H), 3.38-3.36 (m, 1H), 3.20-3.16 (m, 1H), 2.09-2.00 (m, 1H), 1.73-1.70 (m, 1H), 1.60-1.58 (m, 2H). $^1H$ NMR (400 MHz, DMSO-$d_6$) (363.5 K): δ: 9.31 (d, J=0.8 Hz, 1H), 8.07 (dd, J=8.8 Hz and J 6.0 Hz, 1H), 7.13-7.08 (m, 2H), 6.77-6.71 (m, 2H), 3.92-3.90 (m, 1H), 3.82-3.81 (m, 1H), 3.75-3.73 (m, 1H), 3.43-3.38 (m, 1H), 3.29-3.24 (m, 1H), 2.04-1.99 (m, 1H), 1.75-1.72 (m, 1H), 1.66-1.59 (m, 2H). MS (ESI+APCI; multimode): 287 $[M+H]^+$. HPLC: 99.3 (% of AUC).

Synthesis of VKT-022:

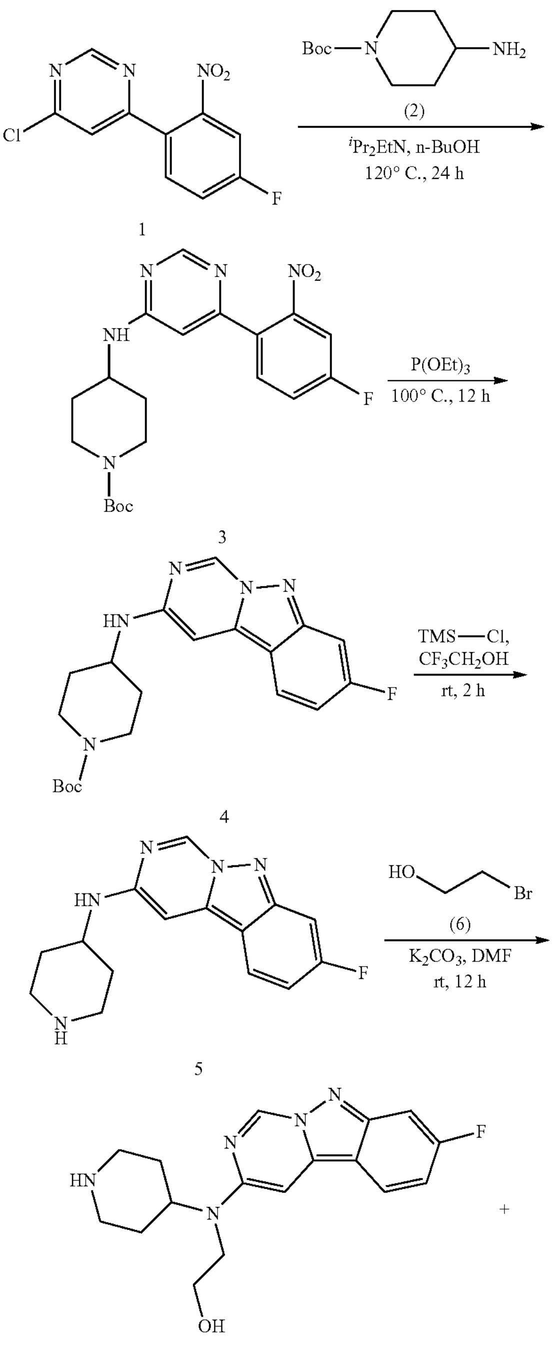

1

3

4

5

+

VKT-022-a
Tentative structure

-continued

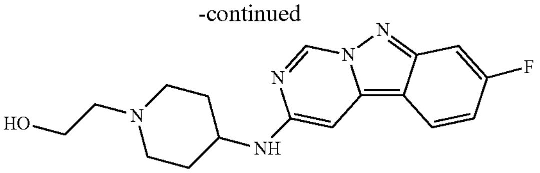

VKT-022-b
Tentative structure

Preparation of 3:

To a suspension of 1 (2.00 g, 7.90 mmol) in anhydrous n-butanol (20 mL), at room temperature, under $N_2$ atmosphere, was added 2 (3.16 g, 15.8 mmol) followed with N,N-diisopropylethylamine (3.05 g, 23.7 mmol). The reaction mixture was gradually heated, and stirred at 120° C. for 24 h. The reaction mixture was cooled to room temperature, and the solvent was concentrated by vacuum distillation to obtain the crude product. The crude product was purified by silica-gel column chromatography using 8% $CH_3OH$ (0.5% $NH_3$):$CH_2Cl_2$ to afford 3 (1.80 g, 54% yield) as a brown gummy solid. $^1H$ NMR (400 MHz, DMSO-$d_6$): δ: 8.38 (s, 1H), 7.97 (dd, J=8.4 Hz and J=2.8 Hz, 1H), 7.78-7.76 (m, 1H), 7.70-7.68 (m, 1H), 7.66-7.61 (m, 1H), 6.75-6.70 (m, 1H), 4.39-4.30 (m, 1H), 4.09-4.07 (m, 1H), 3.91-3.88 (m, 1H), 3.81-3.78 (m, 1H), 3.38-3.37 (m, 1H), 2.96-2.90 (m, 2H), 1.90-1.87 (m, 2H), 1.41 (s, 9H). MS (ESI+APCI; multimode): 418 $[M+H]^+$.

Preparation of 4:

A solution of 3 (1.80 g, 4.31 mmol) in $P(OEt)_3$ (25 mL), at room temperature, under $N_2$ atmosphere, was sonicated for 15 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 10% $CH_3OH$ (0.5% $NH_3$):$CH_2Cl_2$ to obtain 4 (1.10 g, 66% yield) as a yellow solid. $^1H$ NMR (400 MHz, DMSO-$d_6$): δ: 9.41 (s, 1H), 8.13 (dd, J=9.2 Hz, 6.0 Hz, 1H), 7.20-7.13 (m, 3H), 6.81-6.76 (m, 1H), 3.96-3.92 (m, 2H), 3.80-3.78 (m, 1H), 3.00-2.93 (m, 2H), 1.95-1.93 (m, 2H), 1.46-1.41 (m, 1H), 1.39 (s, 9H), 1.33-1.22 (m, 1H). MS (ESI+APCI; multimode): 386 $[M+H]^+$.

Preparation of 5:

To a suspension of 4 (1.10 g, 2.85 mmol) in anhydrous $CF_3CH_2OH$ (10 mL), at room temperature, under $N_2$ atmosphere, was added TMS-Cl (617 mg, 5.71 mmol). The reaction mixture was stirred at room temperature for 2 h. After completion of reaction, basic resin was added ($P^H$=8), filtered, and the filtrate was concentrated under vacuum to obtain the crude product. The crude product was purified by silica-gel column chromatography using 15% $CH_3OH$ (0.5% $NH_3$):$CH_2Cl_2$ to obtain 5 (600 mg, 73% yield) as a yellow solid. $^1H$ NMR (400 MHz, DMSO-$d_6$): δ: 9.40 (d, J=1.2 Hz, 1H), 8.14 (dd, J=9.2 Hz, 6.0 Hz, 1H), 7.26 (d, J=8.0 Hz, 1H), 7.16 (dd, J=10.8 Hz, 2.0 Hz, 1H), 7.11 (d, J=0.8 Hz, 1H), 6.81-6.76 (m, 1H), 3.70-3.62 (m, 1H), 3.39-3.30 (m, 1H), 3.08-3.05 (m, 2H), 2.71-2.65 (m, 2H), 1.96-1.93 (m, 2H), 1.49-1.33 (m, 2H). MS (ESI+APCI; multimode): 286 $[M+H]^+$.

Preparation of VKT-022-a & VKT-022-b:

To a suspension of 5 (200 mg, 0.70 mmol) in anhydrous DMF (10 mL), at room temperature, under $N_2$ atmosphere, was added 6 (87.0 mg, 0.70 mmol) followed with $k_2CO_3$ (97.0 mg, 0.70 mmol). The reaction mixture was stirred at room temperature for 12 h. After completion of reaction, the reaction mixture was diluted with 50 mL $H_2O$, and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 15% $CH_3OH$ (0.5% $NH_3$):$CH_2Cl_2$ to obtain the crude product. The crude product was triturated with $CH_3CN$ (10 mL) and MTBE (10 mL), and sonicated for 15 min, whereupon the product precipitated. The precipitated product was collected by filtration under vacuum, washed with MTBE (10 mL), pentane (20 mL) and dried under vacuum. The product was further dried by lyophilization for 12 h to afford VKT-022-a (10.0 mg, 12% yield) as a yellow solid and VKT-022-b (20.0 mg, 24% yield) as a yellow solid. VKT-022-a; IN-JIG-D-87-1: $^1H$ NMR (400 MHz, DMSO-$d_6$): δ: 9.46 (d, J=1.2 Hz, 1H), 9.28-9.26 (m, 1H), 8.12 (dd, J=8.8 Hz, 6.0 Hz, 1H), 7.38 (dd, J=14.0 Hz, 7.6 Hz, 1H), 7.22-7.16 (m, 1H), 7.15-7.10 (m, 1H), 6.84-6.79 (m, 1H), 5.33-5.30 (m, 1H), 3.78-3.76 (m, 2H), 3.62-3.59 (m, 2H), 3.22-3.12 (m, 4H), 2.21-2.18 (m, 2H), 1.85-1.79 (m, 2H). MS (ESI+APCI; multimode): 330 $[M+H]^+$. HPLC: 97.2 (% of AUC). VKT-022-b; IN-JIG-D-87-2: $^1H$ NMR (400 MHz, DMSO-$d_6$): δ: 9.39 (s, 1H), 8.14 (dd, J=9.2 Hz and 6.0 Hz, 1H), 7.17-7.10 (m, 3H), 6.80-6.75 (m, 1H), 4.39-4.36 (m, 1H), 3.57-3.51 (m, 3H), 2.91-2.90 (m, 2H), 2.51-2.50 (m, 2H), 2.19-2.13 (m, 2H), 1.95-1.92 (m, 2H), 1.54-1.51 (m, 2H). MS (ESI+APCI; multimode): 330 $[M+H]^+$. HPLC: 97.8 (% of AUC).

Synthesis of VKT-023:

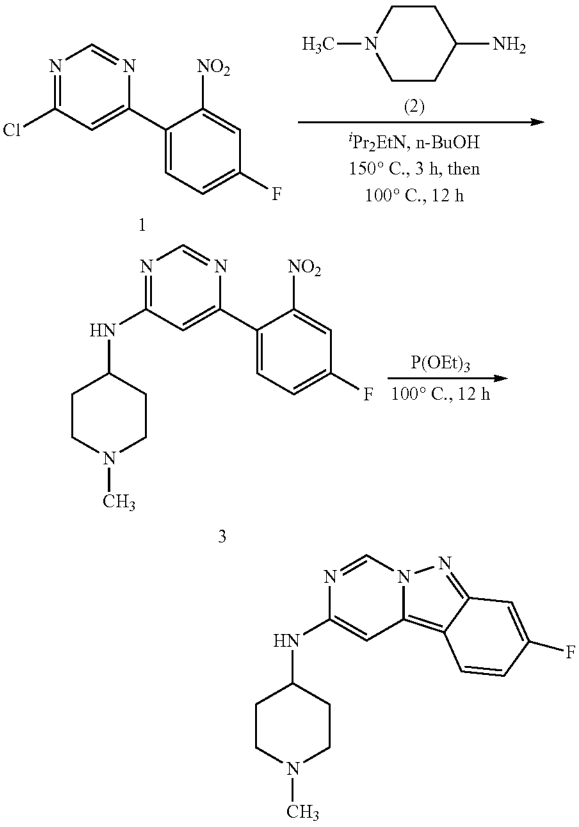

1

3

VKT-023

Preparation of 3:

To a suspension of 1 (500 mg, 1.97 mmol) in anhydrous n-butanol (10 mL), at room temperature, under $N_2$ atmosphere, was added 2 (451 mg, 3.95 mmol) followed with N,N-diisopropylethylamine (765 mg, 5.92 mmol). The reaction mixture was gradually heated, and stirred at 150° C. for 3 h, and then at 100° C. for 12 h. The reaction mixture was cooled to room temperature, and solvent was concentrated under vacuum to obtain the crude product. The crude product was purified by silica-gel column chromatography using 10% $CH_3OH$ (0.5% $NH_3$):$CH_2Cl_2$ to afford 3 (330 mg, 50% yield) as a white gummy solid. $^1H$ NMR (400 MHz, DMSO-$d_6$): δ: 8.46-8.41 (m, 1H), 7.99 (dd, J=8.4 Hz and J=2.4 Hz, 1H), 7.91-7.90 (m, 1H), 7.83-7.73 (m, 1H), 7.25-7.19 (m, 2H), 3.66-3.61 (m, 1H), 3.38-3.04 (m, 2H), 2.72 (s, 3H), 2.33-1.99 (m, 2H), 1.85-1.75 (m, 2H), 1.56-1.51 (m, 2H). MS (ESI+APCI; multimode): 332 $[M+H]^+$.

Preparation of VKT-023:

A solution of 3 (330 mg, 0.99 mmol) in $P(OEt)_3$ (20 mL), at room temperature, under $N_2$ atmosphere, was sonicated for 15 min. The reaction mixture was gradually heated to 100° C. and stirred for 12 h. The reaction mixture was cooled to room temperature, and solvent was concentrated under vacuum to obtain the crude product. The crude product was purified by C-18 reverse phase column chromatography using 5% $CH_3CN$:$H_2O$ followed by silica-gel column chromatography using 25% $CH_3OH$ (0.5% $NH_3$): $CH_2Cl_2$ to obtain the crude product. The crude product was triturated with $CH_3CN$ (20 mL), and sonicated for 15 min, whereupon the product precipitated. The precipitated product was collected by filtration under vacuum, washed with pentane (30 mL) and dried under vacuum. The product was further dried by lyophilization for 12 h to afford VKT-023 (66.0 mg, 21% yield) as yellow solid. $^1H$ NMR (400 MHz, DMSO-$d_6$, 363.6 K): δ: 9.42-9.35 (m, 1H), 8.16-8.05 (m, 1H), 7.21-7.11 (m, 1H), 6.82-6.74 (m, 1H), 3.97-3.95 (m, 1H), 3.48-3.40 (m, 2H), 3.18-3.12 (m, 4H), 2.75 (s, 3H), 2.20-2.15 (m, 2H), 1.95-1.92 (m, 2H). $^1H$ NMR (400 MHz, DMSO-$d_6$) δ: 10.38 (brs, 1H), 9.53-9.44 (m, 1H), 8.15-8.11 (m, 1H), 7.65-7.64 (m, 1H), 7.43-7.42 (m, 1H), 7.34-7.09 (m, 1H), 6.83-6.78 (m, 1H), 3.87-3.85 (m, 1H), 3.49-3.46 (m, 1H), 3.17-3.05 (m, 2H), 2.76 (s, 3H), 2.33-2.32 (m, 1H), 2.18-2.02 (m, 1H), 1.87-1.79 (m, 2H). MS (ESI+APCI; multimode): 300 $[M+H]^+$. HPLC: 94.5 (% of AUC).

Synthesis of VKT-025:

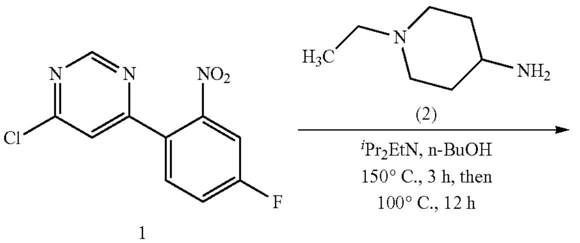

1

(2)

-continued

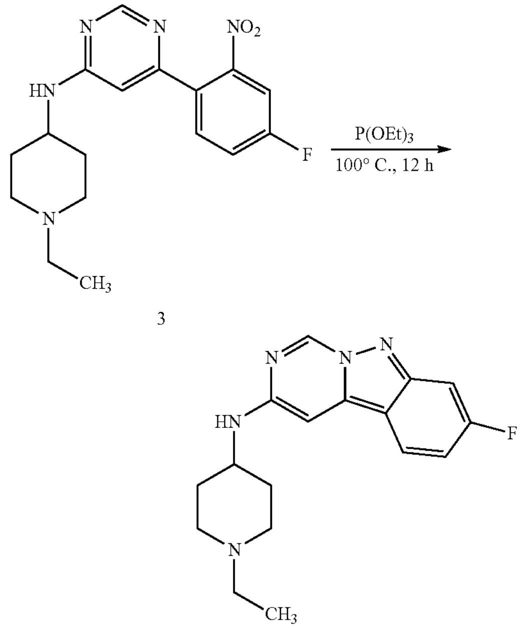

3

VKT-025

Preparation of 3:

To a suspension of 1 (250 mg, 0.98 mmol) in anhydrous n-butanol (10 mL), at room temperature, under $N_2$ atmosphere, was added 2 (253 mg, 1.97 mmol) followed with N,N-diisopropylethylamine (382 mg, 2.96 mmol). The reaction mixture was gradually heated, and stirred at 150° C. for 3 h, and then at 100° C. for 12 h. The reaction mixture was cooled to room temperature, and solvent was concentrated under vacuum to obtain the crude product. The crude product was purified by silica-gel column chromatography using 10% $CH_3OH$ (0.5% $NH_3$):$CH_2Cl_2$ to afford 3 (160 mg, 47% yield) as a white solid. $^1H$ NMR (400 MHz, DMSO-$d_6$): δ: 8.39 (s, 1H), 7.98 (dd, J=8.4 Hz and J=2.4 Hz, 1H), 7.81-7.77 (m, 2H), 7.71-7.67 (m, 1H), 6.77-6.71 (m, 1H), 4.10-3.99 (m, 1H), 3.16-3.10 (m, 2H), 3.00-2.90 (m, 1H), 2.03-1.99 (m, 2H), 1.74-1.71 (m, 2H), 1.23-1.21 (m, 6H). MS (ESI+APCI; multimode): 346 $[M+H]^+$.

Preparation of VKT-025:

A solution of 3 (160 mg, 0.46 mmol) in $P(OEt)_3$ (10 mL) at room temperature, under $N_2$ atmosphere, was sonicated for 10 min. The reaction mixture was gradually heated to 100° C. and stirred for 12 h. The reaction mixture was cooled to room temperature, and solvent was concentrated under vacuum to obtain the crude product. The crude product was purified by silica-gel column chromatography (twice) using 25% $CH_3OH$ (0.5% $NH_3$):$CH_2Cl_2$ to obtain the crude product. The crude product was triturated with $CH_3CN$ (20 mL), and sonicated for 10 min, whereupon the product precipitated. The precipitated product was collected by filtration under vacuum, washed with pentane (30 mL) and dried under vacuum. The product was further dried by lyophilization for 12 h to afford VKT-025 (51.0 mg, 35% yield) as a yellow solid. $^1H$ NMR (400 MHz, DMSO-$d_6$, 362.4 K): δ: 9.35 (s, 1H), 8.07 (dd, J=8.8 Hz and J=5.6 Hz, 1H), 7.14 (d, J=1.6 Hz, 1H), 7.11 (d, J=2.4 Hz, 2H), 6.79-6.74 (m, 1H), 3.97-3.95 (m, 1H), 3.40-3.39 (m, 2H), 3.18-3.01 (m, 4H), 2.19-2.15 (m, 2H), 1.98-1.92 (m, 2H), 1.29-1.21 (m, 3H). $^1H$ NMR (400 MHz, DMSO-$d_6$) (298 K): δ: 10.36 (brs, 1H), 9.45 (s, 1H), 8.13 (dd, J=8.8 Hz and J=2.0

Hz, 1H), 7.46-7.45 (m, 1H), 7.20-7.17 (m, 2H), 6.83-6.79 (m, 1H), 3.87-3.81 (m, 1H), 3.51-3.50 (m, 1H), 3.17-3.01 (m, 4H), 2.18-2.15 (m, 2H), 1.88-1.85 (m, 2H), 1.28-1.25 (m, 3H). MS (ESI+APCI; multimode): 314 $[M+H]^+$. HPLC: 97.6 (% of AUC).

Synthesis of VKT-026:

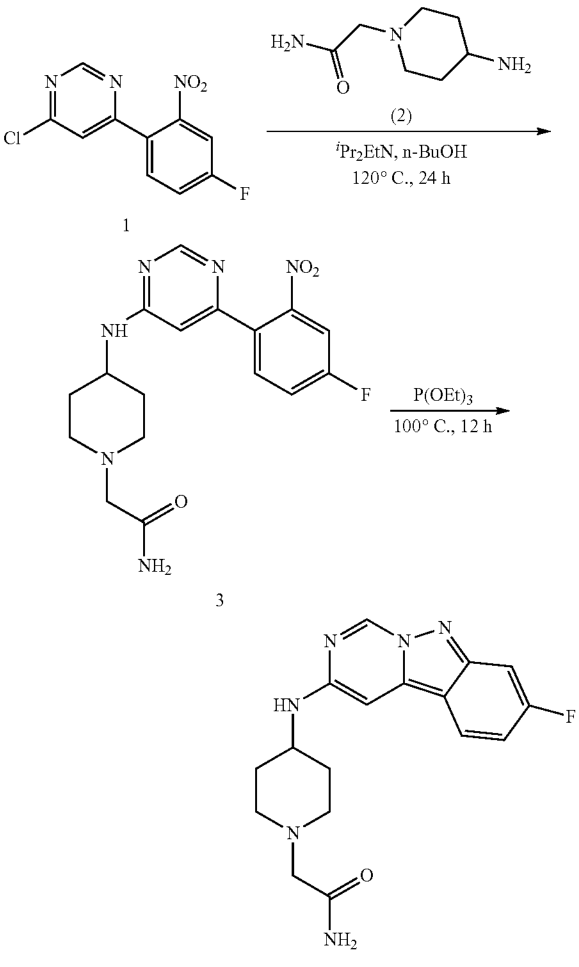

1

3

VKT-026

Preparation of 3:

To a suspension of 1 (250 mg, 0.98 mmol) in anhydrous n-butanol (10 mL), at room temperature, under $N_2$ atmosphere, was added 2 (310 mg, 1.97 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 15% $CH_3OH$ (0.5% $NH_3$): $CH_2Cl_2$ to afford 3 (200 mg, 54% yield) as a white gummy solid. $^1H$ NMR (400 MHz, DMSO-$d_6$): δ: 9.49-9.40 (m, 1H), 8.37 (s, 1H), 7.97 (dd, J=8.4 Hz and 2.4 Hz, 1H), 7.81-7.75 (m, 1H), 7.70 (dd, J=8.4 Hz, 2.4 Hz, 1H), 6.75-6.71 (m, 1H), 3.61-3.57 (m, 4H), 3.17-3.10 (m, 5H), 1.94-1.91 (m, 2H), 1.63-1.60 (m, 2H). MS (ESI+APCI; multimode): 375 $[M+H]^+$.

Preparation of VKT-026:

A solution of 3 (200 mg, 0.53 mmol) in $P(OEt)_3$ (10 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 25% $CH_3OH$ (0.5% $NH_3$):$CH_2Cl_2$ to obtain the crude product. The crude product was triturated with $CH_3CN$ (10 mL) and $H_2O$ (10 mL), and sonicated for 15 min, whereupon the product precipitated. The precipitated product was collected by filtration under vacuum, washed with MTBE (20 mL) and pentane (20 mL) and dried under vacuum. The product was further dried by lyophilization for 12 h to afford VKT-026 (75.0 mg, 41% yield) as a yellow solid. $^1H$ NMR (400 MHz, DMSO-$d_6$): δ: 9.39 (d, J=0.8 Hz, 1H), 8.14 (dd, J=8.8 Hz and 5.6 Hz, 1H), 7.18-7.13 (m, 2H), 7.11 (d, J=1.2 Hz, 1H), 6.81-6.75 (m, 1H), 3.65-3.60 (m, 1H), 2.88 (s, 2H), 2.85-2.83 (m, 2H), 2.67-2.66 (m, 2H), 2.32-2.21 (m, 2H), 2.07-1.93 (m, 2H), 1.60-1.57 (m, 2H). MS (ESI+APCI; multimode): 343 $[M+H]^+$. HPLC: 99.5 (% of AUC).

Synthesis of VKT-027:

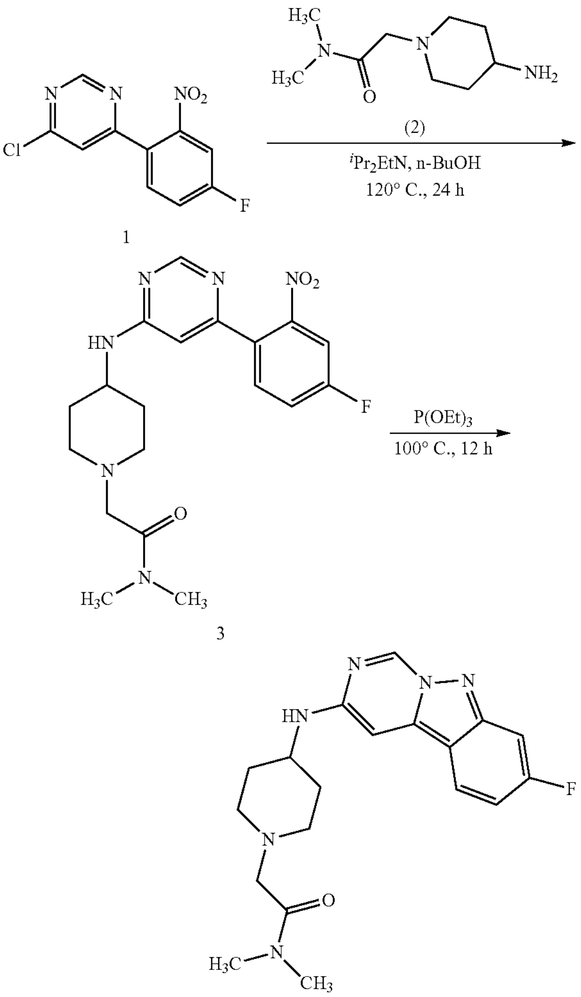

1

3

VKT-027

Preparation of 3:

To a suspension of 1 (250 mg, 0.98 mmol) in anhydrous n-butanol (10 mL), at room temperature, under $N_2$ atmosphere, was added 2 (366 mg, 1.97 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 15% $CH_3OH$ (0.5% $NH_3$): $CH_2Cl_2$ to afford 3 (160 mg, 40% yield) as a brown solid. $^1H$ NMR (400 MHz, DMSO-$d_6$): δ: 8.37 (s, 1H), 7.97 (dd, J=8.4 Hz and J=2.8 Hz, 1H), 7.77 (brs, 1H), 7.70-7.68 (m, 1H), 7.66-7.59 (m, 1H), 6.66 (brs, 1H), 3.89-3.80 (m, 1H), 3.22-3.12 (m, 2H), 3.02 (s, 2H), 2.81 (s, 6H), 2.22-2.20 (m, 2H), 1.98-1.88 (m, 2H), 1.51-1.49 (m, 2H). MS (ESI+APCI; multimode): 403 $[M+H]^+$.

Preparation of VKT-027:

A solution of 3 (160 mg, 0.39 mmol) in $P(OEt)_3$ (10 mL), at room temperature, under $N_2$ atmosphere, was sonicated for 15 min. The reaction mixture was gradually heated to 100° C. and stirred for 12 h. The reaction mixture was cooled to room temperature, and solvent was concentrated under vacuum through vacuum distillation to obtain the crude product. The crude product was purified by silica-gel column chromatography using 25% $CH_3OH$ (0.5% $NH_3$): $CH_2Cl_2$ to obtain the crude product. The crude product was triturated with $CH_3CN$ (10 mL) and $H_2O$ (10 mL), sonicated for 10 min, whereupon the product precipitated. The precipitated product was collected by filtration under vacuum, washed with pentane (20 mL) and dried under vacuum. The product was further dried by lyophilization for 12 h to afford VKT-027 (80.0 mg, 54% yield) as a yellow solid. $^1H$ NMR (400 MHz, DMSO-$d_6$): δ: 9.39 (d, J=1.2 Hz, 1H), 8.14 (dd, J=8.8 Hz and J=6.0 Hz, 1H), 7.16-7.11 (m, 3H), 6.80-6.75 (m, 1H), 3.58-3.56 (m, 1H), 3.15 (s, 2H), 3.03 (s, 3H), 2.87-2.81 (m, 5H), 2.24-2.18 (m, 2H), 1.94-1.91 (m, 2H), 1.57-1.48 (m, 2H). MS (ESI+APCI; multimode): 414 $[M+H]^+$. HPLC: 93.5 (% of AUC).

Synthesis of VKT-028:

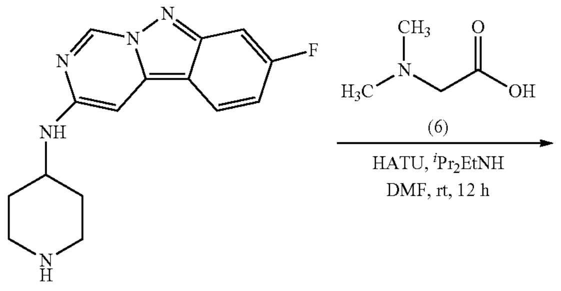

5

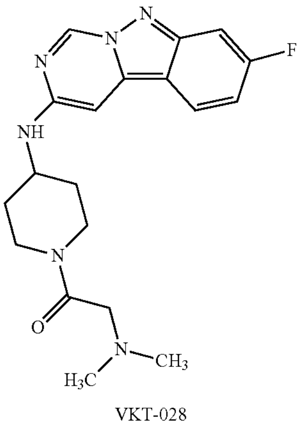

VKT-028

Preparation of VKT-028:

To a suspension of 5 (200 mg, 0.70 mmol) in anhydrous DMF (10 mL), at room temperature, under $N_2$ atmosphere, was added 6 (108 mg, 1.05 mmol) followed with HATU (400 mg, 1.05 mmol) and N,N-diisopropylethylamine (271 mg, 2.10 mmol). The reaction mixture was stirred at room temperature for 12 h. After completion of reaction, the reaction mixture was diluted with 50 mL $H_2O$, and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 20% $CH_3OH$ (0.5% $NH_3$):$CH_2Cl_2$ to obtain the crude product. The crude product was triturated with $CH_3CN$ (10 mL) and $H_2O$ (10 mL), and sonicated for 15 min, whereupon the product precipitated. The precipitated product was collected by filtration under vacuum, washed with MTBE (10 mL), pentane (20 mL) and dried under vacuum. The product was further dried by lyophilization for 12 h to afford VKT-028 (80.0 mg, 30% yield) as a yellow solid. $^1H$ NMR (400 MHz, DMSO-$d_6$): δ: 9.42 (d, J=1.2 Hz, 1H), 8.14 (dd, J=9.2 Hz and 5.6 Hz, 1H), 7.25 (d, J=8.0 Hz, 1H), 7.17 (dd, J=11.2 Hz and 2.0 Hz, 1H), 7.15 (d, J=1.2 Hz, 1H), 6.82-6.77 (m, 1H), 4.29 (d, J=12.4 Hz, 1H), 4.05 (d, J=14.0 Hz, 1H), 3.98-3.80 (m, 1H), 3.17-3.00 (m, 3H), 2.80-2.67 (m, 1H), 2.19 (s, 6H), 1.99-1.96 (m, 2H), 1.51-1.31 (m, 2H). MS (ESI+APCI; multimode): 371 $[M+H]^+$. HPLC: 99.8 (% of AUC).

Synthesis of VKT-029:

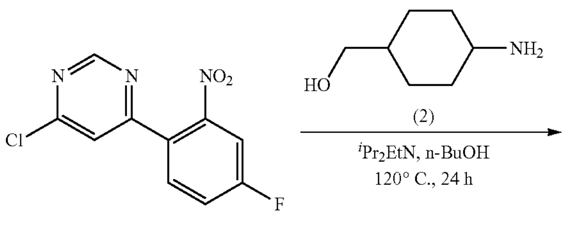

1

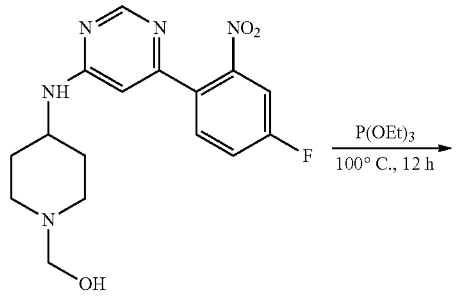

3

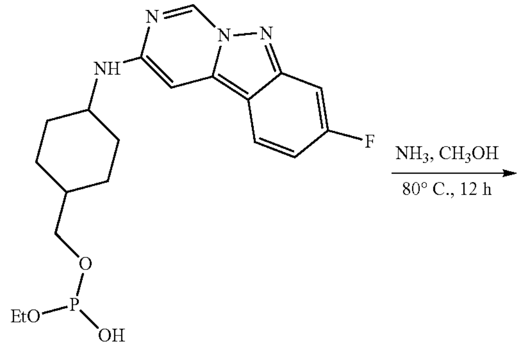

4

-continued

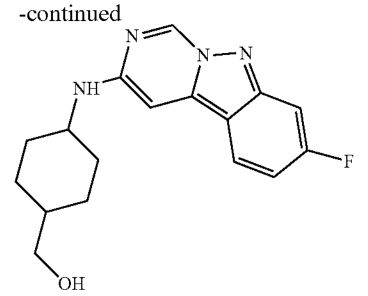

VKT-029

Preparation of 3:

To a suspension of 1 (250 mg, 0.98 mmol) in anhydrous n-butanol (10 mL), at room temperature, under $N_2$ atmosphere, was added 2 (191 mg, 1.48 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 10% $CH_3OH$ (0.5% $NH_3$): $CH_2Cl_2$ to afford 3 (220 mg, 64% yield) as a brown gummy solid. $^1H$ NMR (400 MHz, DMSO-$d_6$): δ: 8.35 (s, 1H), 7.96 (dd, J=8.4 Hz, 2.8 Hz, 1H), 7.80-7.75 (m, 1H), 7.69-7.67 (m, 1H), 7.59-7.50 (m, 1H), 6.65-6.60 (m, 1H), 4.40 (t, J=5.6 Hz, 1H), 4.30 (t, J=5.2 Hz, 1H), 3.85-3.79 (m, 1H), 3.38 (dq, J=11.6 Hz and 6.4 Hz, 2H), 3.23 (t, J=5.6 Hz, 2H), 2.05-1.97 (m, 1H), 1.82-1.76 (m, 1H), 1.40-1.35 (m, 1H), 1.34-1.26 (m, 2H), 1.19-0.84 (m, 1H). MS (ESI+APCI; multimode): 347 $[M+H]^+$.

Preparation of 4:

A solution of 3 (220 mg, 0.63 mmol) in $P(OEt)_3$ (15 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 10% $CH_3OH$ (0.5% $NH_3$):$CH_2Cl_2$ to obtain 4 (200 mg, 69% yield) as a yellow solid. MS (ESI+APCI; multimode): 451 $[M+H]^+$.

Preparation of VKT-029:

To a stirred solution of 4 (200 mg, 0.44 mmol) in $CH_3OH$ (10 mL), at room temperature, under $N_2$ atmosphere, was added ammonia (Aq.10 mL). The reaction mixture was gradually heated to 80° C. and stirred for 12 h. The reaction mixture was cooled to room temperature, and the solvent was concentrated under vacuum to obtain the crude product. The crude product was purified by silica-gel column chromatography using 25% $CH_3OH$ (0.5% $NH_3$):$CH_2Cl_2$ to obtain the crude product. The crude product was triturated with $CH_3CN$ (10 mL) and $H_2O$ (10 mL), and sonicated for 15 min, whereupon the product precipitated. The precipitated product was collected by filtration under vacuum, washed with pentane (20 mL) and dried under vacuum. The product was further dried by lyophilization for 12 h to afford VKT-029 (70.0 mg, 50% yield) as a yellow solid. $^1H$ NMR (400 MHz, DMSO-$d_6$): δ: 9.36 (d, J=1.2 Hz, 1H), 8.13 (dd, J=8.8 Hz and 5.6 Hz, 1H), 7.14 (dd, J=10.8 Hz and 2.0 Hz, 1H), 7.10-7.07 (m, 2H), 6.78-6.76 (m, 1H), 4.41 (t, J=5.6 Hz, 1H), 3.57-3.50 (m, 1H), 3.25 (t, J=5.6 Hz, 2H), 2.04-2.01 (m, 2H), 1.82-1.79 (m, 2H), 1.43-1.33 (m, 1H), 1.32-1.21 (m, 2H), 1.07-1.04 (m, 2H). MS (ESI+APCI; multimode): 315 $[M+H]^+$. HPLC: 95.2 (% of AUC).

Synthesis of Int.4 for VKT-031:

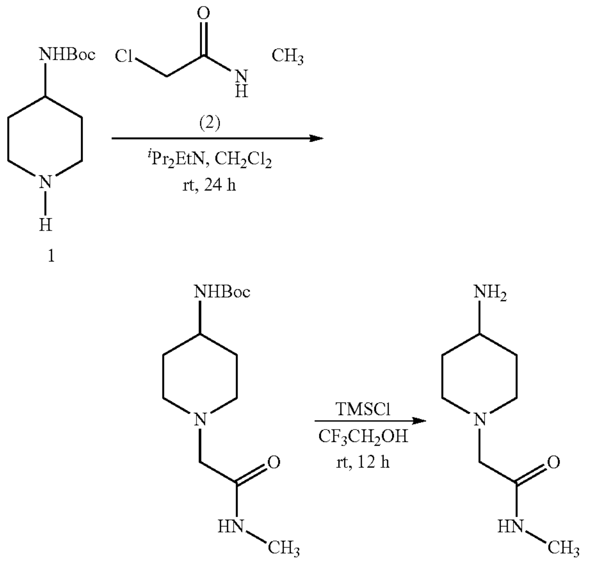

1

3

4

Preparation of 3:

To a suspension of 1 (2.00 g, 10.0 mmol) in anhydrous $CH_2Cl_2$ (20 mL), at room temperature, under $N_2$ atmosphere, was added 2 (1.60 g, 15.0 mmol) followed with N,N-diisopropylethylamine (2.50 g, 20.0 mmol). The reaction mixture was stirred at rt for 24 h. The solvent was concentrated under vacuum to obtain the crude product. The crude product was purified by silica-gel column chromatography using 5% $CH_3OH$:$CH_2Cl_2$ to afford 3 (1.60 g, 59% yield) as a brown liquid. MS (ESI+APCI; multimode): 272 $[M+H]^+$.

Preparation of 4:

To a suspension of 3 (1.60 g, 5.90 mmol) in anhydrous $CF_3CH_2OH$ (20 mL), at room temperature, under $N_2$ atmosphere, was added TMSCl (1.60 g, 11.8 mmol). The reaction mixture was stirred at rt for 12 h. The solvent was concentrated under vacuum to obtain the crude product. The crude product was purified by silica-gel column chromatography using 5% $CH_3OH$ (0.1% $NH_3$):$CH_2Cl_2$ to afford 4 (600 mg, 60% yield) as a brown liquid. MS (ESI+APCI; multimode): 172 $[M+H]^+$.

Synthesis of VKT-031:

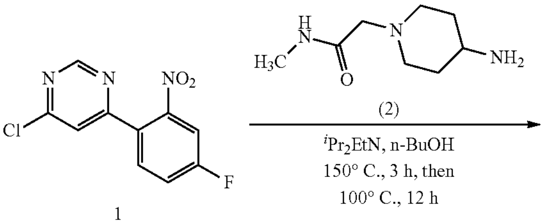

1

-continued

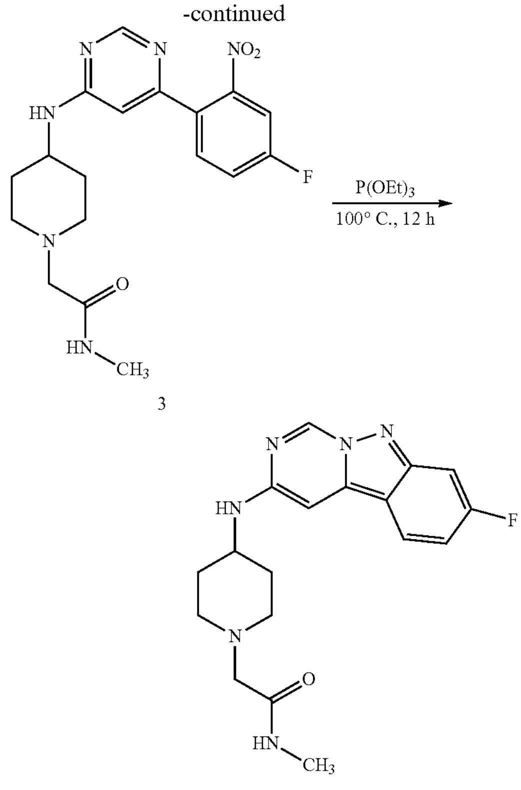

3

VKT-031

Preparation of 3:

To a suspension of 1 (500 mg, 1.97 mmol) in anhydrous n-butanol (20 mL), at room temperature, under $N_2$ atmosphere, was added 2 (676 mg, 3.95 mmol) followed with N,N-diisopropylethylamine (765 mg, 5.92 mmol). The reaction mixture was gradually heated, and stirred at 150° C. for 3 h, and then at 100° C. for 12 h. The reaction mixture was cooled to room temperature, and the solvent was concentrated by vacuum distillation to obtain the crude product. The crude product was purified by silica-gel column chromatography using 20% $CH_3OH$ (0.5% $NH_3$):$CH_2Cl_2$ to afford 3 (280 mg, 36% yield) as a white gummy solid. $^1H$ NMR (400 MHz, DMSO-$d_6$): δ: 9.36 (brs, 1H), 8.37 (brs, 1H), 7.97 (dd, J=8.4 Hz and J=2.4 Hz, 1H), 7.79-7.72 (m, 2H), 7.71-7.67 (m, 1H), 6.73-6.70 (m, 1H), 3.60-3.57 (m, 4H), 3.13-3.10 (m, 4H), 2.64-2.63 (m, 2H), 1.98-1.93 (m, 2H), 1.68-1.60 (m, 2H). MS (ESI+APCI; multimode): 389 $[M+H]^+$.

Preparation of VKT-031:

A solution of 3 (280 mg, 0.72 mmol) in $P(OEt)_3$ (20 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 25% $CH_3OH$ (0.5% $NH_3$):$CH_2Cl_2$ to obtain the crude product. The crude product was triturated with $CH_3CN$ (10 mL) and $H_2O$ (10 mL), and sonicated for 10 min, whereupon the product precipitated. The precipitated product was collected by filtration under vacuum, washed with pentane (20 mL) and dried under vacuum. The product was further dried by lyophilization for 12 h to afford VKT-031 (75.0 mg, 28% yield;) as a yellow solid. $^1H$ NMR (400 MHz, DMSO-$d_6$): δ: 9.39 (d, J=1.2 Hz, 1H), 8.14 (dd, J=8.8 Hz and J=6.0 Hz, 1H), 7.65 (d, J=4.0 Hz, 1H), 7.20-7.11 (m, 3H), 6.80-6.75 (m, 1H), 3.66-3.56 (m, 1H), 2.92 (s, 2H), 2.83-2.80 (m, 2H), 2.62 (d, J=4.8 Hz, 3H), 2.26-2.20 (m, 2H), 1.95-1.92 (m, 2H), 1.64-1.55 (m, 2H). MS (ESI+APCI; multimode): 357 $[M+H]^+$. HPLC: 98.7 (% of AUC).

Synthesis of VKT-032:

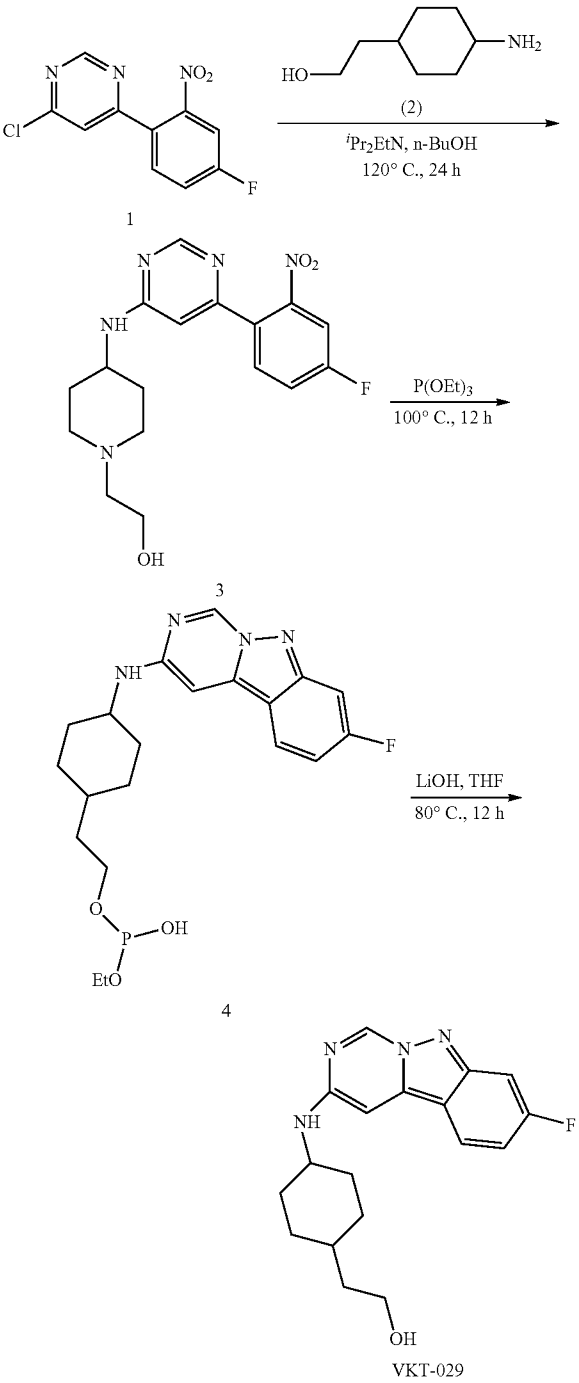

1

3

4

VKT-029

Preparation of 3:

To a suspension of 1 (250 mg, 0.98 mmol) in anhydrous n-butanol (10 mL), at room temperature, under $N_2$ atmosphere, was added 2 (212 mg, 1.48 mmol) followed with N,N-diisopropylethylamine (382 mg, 2.96 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 15% $CH_3OH$ (0.5% $NH_3$): $CH_2Cl_2$ to afford 3 (220 mg, 61% yield) as a white gummy solid. $^1H$ NMR (400 MHz, DMSO-$d_6$): δ: 8.35 (s, 1H), 7.98-7.95 (m, 1H), 7.85-7.80 (m, 1H), 7.70-7.67 (m, 1H), 7.55-7.50 (m, 1H), 6.67-6.60 (m, 1H), 4.32 (t, J=5.2 Hz, 1H), 4.10-3.80 (m, 1H), 3.45-3.42 (m, 3H), 2.69-2.60 (m, 1H), 2.17-2.10 (m, 1H), 1.98-1.77 (m, 2H), 1.74-1.63 (m, 1H), 1.62-1.59 (m, 2H), 1.54-1.51 (m, 1H), 1.42-1.36 (m, 1H), 1.35-1.23 (m, 1H). MS (ESI+APCI; multimode): 361 $[M+H]^+$.

Preparation of 4:

A solution of 3 (220 mg, 0.61 mmol) in $P(OEt)_3$ (15 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 25% $CH_3OH$ (0.5% $NH_3$):$CH_2Cl_2$ to obtain 4 (190 mg, 67% yield) as a yellow solid. MS (ESI+APCI; multimode): 465 $[M+H]^+$.

Preparation of VKT-032:

To a stirred solution of 4 (190 mg, 0.40 mmol) in THF (10 mL), at room temperature, under $N_2$ atmosphere, was added $LiOH{\cdot}H_2O$ (42.0 mg, 1.22 mmol). The reaction mixture was gradually heated to 80° C. and stirred for 2 h. The reaction mixture was cooled to room temperature, and the solvent was concentrated under vacuum to obtain the crude product. The crude product was purified by silica-gel column chromatography using 25% $CH_3OH$ (0.5% $NH_3$):$CH_2Cl_2$ to obtain the crude product. The crude product was triturated with $CH_3CN$ (10 mL) and $H_2O$ (10 mL), and sonicated for 15 min, whereupon the product precipitated. The precipitated product was collected by filtration under vacuum, washed with pentane (20 mL) and dried under vacuum. The product was further dried by lyophilization for 12 h to afford VKT-032 (85.0 mg, 63% yield) as a yellow solid. $^1H$ NMR (400 MHz, DMSO-$d_6$): δ: 9.38-9.36 (m, 1H), 8.16-8.11 (m, 1H), 7.15-7.07 (m, 3H), 6.78-6.71 (m, 1H), 4.32 (t, J=5.2 Hz, 1H), 4.01-3.85 (m, 1H), 3.46-3.36 (m, 2H), 2.09-2.00 (m, 2H), 1.80-1.75 (m, 2H), 1.70-1.50 (m, 2H), 1.45-1.35 (m, 2H), 1.30-1.20 (m, 2H), 1.09-1.05 (m, 1H). MS (ESI+APCI; multimode): 329 $[M+H]^+$. HPLC: 94.9 (% of AUC).

Synthesis of VKT-033 & VKT-034:

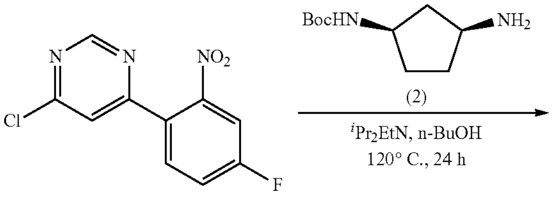

1

-continued

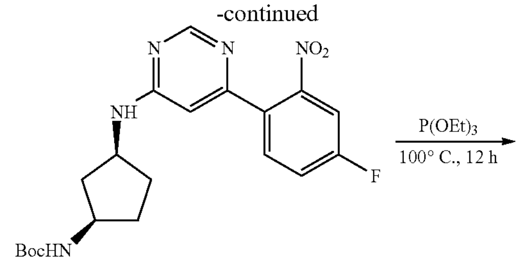

3

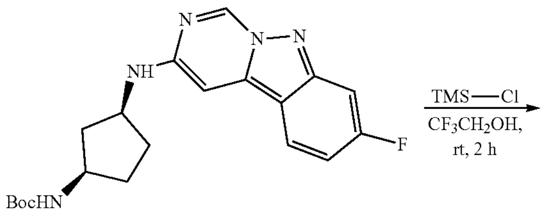

VKT-033

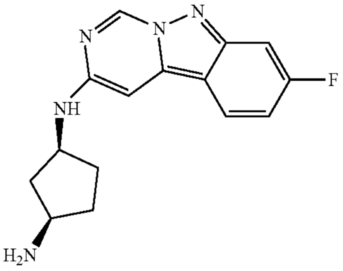

VKT-034

Preparation of 3:

To a suspension of 1 (500 mg, 1.97 mmol) in anhydrous n-butanol (20 mL), at room temperature, under $N_2$ atmosphere, was added 2 (474 mg, 2.37 mmol) followed with N,N-diisopropylethylamine (765 mg, 5.92 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 5% $CH_3OH$ (0.5% $NH_3$): $CH_2Cl_2$ to afford 3 (500 mg, 60% yield) as a brown gummy solid. $^1H$ NMR (400 MHz, DMSO-$d_6$): δ: 8.36 (s, 1H), 7.97 (dd, J=8.0 Hz and 2.4 Hz, 1H), 7.77-7.70 (m, 1H), 7.69 (dd, J=8.0 Hz and 2.4 Hz, 1H), 6.93-6.90 (m, 1H), 6.66-6.64 (m, 1H), 4.24-4.20 (m, 1H), 3.80-3.78 (m, 1H), 2.32-2.29 (m, 2H), 1.98-1.92 (m, 1H), 1.85-1.81 (m, 1H), 1.54-1.50 (m, 2H), 1.34 (s, 9H), 1.32-1.30 (m, 1H). MS (ESI+APCI; multimode): 418 $[M+H]^+$.

Preparation of VKT-033:

A solution of 3 (500 mg, 1.19 mmol) in $P(OEt)_3$ (25 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 15% $CH_3OH$ (0.5% $NH_3$):$CH_2Cl_2$ to obtain the crude product. The crude product was triturated with $CH_3CN$ (20 mL) and $H_2O$ (20 mL), and sonicated for 15 min, whereupon the product precipitated. The precipitated product was collected by filtration under vacuum, washed with MTBE (20 mL) and pentane (20 mL) and dried under vacuum. The product was further dried by lyophilization for 12 h to afford VKT-033 (350 mg, 75% yield) as a yellow solid. $^1$H NMR (400 MHz, DMSO-$d_6$): δ: 9.38 (d, J=0.8 Hz, 1H), 8.15 (dd, J=8.4 Hz and 5.6 Hz, 1H), 7.27 (d, J=7.2 Hz, 1H), 7.16 (dd, J=10.8 Hz and 2.0 Hz, 1H), 7.06 (d, J=1.2 Hz, 1H), 6.95 (d, J=7.6 Hz, 1H), 6.81-6.76 (m, 1H), 3.96-3.94 (m, 1H), 3.88-3.80 (m, 1H), 2.61-2.58 (m, 1H), 2.55-2.40 (m, 1H), 2.07-1.97 (m, 1H), 1.90-1.80 (m, 1H), 1.66-1.55 (m, 1H), 1.54-1.50 (m, 1H), 1.38 (s, 9H). MS (ESI+APCI; multimode): 386 $[M+H]^+$. HPLC: 99.7 (% of AUC).

Preparation of VKT-034:

To a suspension of VKT-033 (200 mg, 0.51 mmol) in anhydrous $CF_3CH_2OH$ (10 mL), at room temperature, under $N_2$ atmosphere, was added TMS-Cl (112 mg, 1.03 mmol). The reaction mixture was stirred at room temperature for 2 h. After completion of reaction, basic resin was added ($P^H$=8), filtered, and the filtrate was concentrated under vacuum to obtain the crude product. The crude product was purified by silica-gel column chromatography using 20% $CH_3OH$ (0.5% $NH_3$):$CH_2Cl_2$ to obtain the crude product. The crude product was triturated with $CH_3CN$ (20 mL), $H_2O$ (10 mL), and sonicated for 15 min, whereupon the product precipitated. The precipitated product was collected by filtration under vacuum, washed with MTBE (25 mL) and pentane (20 mL) and dried under vacuum. The product was further dried by lyophilization for 12 h to afford VKT-034 (90.0 mg, 60% yield) as a yellow solid. $^1$H NMR (400 MHz, DMSO-$d_6$): δ: 9.37 (s, 1H), 8.15 (dd, J=9.2 Hz and 6.0 Hz, 1H), 7.32 (d, J=7.2 Hz, 1H), 7.16 (dd, J=10.8 Hz and 2.0 Hz, 1H), 7.05 (s, 1H), 6.81-6.76 (m, 1H), 4.00-3.98 (m, 1H), 3.31 (t, J=6.4 Hz, 1H), 3.02-3.00 (m, 2H), 2.29-2.26 (m, 2H), 2.04-1.99 (m, 1H), 1.83-1.78 (m, 1H), 1.73-1.70 (m, 1H), 1.48-1.33 (m, 1H). MS (ESI+APCI; multimode): 286 $[M+H]^+$. HPLC: 97.4 (% of AUC).

Synthesis of VKT-035 & VKT-036:

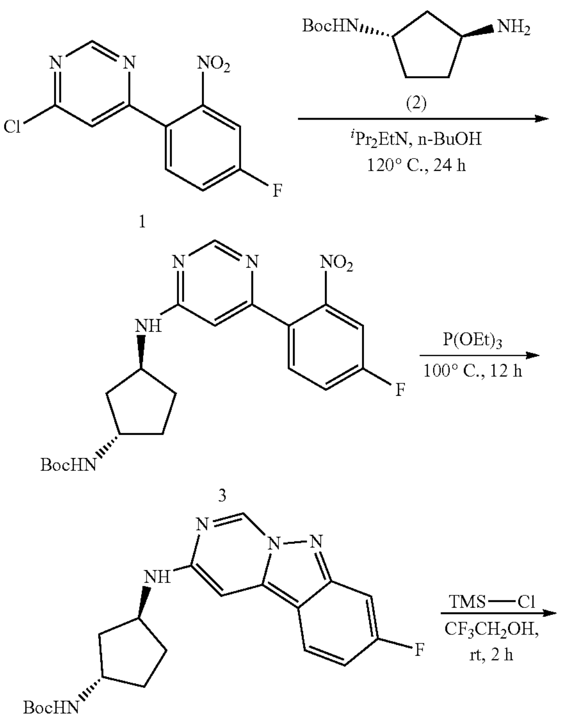

VKT-035

-continued

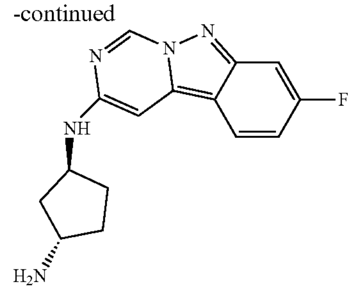

VKT-036

Preparation of 3:

To a suspension of 1 (500 mg, 1.97 mmol) in anhydrous n-butanol (20 mL), at room temperature, under $N_2$ atmosphere, was added 2 (474 mg, 2.37 mmol) followed with N,N-diisopropylethylamine (765 mg, 5.92 mmol). The reaction mixture was gradually heated to 120° C. and stirred for 24 h. The reaction mixture was cooled to room temperature, and solvent was concentrated under vacuum to obtain the crude product. The crude product was purified by silica-gel column chromatography using 5% $CH_3OH$ (0.5% $NH_3$): $CH_2Cl_2$ to afford 3 (550 mg, 66% yield) as a brown gummy solid. MS (ESI+APCI; multimode): 418 $[M+H]^+$.

Preparation of VKT-035:

A solution of 3 (550 mg, 1.31 mmol) in $P(OEt)_3$ (25 mL), at room temperature, under $N_2$ atmosphere, was sonicated for 10 min. The reaction mixture was gradually heated to 100° C. and stirred for 12 h. The reaction mixture was cooled to room temperature, and the solvent was concentrated by vacuum distillation to obtain the crude product. The crude product was purified by silica-gel column chromatography using 15% $CH_3OH$ (0.5% $NH_3$):$CH_2Cl_2$ to obtain the crude product. The crude product was triturated with $CH_3CN$ (20 mL) and $H_2O$ (20 mL), and sonicated for 15 min, whereupon the product precipitated. The precipitated product was collected by filtration under vacuum, washed with MTBE (20 mL) and pentane (20 mL) and dried under vacuum. The product was further dried by lyophilization for 12 h to afford VKT-035 (320 mg, 63% yield) as a yellow solid. $^1$H NMR (400 MHz, DMSO-$d_6$): δ: 9.38 (d, J=1.2 Hz, 1H), 8.14 (dd, J=9.2 Hz, 6.0 Hz, 1H), 7.28 (d, J=7.2 Hz, 1H), 7.16 (dd, J=11.2 Hz and 2.0 Hz, 1H), 7.02 (s, 1H), 6.93 (d, J=6.8 Hz, 1H), 6.81-6.76 (m, 1H), 4.11-4.09 (m, 1H), 3.97-3.95 (m, 1H), 2.17-2.15 (m, 1H), 2.00-1.98 (m, 1H), 1.88-1.84 (m, 2H), 1.55-1.50 (m, 1H), 1.49-1.43 (m, 1H), 1.38 (s, 9H). MS (ESI+APCI; multimode): 386 $[M+H]^+$. HPLC: 97.4 (% of AUC).

Preparation of VKT-036:

To a suspension of VKT-035 (200 mg, 0.51 mmol) in anhydrous $CF_3CH_2OH$ (10 mL), at room temperature, under $N_2$ atmosphere, was added TMS-Cl (112 mg, 1.03 mmol). The reaction mixture was stirred at room temperature for 2 h. After completion of reaction, basic resin was added (PH=8), filtered, and the filtrate was concentrated under vacuum to obtain the crude product. The crude product was purified by silica-gel column chromatography using 20% $CH_3OH$ (0.5% $NH_3$):$CH_2Cl_2$ to obtain the crude product. The crude product was triturated with $CH_3CN$ (20 mL), $H_2O$ (10 mL), and sonicated for 10 min, whereupon the product precipitated. The precipitated product was collected by filtration under vacuum, washed with MTBE (25 mL) and pentane (20 mL) and dried under vacuum. The product was further dried by lyophilization for 12 h to afford VKT-036 (80.0 mg, 54% yield) as a yellow solid. $^1$H NMR (400 MHz, DMSO-$d_6$): δ: 9.41 (d, J=0.8 Hz, 1H), 8.15 (dd, J=9.2 Hz and 6.0 Hz, 1H), 7.32 (d, J=6.8 Hz, 1H), 7.15 (dd, J=11.2 Hz and 2.0 Hz, 1H), 7.07 (s, 1H), 6.82-6.77 (m, 1H), 4.24-4.19 (m, 1H), 3.69-3.60 (m, 1H), 3.32-3.31 (m, 2H), 2.27-2.20 (m, 1H), 2.12-2.05 (m, 1H), 1.96-1.91 (m, 2H), 1.63-1.57 (m, 2H). MS (ESI+APCI; multimode): 286 $[M+H]^+$. HPLC: 97.4 (% of AUC).

Synthesis of VKT-511

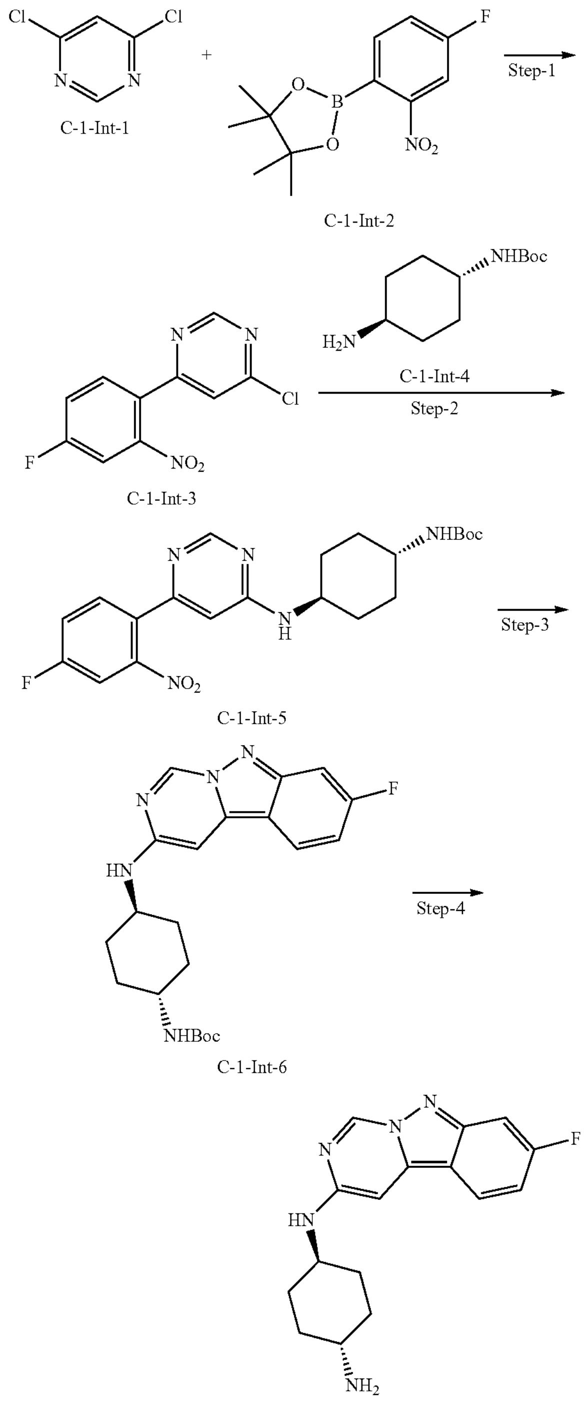

C-1-Int-1

C-1-Int-2

C-1-Int-3

C-1-Int-5

C-1-Int-6

VKT-511

Synthesis of 4-chloro-6-(4-fluoro-2-nitrophenyl) pyrimidine (C-1-Int-3)

4,6-dichloropyrinidine (0.250 g, 1.689 mmol) was taken in a microwave vial and dissolved in DMF (3.3 mL). 2-(4-fluoro-2-nitrophenyl)-4,4,5,5-tetramethyl-1,3,2-dioxaborolane (0.224 g, 0.844 mmol) and $Na_2CO_3$ (2M aq., 1.66 mL) was added into the reaction mixture. The mixture was purged with nitrogen for 20 minutes and added $PdCl_2$(dppf)·MDC (0.137 g, 0.168 mmol). Reaction mixture was sonicated for 15 minutes before heating in microwave at 100° C. for 10 minutes, stalling material was observed on TLC, hence again nitrogen purged for 10 minutes and reaction mass was sonicated for 10 minutes and heated at 100° C. for 10 minutes. Reaction mass was quenched with water (5 mL) and extracted with ethyl acetate (3 mL×3), the organic layer was dried over sodium sulfate and concentrated to crude material. Crude material was purified by column chromatography using (7-9%) ethyl acetate: hexane to get 4-chloro-6-(4-fluoro-2-nitrophenyl) pyrimidine (C-1-Int-3). (0.087 g, 20.44% yield). 1H NMR (400 MHz, DMSO-d6) δ 9.094 (s, 1H), 8.252 (s, 1H), 8.157-8.142 (d, J=8.4 Hz, 1H), 8.00-8.038 (m, 1H), 7.81-7.85 (m, 1H).

Synthesis tert-butyl ((1r,4r)-4-((6-(4-fluoro-2-nitrophenyl)pyrimidin-4-yl)amino)cyclohexyl)carbamate (C-1-Int-5)

4-chloro-6-(4-fluoro-2-nitrophenyl) pyrimidine (C-1-Int-3) (0.250 g, 0.985 mmol) and tert-butyl ((1r,4r)-4-aminocyclohexyl)carbamate (C-1-Int-4) (0.844 g, 3.94 mmol) in DME (4.5 mL). Reaction mixture was irradiated at 140° C. for 30 minutes. After completion of reaction DME was evaporated under reduced pressure to get residue. Residue was triturated with diethyl ether (3 mL, two times) to remove upper impurities. Resulting crude material was purified on column chromatography using (20-25%) ethyl acetate hexane to get tert-butyl ((1r,4r)-4-((6-(4-fluoro-2-nitrophenyl)pyrimidin-4-yl)amino)cyclohexyl)carbamate (C-1-Int-5). (0.285 g, 67.01% yield). LC-MS: m/z 432.65 [M+1H], tRet=1.62 min.

Synthesis of tert-butyl ((1r,4r)-4-((7-fluoropyrimido[1,6-b]indazol-3-yl)amino)cyclohexyl)carbamate (C-1-Int-6)

A mixture of tert-butyl ((1r,4r)-4-((6-(4-fluoro-2-nitrophenyl)pyrimidin-4-yl)amino)cyclohexyl)carbamate (C-1-Int-5) (0.285 g, 0.66 mmol.) and triethyl phosphite (0.548 g, 3.30 mmol.) was irradiated under microwave at 170° C. for 20 minutes. After completed of reaction triethyl phosphite was evaporated under reduced pressure (at 60° C.) to get residue. Residue was triturated with n-pentane (5 mL, two times) to remove remaining triethyl phosphite. Resulting crude material was purified on column chromatography using (20-30%) ethyl acetate in hexane. Pure fractions were distilled out to afford tert-butyl ((1r,4r)-4-((7-fluoropyrimido[1,6-b]indazol-3-yl)amino)cyclohexyl)carbamate (C-1-Int-6). (0.11 g, 41.69% yield). LC-MS: m/z 400.6 [M+H], tRet=1.71 min. 1H NMR (400 MHz, DMSO-d6) δ 9.37 (s, 1H), 8.13-8.17 (t, J=8.4 Hz, 1H), 7.10-7.16 (m, 3H), 6.83-6.85 (d, J=7.6 Hz, 1H), 6.74-6.79 (t, J=9.6 Hz, 1H), 3.49 (broad s, 1H), 3.17 (broad s, 1H), 1.99 (m, 2H), 1.82 (m, 2H), 1.38 (s, 9H), 1.23-1.34 (m, 4H).

Preparation of VKT-511:

Tert-butyl ((1r,4r)-4-((7-fluoropyrimido[1,6-b]indazol-3-yl)amino)cyclohexyl)carbamate (C-1-Int-6) (0.11 g, 0.275 mmol) was treated with 20% v/v solution of TFA in DCM (3 mL) at 0° C. Allowed reaction mixture to stir at 0° C. for 1 hour. After completion of reaction, reaction mass was evaporated and triturated with ethyl acetate to get of TFA salt of compound. Compound was further purified by prep HPLC using formic acid buffer. Pure fractions were lyophilized to get (1r,4r)-N1-(7-fluoropyrimido[1,6-b]indazol-3-yl)cyclohexane-1,4-diamine (VKT-511). (0.045 g, 54.59% yield). LC-MS: m/z 300.02 [M+H], tRet=1.302 min. 1H NMR (400 MHz, DMSO-d6) δ 9.396 (s, 1H), 8.146-8.168 (m, 1H), 7.115-7.168 (m, 3H), 6.785 (m, 1H), 3.506 (broad s, 1H), 2.943 (broad s, 1H), 2.041-2.063 (d, J=8.8 Hz, 2H), 1.951-1.976 (d, J=10.0 Hz, 2H), 1.32-1.44 (m, 4H).

Synthesis of VKT-319

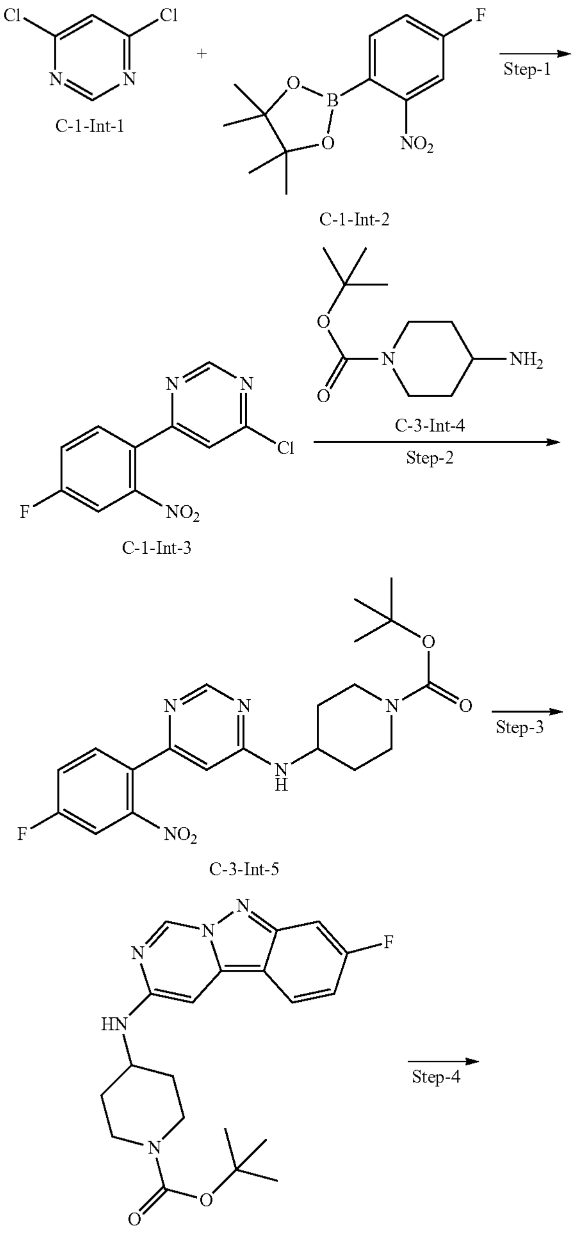

C-1-Int-1
C-1-Int-2
C-3-Int-4
C-1-Int-3
C-3-Int-5
C-3-Int-6

-continued

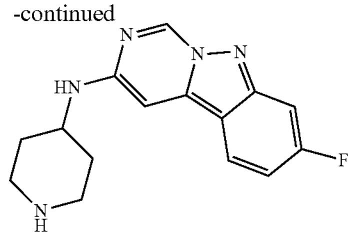

VKT-319

Synthesis of 4-chloro-6-(4-fluoro-2-nitrophenyl) pyrimidine (C-1-Int-3)

Same as for VKT-511

Synthesis of tert-butyl 4-((6-(4-fluoro-2-nitrophenyl)pyrimidin-4-yl)amino)piperidine-1-carboxylate (C-3-Int-5)

4-chloro-6-(4-fluoro-2-nitrophenyl) pyrimidine (C-1-Int-3) (0.32 g, 1.26 mmol) and tert-butyl 4-aminopipenidine-1l-carboxylate (C-3-Int-4) (1.01 g, 5.05 mmol) in DME (7 mL). Reaction mixture was irradiated at 140° C. for 40 minutes. After completion of reaction DME was evaporated under reduced pressure to get residue. Residue was triturated with diethyl ether (5 mL, two times) to remove upper impurities. Resulting crude material was purified on column chromatography using (20-25%) ethyl acetate hexane to get tert-butyl 4-((6-(4-fluoro-2-nitrophenyl)pyrimidin-4-yl) amino)piperidine-1-carboxylate (C-3-Int-5). (0.4 g, 75.94% yield). LC-MS: m/z 418.6 [M+H], tRet=1.60 min.

Synthesis of tert-butyl 4-((7-fluoropyrimido[1,6-b] indazol-3-yl)amino)piperidine-1-carboxylate (C-3-Int-6)

A mixture of tert-butyl 4-((6-(4-fluoro-2-nitrophenyl)pyrimidin-4-yl)amino)piperidine-1-carboxylate(C-3-Int-5) (0.4 g, 0.558 mmol.) and triethyl phosphite (0.796 g, 4.79 mmol.) was irradiated under microwave at 170° C. for 40 minutes. After completed of reaction triethyl phosphite was evaporated under reduced pressure (at 60° C.) to get residue. Residue was triturated with n-pentane (5 mL, two times) to remove remaining triethyl phosphite. Resulting Crude material was purified on column chromatography using (15-25%) ethyl acetate in hexane. Pure fractions were distilled out and triturated again with n-pentane to afford tert-butyl 4-((7-fluoropyrimido[1,6-b]indazol-3-yl)amino)piperidine-1-carboxylate (C-3-Int-6). (0.09 g, 24.37% yield) LC-MS: m/z 386.4 [M+H], tRet=1.73 min.

Preparation of VKT-319:

tert-butyl 4-((7-fluoropyrimido[1,6-b]indazol-3-yl) amino)piperidine-1-carboxylate (C-3-Int-6). (0.09 g, 0.275 mmol) was treated with 20% v/v solution of TFA in DCM (3 mL) at 0° C. Allowed reaction mixture to stir at 0° C. for 1 hour. After completion of reaction, the resulting TFA solution was evaporated and compound was further purified by prep HPLC using formic acid buffer. Pure fractions were lyophilized to get 7-fluoro-N-(piperidin-4-yl)pyrimido[1,6-b]indazol-3-amine (VKT-319). (0.0369 g, 55.39% yield). LC-MS: m/z 286.2 [M+H], tRet=1.288 min. 1H NMR (400 MHz, DMSO-d6) δ 9.44 (s, 1H), 8.10-8.14 (m, 1H), 7.378-7.397 (d, J=7.6 Hz, 1H), 7.144-7.200 (m, 2H), 6.788-6.832 (t, J=9.2 Hz, 1H), 3.840 (broad s, 1H), 3.277-3.307 (d, J=12.0 Hz, 2H), 2.946-3.002 (t, J=11.2 Hz, 2H), 2.072-2.105 (d, J=13.2 Hz, 2H), 1.629-1.655 (m, 2H).

Preparation of VKT-320

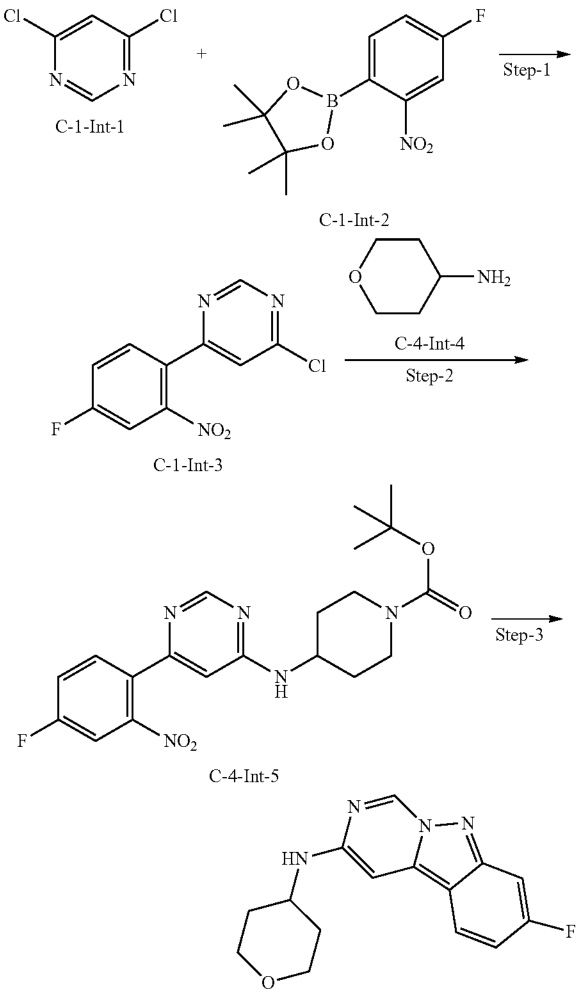

VKT-320

Synthesis of 4-choro-6-(4-fluoro-2-nitrophenyl)pyrimidine (C-1-Int-3)

4,6-dichloropyrimidine (0.250 g, 1.689 mmol) was taken in a microwave vial and dissolved in DMF (3.3 mL). 2-(4-fluoro-2-nitrophenyl)-4,4,5,5-tetramethyl-1,3,2-dioxaborolane (0.224 g, 0.844 mmol) and $Na_2CO_3$ (2M aq., 1.66 mL) was added into the reaction mixture. The mixture was purged with nitrogen for 20 minutes and added $PdCl_2$(dppf)·MDC (0.137 g, 0.168 mmol). Reaction mixture was sonicated for 15 minutes before heating in microwave at 100° C. for 10 minutes, starting material was observed on TLC, hence again nitrogen purged for 10 minutes and reaction mass was sonicated for 10 minutes and heated at 100° C. for 10 minutes. Reaction mass was quenched with water (5 mL) and extracted with ethyl acetate (3 mL×3), the organic layer was dried over sodium sulfate and concentrated to crude material. Crude material was purified by column chromatography using (7-9%) ethyl acetate: hexane to get 4-chloro-6-(4-fluoro-2-nitrophenyl) pyrimidine (C-1-Int-3). (0.087 g, 20.44% yield). 1H NMR (400 MHz, DMSO-d6) δ 9.094 (s, 1H), 8.252 (s, 1H), 8.157-8.142 (d, J=8.4 Hz, 1H), 8.00-8.038 (m, 1H), 7.81-7.85 (m, 1H).

Synthesis of 6-(4-fluoro-2-nitrophenyl)-N-(tetrahydro-2H-pyran-4-yl)pyrimidin-4-amine (C-4-Int-5)

4-chloro-6-(4-fluoro-2-nitrophenyl) pyrimidine (C-1-Int-3) (0.25 g, 0.985 mmol) and tetrahydro-2H-pyran-4-amine (C-4-Int-4) (0.398 g, 3.94 mmol) in DME (5 mL). Reaction mixture was irradiated at 140 C for 40 minutes. After completed of reaction DME was evaporated under reduced pressure to get residue. Residue was triturated with diethyl ether (5 mL, two times) to remove upper impurities. Resulting crude material was purified on column chromatography using (20-25%) ethyl acetate hexane to get 6-(4-fluoro-2-nitrophenyl)-N-(tetrahydro-2H-pyran-4-yl)pyrimidin-4-amine (C-4-Int-5). (0.202 g, 64.38% yield). LC-MS (Method-C): m/z 119.2 [M+2H], tRet=1.36 min.

Step-3. Synthesis of 7-fluoro-N-(tetrahydro-2H-pyran-4-yl)pyrimido[1,6-b]indazol-3-amine (VKT-320)

A mixture of 6-(4-fluoro-2-nitrophenyl)-N-(tetrahydro-2H-pyran-4-yl)pyrimidin-4-amine (C-4-Int-5)(0.202 g, 0.64 mmol.) and triethyl phosphite (0.527 g, 3.17 mmol.) was irradiated under microwave at 170° C. for 20 minutes. After completed of reaction triethyl phosphite was evaporated under reduced pressure (at 60° C.) to get residue. Residue was triturated with n-pentane (5 mL, two times) to remove remaining triethyl phosphite. Resulting crude material was purified on column chromatography using (15-25%) ethyl acetate in hexane to get 7-fluoro-N-(tetrahydro-2H-pyran-4-yl)pyrimido[1,6-b]indazol-3-amine (VKT-320). (0.077 g, 42.38% yield). LC-MS: m/z 287 [M+H], tRet=1.902 min. 1H NMR (400 MHz, DMSO-d6) δ 9.414 (s, 1H), 8.128-8.164 (t, J=6.0 Hz, 1H), 7.238-7.258 (d, J=8.0 Hz, 1H), 7.150-7.182 (m, 2H), 6.771-6.8157 (t, J=8.8 Hz, 1H), 3.900-3.928 (d, J=11.2 Hz, 2H), 3.806 (broad s, 1H), 3.420-3.475 (t, J=11.2 Hz, 2H), 1.914-1.944 (d, J=12.0 Hz, 2H), 1.509-1.558 (m, 2H).

Example 3

3.1: Kinase Activity Assay, Antiviral Activity Cell Culture Assay, and Metabolic Stability Assay 3.1.1: Table of Kinase activity for defined compounds

| Kinase Activity | Compound IC50 (M): | |
|---|---|---|
| Assay Data: Compound ID: | CDK7/ cyclin H | CDK9/ cyclin T1 |
| VKT-007 | >1.00E−05 | 1.10E−07 |
| VKT-007 | >1.00E−05 | 1.52E−07 |
| VKT-034 | 2.54E−06 | 8.07E−08 |
| VKT-036 | 3.64E−06 | 6.81E−08 |
| VKT-511 | — | 4.65E−08 |
| STAUROSPORINE | 3.99E−08 | 6.79E−09 |

| 3.1.2: Table of Kinase activity for defined compounds | |
|---|---|
| Compound ID: | CDK9/cyclin T1 |
| VKT-320 | 1.68E−06 |
| STAUROSPORINE | 9.49E−09 |

3.2: Antiviral Activity Cell Culture Assay Data:

For general reference (and as specifically stated in above antiviral assay methods section), the below unit definitions are listed:

EC50—compound concentration that reduces viral replication by 50%

EC90—compound concentration that reduces viral replication by 90%

CC50—compound concentration that reduces cell viability by 50%

For Selectivity Index (SI), the general definition is as follows: a selectivity index value provides an idea about the selectivity of a compound for killing the virus before killing the host. The higher the SI value, the larger the therapeutic window for antiviral treatment (inhibition of viral replication) prior to inducing cytotoxicity.

SI50—CC50/EC50 (selectivity index)

SI90—CC90/EC90 (selectivity index)

3.2.1: HCMV Primary Assay for In Vitro Cellular Antiviral Activity

Table 3.2.1 shows the anti-viral activity and toxicity of representative compounds. For descriptive purpose, the structure of VKT-026 is provided immediately herein below:

VKT-026

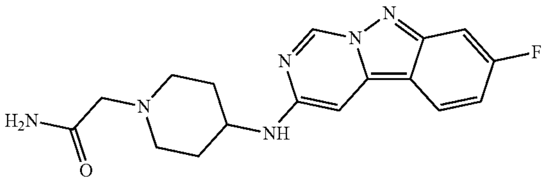

The antiviral activity of the compound against HCMV in the described Primary assay was measured by treating primary Human foreskin fibroblast (HFF) cells infected with HCMV with a range of compound concentrations—description of methods for this assay can be found in section 1.3.2.1. The concentration of compound that effected (inhibits) viral replication by 50% compared to vehicle treated controls ($EC_{50}$) of this compound is 1.48 μM. The concentration of compound that reduces cell viability by 50% (CC50) is 26.84 μM. For comparative purposes, the $EC_{50}$ of ganciclovir is 1.78 μM and CC50 is 150 μM for the same assay. Additional tested assay parameters in this Primary assay can be found in Table 3.2.1 and include EC90, S150, and S190 values—descriptions of those data points can be found in section 3.2.1.

| HCMV (Primary assay, virus strain AD169, HFF cells) | | | | | |
|---|---|---|---|---|---|
| Compound | EC50 (μM) | EC90 (μM) | CC50 (μM) | SI50 (μM) | SI90 (μM) |
| Ganciclovir | 1.78 | 5.67 | 150 | 84 | 26 |
| VKT-001 | 2 | 2 | 6.19 | 3 | 3 |
| VKT-002 | 2 | 2 | 7.42 | 4 | 4 |
| VKT-005 | 0.4 | 0.4 | 1.48 | 4 | 4 |
| VKT-006 | 10 | 10 | 32.48 | 3 | 3 |
| VKT-007 | 10 | 10 | 23.1 | 2 | 2 |
| VKT-008 | 10 | 10 | 38.82 | 4 | 4 |
| VKT-009-A | 0.4 | 0.4 | 0.57 | 1 | 1 |
| VKT-009-B | 0.08 | 0.08 | 0.17 | 2 | 2 |
| VKT-011 | 10 | 10 | 38.65 | 4 | 4 |
| VKT-012 | 50 | 50 | 50 | 1 | 1 |
| VKT-013 | 10 | 10 | 48.14 | 5 | 5 |
| VKT-015 | 10 | 10 | 27.72 | 3 | 3 |
| VKT-016 | 10 | 10 | 48.48 | 5 | 5 |
| VKT-017 | 10 | 10 | 21.38 | 2 | 2 |
| VKT-018 | 50 | 50 | 50 | 1 | 1 |
| VKT-019 | 10 | 10 | 32.01 | 3 | 3 |
| VKT-022-A | 10 | 10 | 44.99 | 4 | 4 |
| VKT-022-B | 10 | 10 | 49.76 | 5 | 5 |
| VKT-023 | 10 | 10 | 46.03 | 5 | 5 |
| VKT-025 | 10 | 10 | 48.1 | 5 | 5 |
| VKT-026 | 1.48 | 10 | 26.85 | 18 | 3 |
| VKT-027 | 10 | 10 | 43.74 | 4 | 4 |
| VKT-028 | 10 | 10 | 32.00 | 3 | 3 |
| VKT-029 | 50 | 50 | 50 | 1 | 1 |
| VKT-031 | 50 | 50 | 50 | 1 | 1 |
| VKT-032 | 10 | 10 | 26.23 | 3 | 3 |
| VKT-033 | 2 | 2 | 7.94 | 4 | 4 |
| VKT-034 | 10 | 10 | 19.46 | 2 | 2 |
| VKT-035 | 2 | 2 | 8.14 | 4 | 4 |
| VKT-036 | 10 | 10 | 16.54 | 2 | 2 |
| VKT-319 | 10 | 10 | 37.49 | 4 | 4 |
| VKT-320 | 10 | 10 | 38.54 | 4 | 4 |
| VKT-511 | 2 | 2 | 6.98 | 3 | 3 |

3.2.2: HCMV Primary Assay for In Vitro Cellular Antiviral Activity in a Viral Strain with Resistance to Frontline Drug Treatment:

| HCMV (Primary assay, virus strain GDGr K17-resistant isolate, HFF cells) | | | | | |
|---|---|---|---|---|---|
| Compound | EC50 (μM) | EC90 (μM) | CC50 (μM) | SI50 (μM) | SI90 (μM) |
| VKT-026 | 0.87 | 10 | 26.84 | 31 | 3 |
| Acyclovir | 16.77 | 150 | 150 | 9 | 1 |
| Cidofovir | 0.21 | 2.99 | 138.94 | 674 | 46 |

3.2.3: Human CMV Secondary Assay for In Vitro Cellular Antiviral:

| HCMV (Secondary assay, virus strain AD169, HFF cells) | | | |
|---|---|---|---|
| Compound | EC90 (μM) | CC50 (μM) | SI90 (μM) |
| Ganciclovir | 3.88 | 20 | 5 |
| Cidofovir | 0.75 | 20 | 27 |
| VKT-007 | 9.91 | 23.66 | 2 |
| VKT-026 | 9.87 | 27.18 | 3 |
| VKT-034 | 9.67 | 27.25 | 3 |
| VKT-036 | 9.94 | 34.1 | 3 |

3.2.4: Murine CMV Primary Assay for In Vitro Cellular Antiviral:

| Murine CMV (Primary assay, virus strain Smith, MEF cells) | | | | | |
|---|---|---|---|---|---|
| Compound | EC50 (μM) | EC90 (μM) | CC50 (μM) | SI50 (μM) | SI90 (μM) |
| VKT-007 | 10 | 10 | 35.54 | 4 | 4 |
| VKT-034 | 10 | 10 | 38.3 | 4 | 4 |
| VKT-036 | 10 | 10 | 32.37 | 3 | 3 |
| Ganciclovir | 5.48 | 24.93 | 150 | 27 | 6 |

3.2.5: Murine CMV Secondary Assay for In Vitro Cellular Antiviral:

| Murine CMV (Secondary assay, virus strain Smith, MEF cells) | | | | | |
|---|---|---|---|---|---|
| Compound | EC50 (uM) | EC90 (UM) | CC50 (μ.M) | SI50 (uM) | SI90 (μM) |
| Ganciclovir | 7.4 | 26 | 84.8 | 12 | 3 |
| VKT-026 | 0.17 | 5.38 | 50 | 50 | 9 |

3.2.6 Guinea Pig CMV Primary Assay for In Vitro Cellular Antiviral:

| Guinea pig CMV (Primary assay, virus strain 22122, GP lung cells) | | | | | |
|---|---|---|---|---|---|
| Compound | EC50 (μM) | EC90 (μM) | CC50 (μM) | SI50 (μM) | SI90 (μM) |
| VKT-007 | 10 | 10 | 18.46 | 2 | 2 |
| VKT-026 | 49.56 | 50 | 50 | 1 | 1 |
| VKT-034 | 10 | 10 | 24.97 | 2 | 2 |
| VKT-036 | 10 | 10 | 23.37 | 2 | 2 |
| Cidofovir | 1.01 | 1.17 | 150 | 148 | 128 |

3.2.7: Guinea Pig CMV Secondary Assay for In Vitro Cellular Antiviral:

| Guinea pig CMV (Secondary assay, virus strain 22122, GP lung cells) | | | | | |
|---|---|---|---|---|---|
| Compound | EC50 (μM) | EC90 (μM) | CC50 (μM) | SI50 (μM) | SI90 (μM) |
| VKT-007 | 8.21 | 23.65 | 34.2 | 4 | 1 |
| VKT-026 | 14.36 | 43.31 | 50 | 4 | 1 |
| VKT-034 | 6.08 | 14.9 | 50 | 8 | 3 |
| VKT-036 | 5.1 | 14.37 | 50 | 10 | 4 |
| Cidofovir | 2.78 | 3.52 | 100 | 36 | 28 |

3.2.8: VZV Primary Assay for In Vitro Cellular Antiviral Activity

-continued

| VZV (Primary assay, virus strain Ellen, cell line HFF) | | | | | |
|---|---|---|---|---|---|
| Compound | EC50 (μM) | EC90 (μM) | CC50 (μM) | SI50 (μM) | SI90 (μM) |
| VKT-002 | 2 | 2 | 7.9 | 4 | 4 |
| VKT-005 | 0.4 | 0.4 | 1.48 | 4 | 4 |
| VKT-006 | 10 | 10 | 27.24 | 3 | 3 |
| VKT-008 | 10 | 10 | 37.21 | 4 | 4 |
| VKT-015 | 10 | 10 | 39.71 | 4 | 4 |
| VKT-017 | 10 | 10 | 37.08 | 4 | 4 |
| VKT-018 | 50 | 50 | 50 | 1 | 1 |
| VKT-019 | 10 | 10 | 28.41 | 3 | 3 |
| VKT-022-B | 26.14 | 48.33 | 50 | 2 | 2 |
| VKT-023 | 10 | 10 | 44.74 | 4 | 4 |
| VKT-026 | 10 | 10 | 22.02 | 2 | 2 |
| VKT-027 | 10 | 10 | 47.18 | 5 | 5 |
| VKT-029 | 4.02 | 10 | 45.05 | 11 | 5 |
| VKT-033 | 10 | 10 | 15.43 | 2 | 2 |
| VKT-035 | 2 | 2 | 7.6 | 4 | 4 |
| Acyclovir | 5.59 | 69.44 | 150 | 27 | 2 |

3.2.9: VZV Primary Assay for In Vitro Cellular Antiviral Activity in a Viral Strain with Resistance to Frontline Drug Treatment:

| VZV (Primary assay, virus strain: 15-6-001 resistant isolate, HFF cell line) | | | | | |
|---|---|---|---|---|---|
| Compound | EC50 (μM) | EC90 (μM) | CC50 (μM) | SI50 (μM) | SI90 (μM) |
| VKT-029 | 10 | 10 | 47.21 | 5 | 5 |
| Acyclovir | 21 | 150 | 150 | 7 | 1 |
| Cidofovir | 1.14 | 30 | 115.46 | 101 | 4 |

3.2.10: HSV1 Primary Assay for In Vitro Cellular Antiviral Activity

| HSV1 (Primary assay, virus strain E-377, HFF cells) | | | | | |
|---|---|---|---|---|---|
| Compound | EC50 (μM) | EC90 (μM) | CC50 (μM) | SI50 (μM) | SI90 (μM) |
| VKT-002 | 10 | 10 | 20.84 | 2 | 2 |
| VKT-005 | 10 | 10 | 15.97 | 2 | 2 |
| VKT-006 | 10 | 10 | 38.54 | 4 | 4 |
| VKT-008 | 50 | 50 | 50 | 1 | 1 |
| VKT-015 | 50 | 50 | 50 | 1 | 1 |
| VKT-017 | 50 | 50 | 50 | 1 | 1 |
| VKT-018 | 50 | 50 | 50 | 1 | 1 |
| VKT-019 | 0.02 | 10 | 41.94 | 2621 | 4 |
| VKT-022-B | 50 | 50 | 50 | 1 | 1 |
| VKT-023 | 50 | 50 | 50 | 1 | 1 |
| VKT-026 | 10 | 10 | 10 | 4 | 4 |
| VKT-027 | 50 | 50 | 50 | 1 | 1 |
| VKT-029 | 50 | 50 | 50 | 1 | 1 |
| VKT-033 | 10 | 10 | 20.54 | 2 | 2 |
| VKT-035 | 10 | 10 | 15.93 | 2 | 2 |
| VKT-007 | 10 | 10 | 16.15 | 2 | 2 |
| VKT-034 | 10 | 10 | 18.69 | 2 | 2 |
| VKT-036 | 10 | 10 | 29.44 | 3 | 3 |
| Acyclovir | 2.56 | 150 | 150 | 59 | 1 |

3.2.11: HSV1 Primary Assay for In Vitro Cellular Antiviral Activity in a Viral Strain with Resistance to Frontline Drug Treatment:

| HSV1 (Primary assay, virus strain DM.2-resistant isolate, HFF cells) | | | | | |
|---|---|---|---|---|---|
| Compound | EC50 (μM) | EC90 (μM) | CC50 (μM) | SI50 (μM) | SI90 (μM) |
| VKT-019 | 10 | 10 | 48.5 | 5 | 5 |
| Acyclovir | 150 | 150 | 150 | 1 | 1 |
| Cidofovir | 1.07 | 150 | 150 | 141 | 1 |

3.2.12: HSV2 Primary Assay for In Vitro Cellular Antiviral Activity

| HSV2 (Primary assay, virus strain G, HFF cells) | | | | | |
|---|---|---|---|---|---|
| Compound | EC50 (μM) | EC90 (μM) | CC50 (μM) | SI50 (μM) | SI90 (μM) |
| VKT-002 | 10 | 10 | 24.42 | 2 | 2 |
| VKT-005 | 2 | 2 | 7.94 | 4 | 4 |
| VKT-006 | 10 | 10 | 42.83 | 4 | 4 |
| VKT-008 | 50 | 50 | 50 | 1 | 1 |
| VKT-015 | 50 | 50 | 50 | 1 | 1 |
| VKT-017 | 50 | 50 | 50 | 1 | 1 |
| VKT-018 | 50 | 50 | 50 | 1 | 1 |
| VKT-019 | 10 | 10 | 38.11 | 4 | 4 |
| VKT-022-B | 50 | 50 | 50 | 1 | 1 |
| VKT-023 | 50 | 50 | 50 | 1 | 1 |
| VKT-026 | 10 | 50 | 29.38 | 3 | 3 |
| VKT-027 | 50 | 50 | 50 | 1 | 1 |
| VKT-029 | 50 | 50 | 50 | 1 | 1 |
| VKT-033 | 10 | 10 | 21.83 | 2 | 2 |
| VKT-035 | 10 | 10 | 17.68 | 2 | 2 |
| Acyclovir | 2.56 | 150 | 150 | 59 | 1 |

3.2.13: EBV Primary Assay for In Vitro Cellular Antiviral Activity

| Epstein-Barr (Primary assay-Akata strain, Akata cells) | | | | | |
|---|---|---|---|---|---|
| Compound | EC50 (μM) | EC90 (μM) | CC50 (μM) | SI50 (μM) | SI90 (μM) |
| VKT-002 | 1.78 | 2 | 6.69 | 4 | 3 |
| VKT-005 | 10 | 10 | 39.36 | 4 | 4 |
| VKT-006 | 8.32 | 10 | 33.55 | 4 | 3 |
| VKT-008 | 8.16 | 44.03 | 50 | 6 | 1 |
| VKT-015 | 8.73 | 29.93 | 50 | 6 | 2 |
| VKT-017 | 23.39 | 41.48 | 50 | 2 | 1 |
| VKT-018 | 45.71 | 50 | 50 | 1 | 1 |
| VKT-019 | 10 | 10 | 42.27 | 4 | 4 |
| VKT-022-B | 6.13 | 9.3 | 50 | 8 | 5 |
| VKT-023 | 29.48 | 50 | 50 | 2 | 1 |
| VKT-026 | 10 | 10 | 42.86 | 4 | 4 |
| VKT-027 | 42.78 | 50 | 50 | 1 | 1 |
| VKT-029 | 4.79 | 12.06 | 50 | 10 | 4 |
| VKT-033 | 9.25 | 10 | 37.98 | 4 | 4 |
| VKT-035 | 10 | 10 | 31.95 | 3 | 3 |
| VKT-007 | 1.3 | 5.5 | 20.29 | 16 | 4 |
| VKT-034 | 1.06 | 2.91 | 30.88 | 29 | 11 |
| VKT-036 | 1.35 | 7.57 | 12.61 | 9 | 2 |
| Cidofovir | 3.31 | 74.16 | 100 | 30 | 1 |

3.2.14: HPV Primary Assay for In Vitro Cellular Antiviral Activity

| Human papillomavirus 11 (Primary assay, virus strain HE611260.1, C-33 A cells) | | | | | |
|---|---|---|---|---|---|
| Compound | EC50 (μM) | EC90 (μM) | CC50 (μM) | SI50 (μM) | SI90 (μM) |
| VKT-007 | 10 | 10 | 49.85 | 5 | 5 |
| VKT-026 | 17.05 | 26.72 | 50 | 3 | 3 |
| VKT-034 | 10 | 10 | 29.25 | 3 | 3 |
| VKT-036 | 10 | 10 | 21.18 | 2 | 2 |
| VKT-320 | 7.99 | 19.83 | 50 | 6 | 3 |
| 9-[2-phosohono-methoxy)ethyl]guanine | 10 | 10 | 39.36 | 4 | 4 |

3.2.15: HHV-6B Primary Assay for In Vitro Cellular Antiviral Activity

| Human herpes virus 6B (Primary assay, virus strain Z29, MOLT-3 cells) | | | | | |
|---|---|---|---|---|---|
| Compound | EC50 (μM) | EC90 (μM) | CC50 (μM) | SI50 (μM) | SI90 (μM) |
| Cidofovir | 8.45 | 27.67 | 100 | 12 | 6 |
| VKT-007 | 5.32 | 9.88 | 27.85 | 5 | 3 |
| VKT-026 | 10 | 10 | 48.58 | 5 | 5 |
| VKT-034 | 8.71 | 10 | 32.83 | 4 | 3 |
| VKT-036 | 5.86 | 8.02 | 28.06 | 5 | 3 |
| VKT-320 | 8.96 | 32.61 | 50 | 6 | 2 |

3.2.16: HHV-8 Primary Assay for In Vitro Cellular Antiviral Activity

| Human herpes virus 8 (Primary assay, virus strain BCBL-1 , BCBL-1 cells) | | | | | |
|---|---|---|---|---|---|
| Compound | EC50 (μM) | EC90 (μM) | CC50 (μM) | SI50 (μM) | SI90 (μM) |
| Cidofovir | 3.22 | 15.8 | 100 | 32 | 6 |
| VKT-007 | 10 | 10 | 31.39 | 3 | 3 |
| VKT-026 | 10 | 10 | 42.43 | 4 | 4 |
| VKT-034 | 10 | 10 | 31.57 | 3 | 3 |
| VKT-036 | 5.69 | 8.86 | 12.9 | 2 | 1 |
| VKT-320 | 22.12 | 44.19 | 50 | 2 | 1 |

3.2.17: Adenovirus Primary Assay for In Vitro Cellular Antiviral Activity

| Adenovirus (primary assay-HFF cells, Adenoid75 strain) | | | | | |
|---|---|---|---|---|---|
| Compound | EC50 (μM) | EC90 (μM) | CC50 (μM) | SI50 (μM) | SI90 (μM) |
| VKT-002 | 4.44 | 10 | 21.19 | 5 | 2 |
| VKT-005 | 2 | 2 | 3.81 | 2 | 2 |
| VKT-006 | 10 | 10 | 30.53 | 3 | 3 |
| VKT-008 | 10 | 10 | 48.63 | 5 | 5 |
| VKT-015 | 7.13 | 10 | 41.76 | 6 | 4 |
| VKT-017 | 10 | 10 | 46.68 | 5 | 5 |
| VKT-018 | 3.69 | 50 | 50 | 14 | 1 |
| VKT-019 | 6.02 | 10 | 29.9 | 5 | 3 |
| VKT-022-B | 43.52 | 50 | 50 | 1 | 1 |
| VKT-023 | 50 | 50 | 50 | 1 | 1 |
| VKT-026 | 7.71 | 50 | 24.7 | 3 | 2 |
| VKT-027 | 50 | 50 | 50 | 1 | 1 |
| VKT-029 | 5.12 | | 50 | 10 | 1 |
| VKT-033 | 10 | 10 | 28.22 | 3 | 3 |
| VKT-035 | 10 | 10 | 17.52 | 2 | 2 |
| Cidofovir | 4.91 | 150 | 150 | 31 | 1 |

3.2.18: Adenovirus Secondary Assay for In Vitro Cellular Antiviral Activity

| Adeno (secondary assay, virus strain Adenoid75, HFF cells) | | | |
|---|---|---|---|
| Compound | EC90 (μM) | CC50 (μM) | SI90 (μM) |
| VKT-015 | 17.51 | 48.58 | 3 |
| VKT-018 | 16.36 | 97.11 | 6 |
| VKT-029 | 3.91 | 100 | 26 |
| Cidofovir | 3.27 | 100 | 31 |

3.3: Metabolic Stability Assay Data:

3.3.1: Metabolic Stability Assay Data Performed in Mouse Liver Microsomes:

Metabolic stability of positive control and test compounds in mice liver microsomes

| Compound | % Remaining at 60 min |
|---|---|
| Imipramine | 2 |
| VKT-007 | 54 |
| VKT-034 | 81 |
| VKT-036 | 82 |
| VKT-511 | 107 |
| VKT-320 | 37 |

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Sanchez V, McElroy A K, Spector D H, Mechanisms governing maintenance of Cdk1/cyclin B1 kinase activity in cells infected with human cytomegalovirus. J. Virol. 77(24), 13214-13224 (2003).

Arend et al., Kinome Profiling Identifies Druggable Targets for Novel Human Cytomegalovirus (HCMV) Antivirals. Mol Cell Proteomics. 2017 April; 16(4 suppl 1):S263-S276.

L. S. Azevedo et al., Cytomegalovirus infection in transplant recipients. Clinics (Sao Paulo). 2015 July; 70(7): 515-523.

Sinclair and Sissons, Latency and reactivation of human cytomegalovirus. J. Gen. Virol. 87:1763-1779, 2006.

Simon D M, Levin S. Infectious complications of solid organ transplantations. Infect Dis Clin of North Am. 2001; 15((2)):521-49.

Kapasi A J, Spector D H, Inhibition of the cyclin-dependent kinases at the beginning of human cytomegalovirus infection specifically alters the levels and localization of the RNA polymerase II carboxyl-terminal domain kinases CDK9 and CDK7 at the viral transcriptosome. J. Virol. 82(1), 394-407 (2008)

Sanchez V, Spector D H, Cyclin-dependent kinase activity is required for efficient expression and posttranslational modification of human cytomegalovirus proteins and for production of extracellular particles. J. Virol. 80(12), 5886-5896 (2006)

Tamrakar S, Kapasi A J, Spector D H, Human cytomegalovirus infection induces specific hyperphosphorylation of the carboxyl-terminal domain of the large subunit of RNA polymerase II that is associated with changes in the abundance, activity, and localization of CDK9 and CDK7. J. Virol. 79(24), 15477-15493 (2005)

Sanchez V, McElroy A K, Yen J et al.: Cyclin-dependent kinase activity is required at early times for accurate processing and accumulation of the human cytomegalovirus UL122-123 and UL37 immediate-early transcripts and at later times for virus production. J. Virol. 78(20), 11219-11232 (2004).

Hartline C B, Keith K A, Eagar J, Harden E A, Bowlin T L, Prichard M N. Antiviral Res. 2018. A standardized approach to the evaluation of antivirals against DNA viruses: Orthopox-, adeno-, and herpesviruses. November; 159:104-112. doi: 10.1016/j.antiviral.2018.09.015. Epub 2018 Oct. 1. PMID: 30287226

Prichard M N, Keith K A, Quenelle D C, Kern E R. Activity and mechanism of action of N-methanocarbathymidine against herpesvirus and orthopoxvirus infections. Antimicrob Agents Chemother. 2006; 50(4):1336-41. PubMed PMID: 16569849; PubMed Central PMCID: PMC1426929.

Keith K A, Hartline C B, Bowlin T L, Prichard M N. Antiviral Res. 2018. A standardized approach to the evaluation of antivirals against DNA viruses: Polyomaviruses and lymphotropic herpesviruses. November; 159: 122-129. doi: 10.1016/j.antiviral.2018.09.016. Epub 2018 Oct. 1.PMID: 30287227

Prichard M N, Frederick S L, Daily S, Borysko K Z, Townsend L B, Drach J C, et al. Benzimidazole analogs inhibit human herpesvirus 6. Antimicrob Agents Chemother. 2011; 55(5):2442-5. PubMed PMID: 21300829; PubMed Central PMCID: PMC3088228.

Gill R B, Frederick S L, Hartline C B, Chou S, Prichard M N. Conserved retinoblastoma protein-binding motif in human cytomegalovirus UL97 kinase minimally impacts viral replication but affects susceptibility to maribavir. Virol J. 2009; 6:9. PubMed PMID: 19159461; PubMed Central PMCID: PMC2636770.

Leung A Y, Suen C K, Lie A K, Liang R H, Yuen K Y, Kwong Y L. Quantification of polyoma B K viruria in hemorrhagic cystitis complicating bone marrow transplantation. Blood. 2001; 98(6):1971-8. PubMed PMID: 11535537

Beadle J R, Valiaeva N, Yang G, Yu J H, Broker T R, Aldem K A, et al. Synthesis and Antiviral Evaluation of Octadecyloxyethyl Benzyl 9-[(2-Phosphonomethoxy)ethyl] guanine (ODE-Bn-PMEG), a Potent Inhibitor of Transient HPV DNA Amplification. J Med Chem. 2016; 59(23): 10470-8. PubMed PMID: 27933957

Li R, Hayward S D. Potential of protein kinase inhibitors for treating herpesvirus associated disease. Trends Microbiol. 2013; 21(6): 286-295. PubMed PMID: 23608036.

Lavoie J N, Landry M C, Faure R L, Champagne C. Src-family kinase signaling, actin-mediated membrane trafficking and organellar dynamics in the control of cell fate: lessons to be learned from the adenovirus E4orf4 death factor. Cell Signal. 2010; 22(11):1604-1614. PubMed PMID: 20417707

Gupta S, Kumar P, Das B C. HPV: Molecular pathways and targets. Curr Probl Cancer; 42(2): 161-174. PubMed PMID: 29706467

Wang M, Yang, L, Meng J, Pan J, Zhang C, et al. Functionally active cyclin-dependent kinase 9 is essential for porcine reproductive and respiratory syndrome virus subgenomic RNA synthesis. Mol Immunol. 2021; July(135): 351-364. PubMed PMID: 33990004

Prasad, V, Suomalainen M, Hemmi S, Greber U F. Cell Cycle-Dependent Kinase Cdk9 Is a Postexposure Drug Target against Human Adenoviruses. ACS Infect Dis. 2017; 3(6):398-405. PubMed PMID: 28434229

Although the foregoing subject matter has been described in some detail by way of illustration and example for purposes of clarity of understanding, it will be understood by those skilled in the art that certain changes and modifications can be practiced within the scope of the appended claims.
That which is claimed:
1. A compound of formula (I):
VKT-001
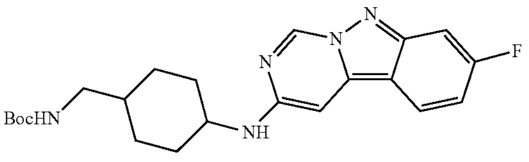
VKT-002
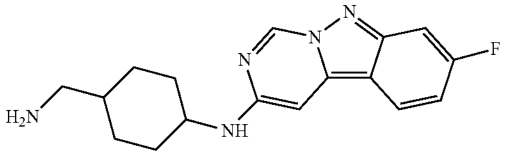
VKT-005
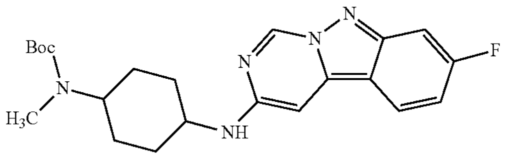
VKT-006
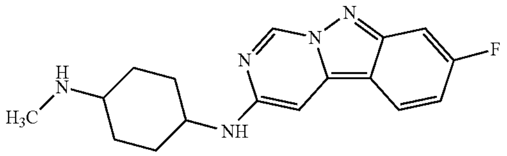
VKT-007
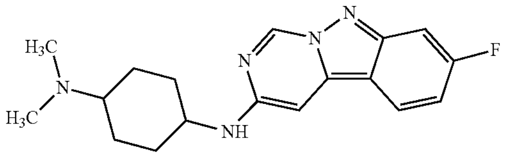
VKT-008
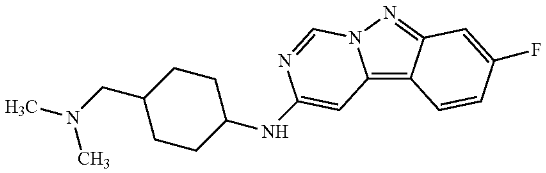
VKT-009-A
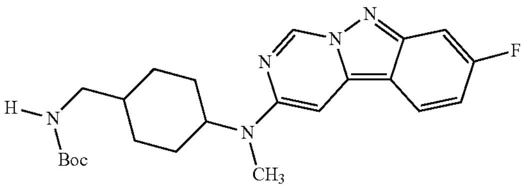
-continued
VKT-009-B
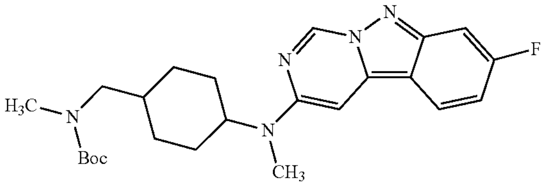
VKT-011
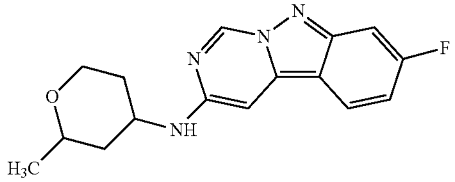
VKT-012
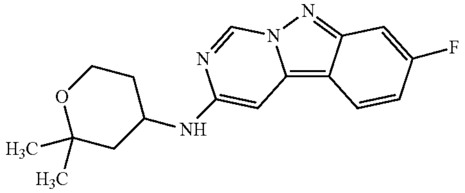
VKT-013
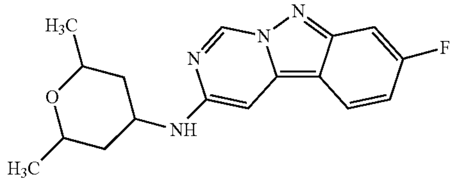
VKT-015
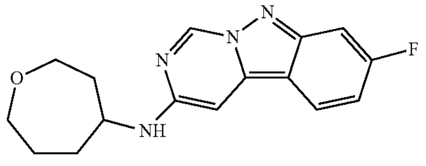
VKT-016
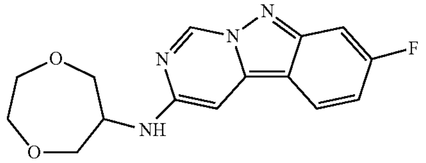
VKT-017
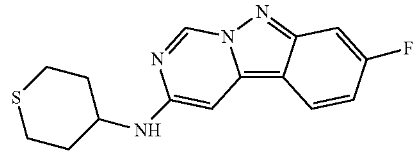
VKT-018
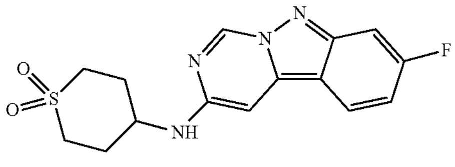

-continued
VKT-019
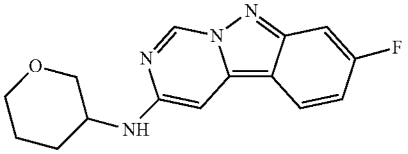
VKT-022-A
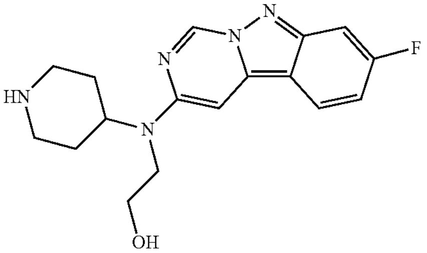
VKT-022-B
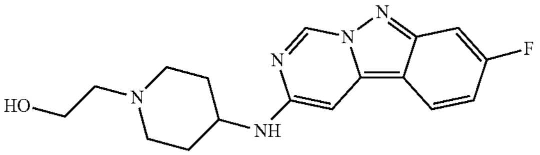
VKT-023
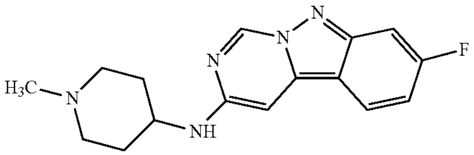
VKT-025
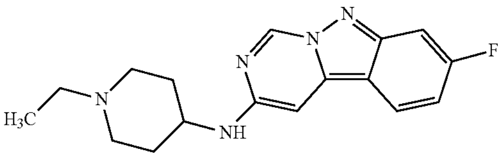
VKT-026
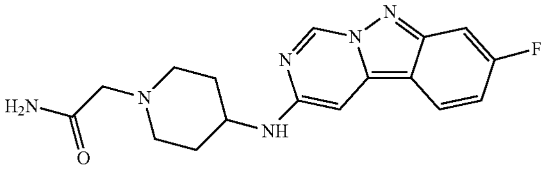
VKT-027
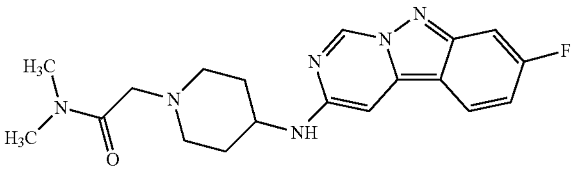
VKT-028
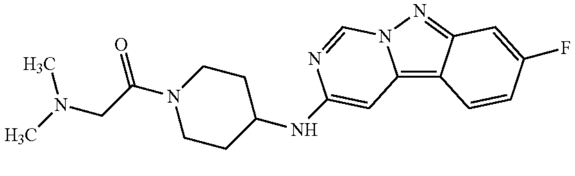
-continued
VKT-029
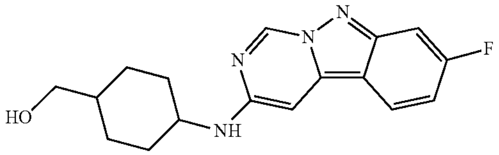
VKT-031
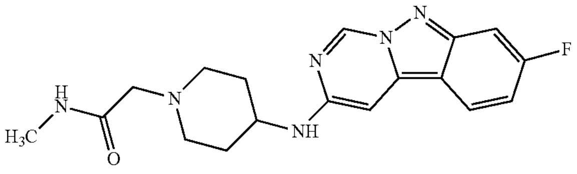
VKT-032
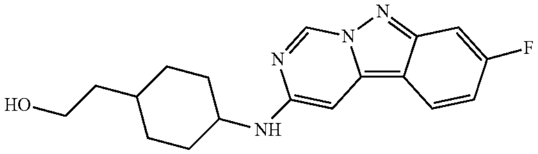
VKT-033
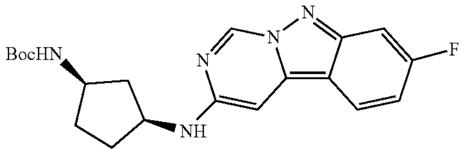
VKT-034
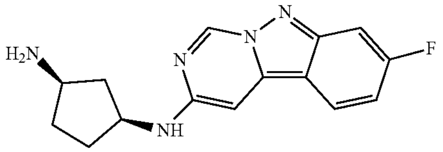
VKT-035
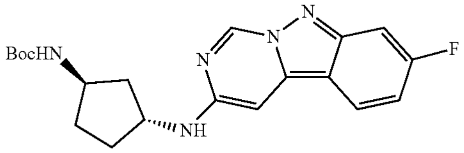
VKT-036
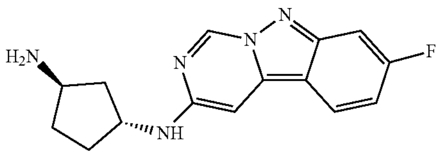
VKT-511
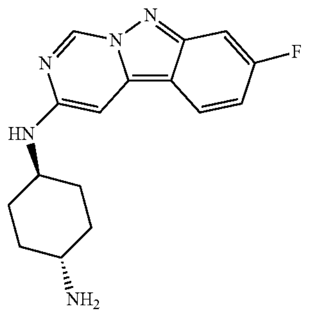

-continued

VKT-319

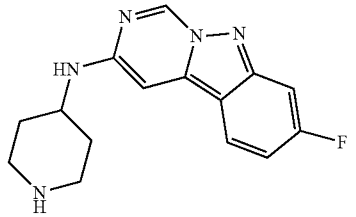

VKT-320

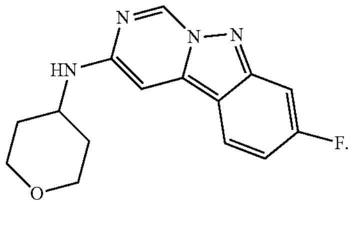

wherein:

$X^1$ is CH or N;

$R^1$ is selected from unsubstituted or substituted branched or linear $C_1$-$C_{12}$ alkyl, $C_3$-$C_{12}$ cycloalkyl, $C_3$-$C_{12}$ heterocycloalkyl, aryl, heteroaryl, and —C(O)—$R_6$, wherein $R_6$ is selected from unsubstituted or substituted $C_1$-$C_{12}$ alkyl, $C_3$-$C_{12}$ cycloalkyl, $C_3$-$C_{12}$ heterocycloalkyl, aryl, and heteroaryl;

$R^2$, $R^3$, $R^4$, and $R^5$ are each independently selected from hydrogen, halogen, amine, unsubstituted or substituted branched or linear $C_1$-$C_{12}$ alkyl, $C_3$-$C_{12}$ cycloalkyl, $C_3$-$C_{12}$ heterocycloalkyl, aryl, heteroaryl, and —C(O)—$R^6$, wherein $R_6$ is selected from unsubstituted or substituted $C_1$-$C_{12}$ alkyl, $C_3$-$C_{12}$ cycloalkyl, $C_3$-$C_{12}$ heterocycloalkyl, aryl, and heteroaryl;

or a pharmaceutically acceptable salt, hydrate, solvate, stereoisomer, ester, tautomer, or prodrug thereof.

2. The compound of claim 1, wherein the branched or linear $C_1$-$C_{12}$ alkyl, $C_3$-$C_{12}$ cycloalkyl, $C_3$-$C_{12}$ heterocycloalkyl, aryl, heteroaryl at each occurrence are optionally substituted with one or more substituent groups selected from halogen, hydroxyl, alkoxyl, cyano, nitro, oxo, —$NR^7R^8$, —$CONR^9R^{10}$, —$COOR^{11}$, —$OR^{12}$, —$OSO_3R^{13}$, —$SR^{14}$, $SO_2R^{15}$, and $SO_3R^{16}$; wherein $R^7$, $R^8$, $R^9$, $R^{10}$, $R^{11}$, $R^{12}$, $R^{13}$, $R^{14}$, $R^{15}$, and $R^{16}$ are each independently selected from hydrogen, unsubstituted or substituted $C_1$-$C_{12}$ alkyl, $C_3$-$C_{12}$ cycloalkyl, and aryl.

3. The compound of claim 1, wherein $R^1$ is selected from an amino-substituted cyclohexyl, an amino-substituted cyclopentyl, and a $C_3$-$C_{12}$ heterocycloalkyl.

4. The compound of claim 3, wherein the $C_3$-$C_{12}$ heterocycloalkyl is selected from a substituted or unsubstituted morpholine, tetrahydropyran, piperidine, and pyrrolidine.

5. The compound of claim 1, wherein:

(a) at least one of $R^2$, $R^3$, $R^4$, or $R^5$ is Cl or F;

(b) at least one of $R^2$, $R^3$, $R^4$, or $R^5$ is H;

(c) at least one of $R^2$, $R^3$, $R^4$, or $R^5$ is an independently substituted or unsubstituted $C_1$-$C_{12}$ alkyl;

(d) $R^2$, $R^3$, and $R^5$ are H, and $R^4$ is Cl;

(e) $R^2$, $R^3$, and $R^5$ are H, and $R^4$ is F;

(f) $R^2$, $R^3$, and $R^5$ are H, and $R^4$ is substituted or unsubstituted $C_1$-$C_{12}$ alkyl;

(g) $R^2$, $R^4$, and $R^5$ are H, and $R^3$ is Cl;

(h) $R^2$, $R^4$, and $R^5$ are H, and $R^3$ is F;

(i) $R^2$, $R^4$, and $R^5$ are H, and $R^3$ is substituted or unsubstituted $C_1$-$C_{12}$ alkyl;

(j) at least one of $R^2$, $R^3$, $R^4$, or $R^5$ is methyl or trifluoromethyl; or (k) $X^1$ is CH, $R^1$ is $C_3$-$C_{12}$ heterocycloalkyl; $R^2$, $R^4$, and $R^5$ are each H; and $R^3$ is halogen.

6. The compound of claim 1, wherein the compound of formula (I) has a structure selected from:

VKT-001

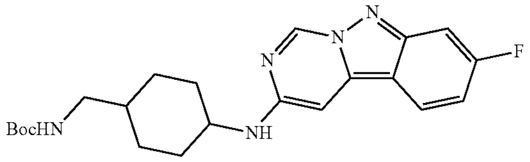

VKT-002

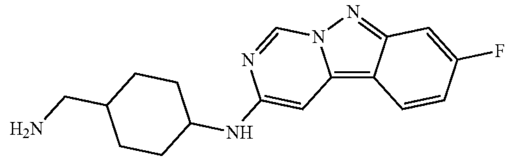

VKT-005

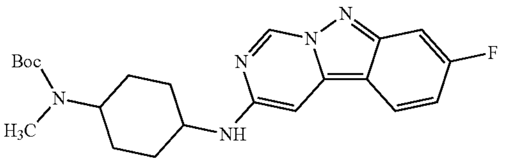

VKT-006

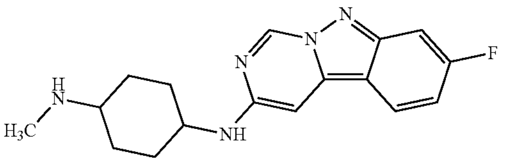

VKT-007

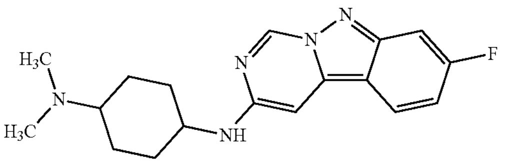

VKT-008

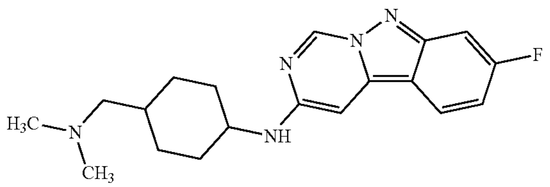

VKT-009-A

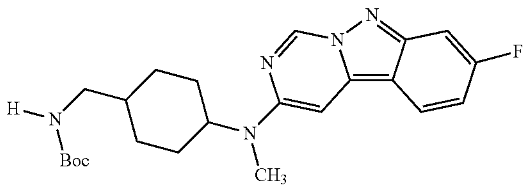

-continued
VKT-009-B
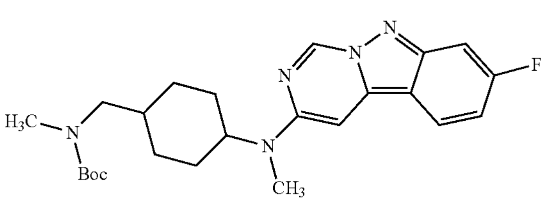
VKT-011
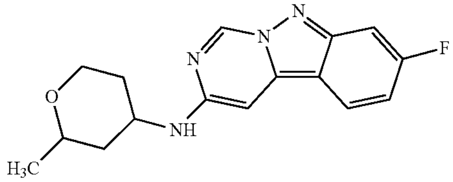
VKT-012
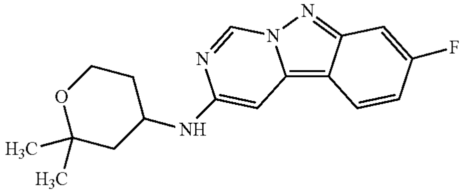
VKT-013
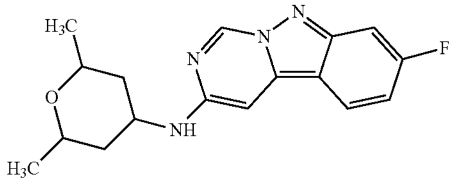
VKT-015
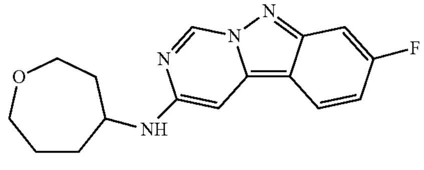
VKT-016
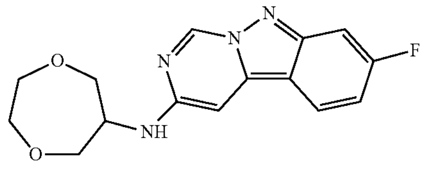
VKT-017
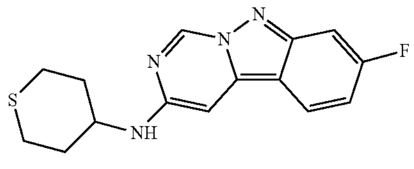
VKT-018
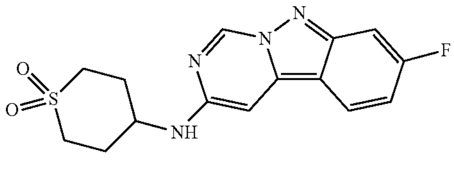
-continued
VKT-019
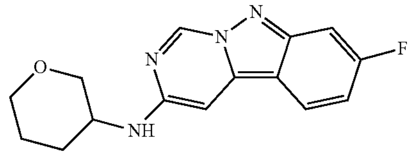
VKT-022-A
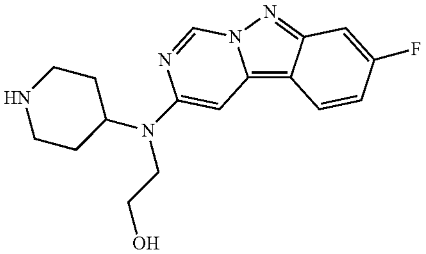
VKT-022-B
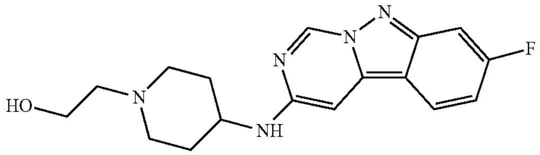
VKT-023
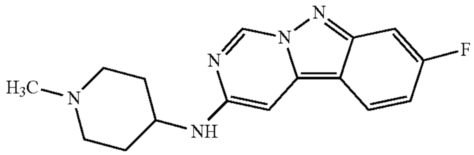
VKT-025
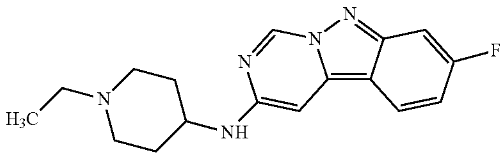
VKT-026
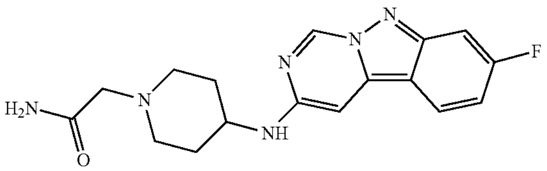
VKT-027
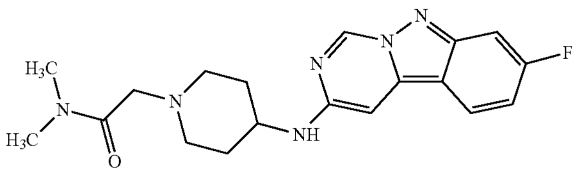
VKT-028
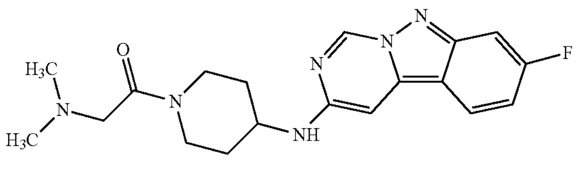

-continued

VKT-029

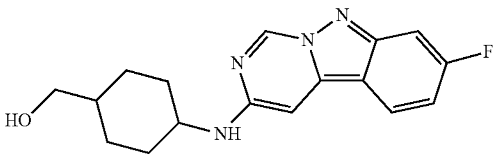

VKT-031

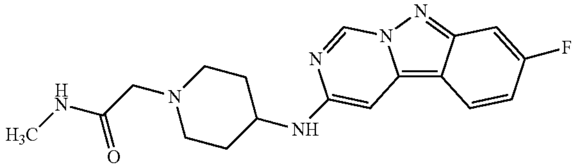

VKT-032

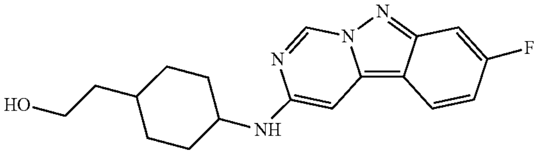

VKT-033

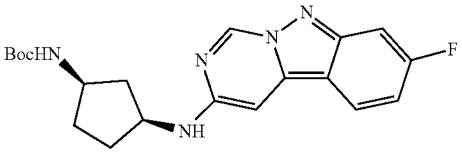

VKT-034

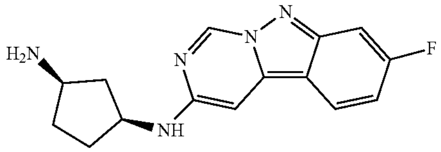

VKT-035

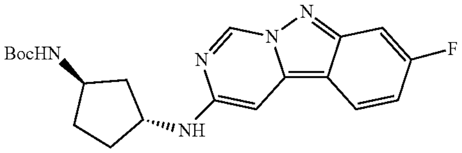

VKT-036

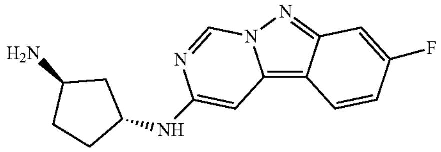

VKT-511

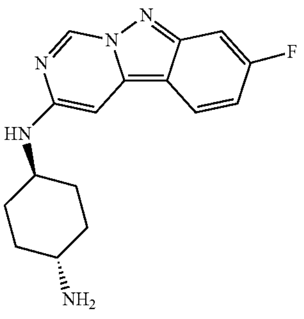

-continued

VKT-319

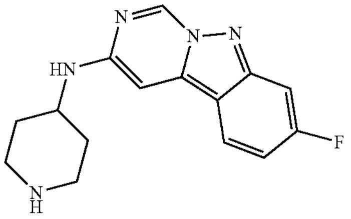

VKT-320

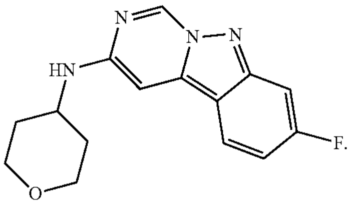

7. A pharmaceutical composition comprising a compound of claim 1, and a pharmaceutically acceptable excipient.

8. A method for treating a viral disease, viral disorder, or viral condition associated with cyclin-dependent kinase (CDK) function, the method comprising administering to a subject in need of treatment thereof, a therapeutically effective amount of a compound of formula (I) according to claim 1 or a composition thereof, wherein the viral disease, viral disorder, or viral condition is associated with one or more of an increase in activity of a CDK, a decrease in activity of a CDK, a CDK mutation, CDK overexpression, and an upstream pathway activation of CDK;

wherein the method inhibits CDK; and wherein the viral disease, viral disorder, or viral condition associated with CDK function is selected from Human Cytomegalovirus (HCMV), Varicella-Zoster (VZV), Herpes simplex virus-1 (HSV-1), Herpes simplex virus-2 (HSV-2), Epstein-Barr (EBV), papillomavirus (HPV), Human herpes virus-6b (HHV-6b), Human herpes virus-8 (HHV-8), adenovirus-5, and combinations thereof.

9. A method for treating or preventing a viral infection of a host, wherein the host has, is suspected of having, or is at risk of contracting a viral infection from a virus selected from Human Cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, Human papillomavirus (HPV), and combinations thereof, the method comprising administering to the host a therapeutically effective amount of a compound of formula (I) according to claim 1 or a composition thereof, wherein the host is selected from one or more of a cell, a tissue, an organ, and an individual organism.

10. The method of claim 9, wherein the individual organism is a mammal.

11. The method of claim 10, wherein the mammal is a human.

12. The method of claim 9, further comprising concurrently or sequentially administering to the host one or more additional anti-viral agents in combination with the compound of formula (I) or a composition thereof.

13. The method of claim 12, wherein the one or more additional anti-viral agents is selected from ganciclovir, valganciclovir, valacyclovir, cidofovir and combinations thereof.

14. The method of claim 9, wherein the administering to the host a therapeutically effective amount of a compound of formula (I) or a composition thereof inhibits replication of Human cytomegalovirus (HCMV), Varicella-Zoster (VZV), Epstein-Barr (EBV), Human herpes virus-6b (HHV-6b), Human herpes virus-8 (HHV-8), Herpes simplex virus-1 (HSV-1), Herpes simplex virus-2 (HSV-2), Adenovirus-5, and/or Human papillomavirus (HPV) infection in the subject.

15. The method of claim 9, wherein the infection is selected from a latent infection, an active infection, and a reactivation of an infection after latency.

16. The method of claim 9, wherein the administering to the host a therapeutically effective amount of a compound of formula (I) or a composition thereof is oral, intravenous, or topical administration.

17. The method of claim 9, wherein the host is immunocompromised, has undergone, is undergoing, or is expected to undergo a solid organ transplant or tissue transplant, is infected with HIV, and/or is a congenitally infected fetus or neonate.

18. The method of claim 17, wherein the solid organ is selected from a heart, a kidney, a liver, a lung, a pancreas, an intestine, a thymus, and/or other organ/human tissues.

* * * * *